US 9,173,576 B2

(12) United States Patent
Yuen et al.

(10) Patent No.: US 9,173,576 B2
(45) Date of Patent: Nov. 3, 2015

(54) BIOMETRIC MONITORING DEVICE HAVING A BODY WEIGHT SENSOR, AND METHODS OF OPERATING SAME

(71) Applicant: Fitbit, Inc., San Francisco, CA (US)

(72) Inventors: Shelten Gee Jao Yuen, Berkeley, CA (US); Eric Nathan Friedman, San Francisco, CA (US); James Park, Berkeley, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 14/261,354

(22) Filed: Apr. 24, 2014

(65) Prior Publication Data

US 2014/0257053 A1 Sep. 11, 2014

Related U.S. Application Data

(60) Continuation of application No. 14/027,164, filed on Sep. 14, 2013, now Pat. No. 8,747,312, which is a division of application No. 13/929,868, filed on Jun. 28, 2013, now Pat. No. 8,696,569, which is a division (Continued)

(51) Int. Cl.
*G01G 19/00* (2006.01)
*A61B 5/00* (2006.01)
(Continued)

(52) U.S. Cl.
CPC ............ *A61B 5/0205* (2013.01); *A61B 5/0002* (2013.01); *A61B 5/0022* (2013.01);
(Continued)

(58) Field of Classification Search
CPC ... G01G 19/44; G01G 19/4146; G01G 23/42; G01G 23/3721; G01G 19/445–19/50; G06F 19/3475; G06F 19/3487; G06F 19/30–19/366; A61B 5/0537; A61B 5/4872–5/4875; A61B 2560/0462–2560/0468; A61B 2560/0487; A61B 5/0002

See application file for complete search history.

(56) References Cited

U.S. PATENT DOCUMENTS

| 1,924,652 A | 8/1933 | Rivas et al. |
| 3,321,036 A | 5/1967 | Keenan et al. |

(Continued)

FOREIGN PATENT DOCUMENTS

| EP | 1 721 237 | 8/2012 |
| GB | 2454705 A | 5/2009 |

(Continued)

OTHER PUBLICATIONS

U.S. Appl. No. 14/201,467, filed Mar. 7, 2014, Yuen et al.
(Continued)

*Primary Examiner* — William Thomson
*Assistant Examiner* — Marie Archer
(74) *Attorney, Agent, or Firm* — Weaver Austin Villeneuve & Sampson LLP

(57) ABSTRACT

A system comprising a biometric monitoring device including a housing including a platform to receive at least one foot of the user, a body weight sensor to generate body weight data, processing circuitry to calculate user weight data which corresponds to the user's weight, using the body weight data, and communication circuitry to: (a) receive user identification data which identifies the user or a portable activity monitoring device, and (b) transmit the user weight data to data storage associated with the user identification data. The system further includes the portable activity monitoring device including a housing having a physical size and shape that is adapted to couple to the user's body, a sensor to generate sensor data, and communication circuitry to receive physiologic data which is based on the user weight data, and processing circuitry to calculate activity data using the sensor data and physiologic data.

20 Claims, 41 Drawing Sheets

Related U.S. Application Data of application No. 13/346,275, filed on Jan. 9, 2012, now Pat. No. 8,475,367.

(60) Provisional application No. 61/431,020, filed on Jan. 9, 2011.

(51) Int. Cl.

| | | |
|---|---|---|
| *G06F 19/00* | (2011.01) | |
| *A61B 5/0205* | (2006.01) | |
| *G01G 19/44* | (2006.01) | |
| *A61B 5/11* | (2006.01) | |
| *G01G 23/37* | (2006.01) | |
| *G06Q 50/22* | (2012.01) | |
| *G01G 19/50* | (2006.01) | |
| *A61B 5/0402* | (2006.01) | |
| *A61B 5/053* | (2006.01) | |
| *G06F 21/32* | (2013.01) | |
| *G09B 5/00* | (2006.01) | |
| *G06F 3/041* | (2006.01) | |
| *A61B 5/02* | (2006.01) | |
| *A61B 5/107* | (2006.01) | |
| *A61B 5/021* | (2006.01) | |
| *A61B 5/024* | (2006.01) | |

(52) U.S. Cl.
CPC ............. *A61B5/0024* (2013.01); *A61B 5/0059* (2013.01); *A61B 5/02007* (2013.01); *A61B 5/0402* (2013.01); *A61B 5/053* (2013.01); *A61B 5/107* (2013.01); *A61B 5/1118* (2013.01); *A61B 5/4872* (2013.01); *A61B 5/7275* (2013.01); *A61B 5/742* (2013.01); *G01G 19/44* (2013.01); *G01G 19/50* (2013.01); *G01G 23/3728* (2013.01); *G06F 3/0412* (2013.01); *G06F 19/32* (2013.01); *G06F 19/3406* (2013.01); *G06F 19/3418* (2013.01); *G06F 19/3431* (2013.01); *G06F 19/3475* (2013.01); *G06F 19/3481* (2013.01); *G06F 21/32* (2013.01); *G06Q 50/22* (2013.01); *G09B 5/00* (2013.01); *A61B 5/021* (2013.01); *A61B 5/02416* (2013.01); *A63B 2220/803* (2013.01); *A63B 2225/50* (2013.01); *A63B 2230/75* (2013.01); *Y10S 128/92* (2013.01)

(56) References Cited

U.S. PATENT DOCUMENTS

| | | | |
|---|---|---|---|
| 4,301,879 A * | 11/1981 | Dubow .......................... 177/5 |
| 4,312,358 A | 1/1982 | Barney |
| 4,318,447 A * | 3/1982 | Northcutt .................. 177/25.19 |
| 4,366,873 A * | 1/1983 | Levy et al. ................ 177/25.19 |
| 4,367,752 A | 1/1983 | Jimenez et al. |
| 4,423,792 A * | 1/1984 | Cowan ...................... 177/25.19 |
| 4,433,741 A | 2/1984 | Ryckman, Jr. |
| 4,576,244 A * | 3/1986 | Zeigner et al. ............... 177/245 |
| 4,577,710 A * | 3/1986 | Ruzumna ..................... 177/245 |
| 4,578,769 A | 3/1986 | Frederick |
| 4,605,080 A * | 8/1986 | Lemelson ........................ 177/4 |
| 4,757,453 A | 7/1988 | Nasiff |
| 4,773,492 A | 9/1988 | Ruzumna |
| 4,977,509 A | 12/1990 | Pitchford et al. |
| 5,058,427 A | 10/1991 | Brandt |
| 5,224,059 A | 6/1993 | Nitta et al. |
| 5,295,085 A | 3/1994 | Hoffacker |
| 5,323,650 A | 6/1994 | Fullen et al. |
| 5,415,176 A | 5/1995 | Sato et al. |
| 5,583,776 A | 12/1996 | Levi et al. |
| 5,611,351 A | 3/1997 | Sato et al. |
| 5,620,003 A | 4/1997 | Sepponen |
| 5,671,162 A | 9/1997 | Werbin |
| 5,724,265 A | 3/1998 | Hutchings |
| 5,724,267 A | 3/1998 | Richards |
| 5,832,417 A | 11/1998 | Petrucelli et al. |
| 5,886,302 A | 3/1999 | Germanton et al. |
| 5,891,042 A | 4/1999 | Sham et al. |
| 5,899,963 A | 5/1999 | Hutchings |
| 5,947,868 A | 9/1999 | Dugan |
| 5,955,667 A | 9/1999 | Fyfe |
| 5,976,083 A | 11/1999 | Richardson et al. |
| 6,018,705 A | 1/2000 | Gaudet et al. |
| 6,038,465 A | 3/2000 | Melton, Jr. |
| 6,039,688 A * | 3/2000 | Douglas et al. ............... 600/300 |
| 6,145,389 A | 11/2000 | Ebeling et al. |
| 6,183,425 B1 | 2/2001 | Whalen et al. |
| 6,287,262 B1 | 9/2001 | Amano et al. |
| 6,292,690 B1 | 9/2001 | Petrucelli et al. |
| 6,301,964 B1 | 10/2001 | Fyfe et al. |
| 6,305,221 B1 | 10/2001 | Hutchings |
| 6,309,360 B1 | 10/2001 | Mault |
| 6,369,337 B1 | 4/2002 | Machiyama et al. |
| 6,370,425 B1 | 4/2002 | Oguma |
| D460,010 S * | 7/2002 | Robinson ....................... D10/91 |
| 6,473,641 B1 | 10/2002 | Kodama et al. |
| 6,473,643 B2 | 10/2002 | Chai et al. |
| 6,477,409 B2 | 11/2002 | Sakata et al. |
| 6,478,736 B1 | 11/2002 | Mault |
| 6,480,736 B1 | 11/2002 | Kodama et al. |
| 6,487,445 B1 | 11/2002 | Serita et al. |
| RE37,954 E | 1/2003 | Sato et al. |
| 6,513,381 B2 | 2/2003 | Fyfe et al. |
| 6,513,532 B2 | 2/2003 | Mault et al. |
| 6,529,827 B1 | 3/2003 | Beason et al. |
| 6,532,385 B2 | 3/2003 | Serizawa et al. |
| 6,538,215 B2 | 3/2003 | Montagnino et al. |
| 6,552,553 B2 | 4/2003 | Shoji et al. |
| 6,571,200 B1 | 5/2003 | Mault |
| 6,583,369 B2 | 6/2003 | Montagnino et al. |
| 6,612,984 B1 | 9/2003 | Kerr, II |
| 6,621,013 B2 * | 9/2003 | Tanida et al. ..................... 177/4 |
| 6,635,015 B2 | 10/2003 | Sagel |
| 6,678,629 B2 | 1/2004 | Tsuji |
| 6,752,760 B2 * | 6/2004 | Kouou ........................... 600/301 |
| 6,761,064 B2 | 7/2004 | Tsuji |
| 6,790,178 B1 | 9/2004 | Mault et al. |
| 6,813,582 B2 | 11/2004 | Levi et al. |
| 6,856,259 B1 | 2/2005 | Sharp |
| 6,864,436 B1 | 3/2005 | Nobes et al. |
| 6,956,175 B1 | 10/2005 | Daly et al. |
| 6,963,035 B2 * | 11/2005 | Honda et al. ............... 177/25.19 |
| 6,975,961 B1 | 12/2005 | Hong |
| 7,008,350 B1 | 3/2006 | Yamazaki et al. |
| 7,062,225 B2 | 6/2006 | White |
| 7,123,243 B2 | 10/2006 | Kawasaki et al. |
| 7,162,368 B2 | 1/2007 | Levi et al. |
| 7,171,331 B2 | 1/2007 | Vock et al. |
| 7,195,600 B2 | 3/2007 | Ueda et al. |
| 7,200,517 B2 | 4/2007 | Darley et al. |
| 7,261,690 B2 | 8/2007 | Teller et al. |
| 7,283,870 B2 | 10/2007 | Kaiser et al. |
| 7,292,227 B2 | 11/2007 | Fukumoto et al. |
| 7,304,252 B1 | 12/2007 | Hunt et al. |
| 7,357,776 B2 | 4/2008 | Nishibayashi et al. |
| 7,373,820 B1 | 5/2008 | James |
| 7,457,724 B2 | 11/2008 | Vock et al. |
| 7,479,949 B2 | 1/2009 | Jobs et al. |
| 7,505,865 B2 | 3/2009 | Ohkubo et al. |
| 7,523,040 B2 * | 4/2009 | Kirchhoff et al. ................. 705/2 |
| 7,547,851 B1 * | 6/2009 | Wong ......................... 177/25.13 |
| 7,690,556 B1 | 4/2010 | Kahn et al. |
| 7,720,855 B2 * | 5/2010 | Brown ......................... 707/758 |
| 7,774,156 B2 | 8/2010 | Niva et al. |
| 7,789,802 B2 | 9/2010 | Lee et al. |
| 7,831,408 B2 | 11/2010 | Petrucelli |
| 7,865,140 B2 | 1/2011 | Levien et al. |
| 7,872,201 B1 * | 1/2011 | Whitney .................... 177/25.13 |
| 7,907,901 B1 | 3/2011 | Kahn et al. |
| 7,925,022 B2 | 4/2011 | Jung et al. |
| 7,927,253 B2 | 4/2011 | Vincent et al. |
| 7,941,665 B2 | 5/2011 | Berkema et al. |

(56) References Cited

U.S. PATENT DOCUMENTS

| | | | |
|---|---|---|---|
| 7,967,731 B2 | 6/2011 | Kil | |
| 7,983,876 B2 | 7/2011 | Vock et al. | |
| 7,994,439 B2* | 8/2011 | Daniels et al. | 177/25.13 |
| 8,015,030 B2 | 9/2011 | Brown | |
| 8,028,443 B2 | 10/2011 | Case, Jr. | |
| 8,055,469 B2 | 11/2011 | Kulach et al. | |
| 8,059,573 B2 | 11/2011 | Julian et al. | |
| 8,081,168 B2 | 12/2011 | Mamba et al. | |
| 8,095,071 B2 | 1/2012 | Sim et al. | |
| 8,103,247 B2 | 1/2012 | Ananthanarayanan et al. | |
| 8,157,730 B2 | 4/2012 | LeBoeuf et al. | |
| 8,180,591 B2 | 5/2012 | Yuen et al. | |
| 8,190,651 B2 | 5/2012 | Treu et al. | |
| 8,213,613 B2 | 7/2012 | Diehl et al. | |
| 8,260,261 B2 | 9/2012 | Teague | |
| 8,265,901 B2 | 9/2012 | Petrucelli | |
| 8,271,662 B1 | 9/2012 | Gossweiler, III et al. | |
| 8,289,162 B2 | 10/2012 | Mooring et al. | |
| 8,360,936 B2 | 1/2013 | DiBenedetto et al. | |
| 8,457,732 B2* | 6/2013 | Fukada | 600/547 |
| 8,463,577 B2 | 6/2013 | Yuen et al. | |
| 8,475,367 B1 | 7/2013 | Yuen et al. | |
| 8,540,641 B2 | 9/2013 | Kroll et al. | |
| 8,566,120 B2* | 10/2013 | Takehara | 705/3 |
| 8,639,226 B2* | 1/2014 | Hutchings et al. | 455/414.1 |
| 8,653,965 B1 | 2/2014 | Otto et al. | |
| 8,696,569 B2 | 4/2014 | Yuen et al. | |
| 8,719,202 B1 | 5/2014 | Maeng | |
| 8,747,312 B2 | 6/2014 | Yuen et al. | |
| 8,797,281 B2 | 8/2014 | Simmons | |
| 2001/0056229 A1 | 12/2001 | Cosentino et al. | |
| 2002/0022773 A1 | 2/2002 | Drinan et al. | |
| 2002/0027164 A1* | 3/2002 | Mault et al. | 235/462.46 |
| 2002/0055857 A1* | 5/2002 | Mault | 705/2 |
| 2002/0087102 A1 | 7/2002 | Honda et al. | |
| 2002/0107433 A1* | 8/2002 | Mault | 600/300 |
| 2002/0134589 A1 | 9/2002 | Montagnino et al. | |
| 2002/0179338 A1 | 12/2002 | Tanida et al. | |
| 2002/0183051 A1 | 12/2002 | Poor et al. | |
| 2002/0188205 A1 | 12/2002 | Mills | |
| 2002/0198740 A1 | 12/2002 | Roman et al. | |
| 2003/0065257 A1 | 4/2003 | Mault et al. | |
| 2003/0218532 A1 | 11/2003 | Hussmann | |
| 2004/0016437 A1 | 1/2004 | Cobb et al. | |
| 2004/0129463 A1 | 7/2004 | Carlucci et al. | |
| 2004/0193069 A1 | 9/2004 | Takehara | |
| 2004/0238228 A1* | 12/2004 | Montague et al. | 177/25.13 |
| 2005/0006152 A1 | 1/2005 | Eldeiry | |
| 2005/0054938 A1 | 3/2005 | Wehman et al. | |
| 2005/0059902 A1* | 3/2005 | Itagaki | 600/547 |
| 2005/0071197 A1 | 3/2005 | Goldberg | |
| 2005/0107723 A1 | 5/2005 | Wehman et al. | |
| 2005/0113650 A1 | 5/2005 | Pacione et al. | |
| 2005/0176463 A1 | 8/2005 | Hollemans et al. | |
| 2005/0177060 A1 | 8/2005 | Yamazaki et al. | |
| 2005/0181386 A1 | 8/2005 | Diamond et al. | |
| 2005/0228244 A1 | 10/2005 | Banet | |
| 2005/0245494 A1 | 11/2005 | Thompson et al. | |
| 2005/0247494 A1 | 11/2005 | Montagnino | |
| 2005/0283051 A1 | 12/2005 | Chen | |
| 2006/0020177 A1 | 1/2006 | Seo et al. | |
| 2006/0047208 A1 | 3/2006 | Yoon | |
| 2006/0116589 A1 | 6/2006 | Park | |
| 2006/0122470 A1* | 6/2006 | Schulz | 600/300 |
| 2006/0143645 A1 | 6/2006 | Vock et al. | |
| 2006/0173579 A1 | 8/2006 | Desrochers et al. | |
| 2006/0205564 A1* | 9/2006 | Peterson | 482/8 |
| 2006/0217630 A1 | 9/2006 | Ueda et al. | |
| 2006/0241360 A1* | 10/2006 | Montagnino et al. | 600/310 |
| 2006/0247606 A1 | 11/2006 | Batch | |
| 2006/0259323 A1 | 11/2006 | Chan | |
| 2006/0282006 A1 | 12/2006 | Petrucelli | |
| 2007/0010721 A1 | 1/2007 | Chen et al. | |
| 2007/0027401 A1* | 2/2007 | Shimomura et al. | 600/547 |
| 2007/0033069 A1 | 2/2007 | Rao et al. | |
| 2007/0050715 A1 | 3/2007 | Behar | |
| 2007/0051369 A1 | 3/2007 | Choi et al. | |
| 2007/0073178 A1 | 3/2007 | Browning et al. | |
| 2007/0142179 A1 | 6/2007 | Terao et al. | |
| 2007/0142715 A1 | 6/2007 | Banet et al. | |
| 2007/0167286 A1 | 7/2007 | Roes | |
| 2007/0236475 A1 | 10/2007 | Wherry | |
| 2007/0238938 A1 | 10/2007 | Nishibayashi et al. | |
| 2007/0244739 A1 | 10/2007 | Soito et al. | |
| 2008/0039140 A1 | 2/2008 | Morris et al. | |
| 2008/0140338 A1 | 6/2008 | No et al. | |
| 2008/0146277 A1 | 6/2008 | Anglin et al. | |
| 2008/0146961 A1* | 6/2008 | Okura et al. | 600/547 |
| 2008/0154645 A1 | 6/2008 | Takehara | |
| 2008/0155077 A1 | 6/2008 | James | |
| 2008/0174570 A1 | 7/2008 | Jobs et al. | |
| 2008/0183398 A1 | 7/2008 | Petrucelli | |
| 2008/0203144 A1 | 8/2008 | Kim | |
| 2008/0208479 A1 | 8/2008 | Roes | |
| 2008/0221404 A1 | 9/2008 | Tso | |
| 2008/0306767 A1* | 12/2008 | Bodlaender et al. | 705/2 |
| 2008/0314973 A1 | 12/2008 | Zuhars et al. | |
| 2009/0018797 A1 | 1/2009 | Kasama et al. | |
| 2009/0024053 A1* | 1/2009 | Kasahara | 600/547 |
| 2009/0041306 A1 | 2/2009 | Kwong | |
| 2009/0043531 A1 | 2/2009 | Kahn et al. | |
| 2009/0048044 A1 | 2/2009 | Oleson et al. | |
| 2009/0089672 A1 | 4/2009 | Tseng et al. | |
| 2009/0105047 A1 | 4/2009 | Guidi et al. | |
| 2009/0118589 A1 | 5/2009 | Ueshima et al. | |
| 2009/0204422 A1 | 8/2009 | James et al. | |
| 2009/0240113 A1 | 9/2009 | Heckerman | |
| 2010/0007460 A1 | 1/2010 | Hayashi et al. | |
| 2010/0009810 A1 | 1/2010 | Trzecieski | |
| 2010/0043056 A1 | 2/2010 | Ganapathy | |
| 2010/0079291 A1 | 4/2010 | Kroll et al. | |
| 2010/0130831 A1* | 5/2010 | Sato et al. | 600/300 |
| 2010/0227302 A1 | 9/2010 | McGilvery et al. | |
| 2010/0275033 A1 | 10/2010 | Gillespie et al. | |
| 2010/0331145 A1 | 12/2010 | Lakovic et al. | |
| 2010/0331629 A1 | 12/2010 | Sato et al. | |
| 2011/0003665 A1 | 1/2011 | Burton et al. | |
| 2011/0022349 A1 | 1/2011 | Stirling et al. | |
| 2011/0032105 A1 | 2/2011 | Hoffman et al. | |
| 2011/0050394 A1 | 3/2011 | Zhang et al. | |
| 2011/0068931 A1 | 3/2011 | Abernethy et al. | |
| 2011/0087137 A1 | 4/2011 | Hanoun | |
| 2011/0087438 A1 | 4/2011 | Maeir et al. | |
| 2011/0106449 A1 | 5/2011 | Chowdhary et al. | |
| 2011/0109540 A1 | 5/2011 | Milne et al. | |
| 2011/0131005 A1 | 6/2011 | Ueshima et al. | |
| 2011/0143322 A1* | 6/2011 | Tsang | 434/127 |
| 2011/0165998 A1 | 7/2011 | Lau et al. | |
| 2011/0166628 A1 | 7/2011 | Jain | |
| 2011/0184247 A1* | 7/2011 | Contant et al. | 600/300 |
| 2011/0191158 A1 | 8/2011 | Kateraas et al. | |
| 2011/0196617 A1 | 8/2011 | Petrucelli | |
| 2011/0197157 A1 | 8/2011 | Hoffman et al. | |
| 2012/0033807 A1 | 2/2012 | Asim et al. | |
| 2012/0059911 A1 | 3/2012 | Randhawa et al. | |
| 2012/0072165 A1 | 3/2012 | Jallon | |
| 2012/0083715 A1 | 4/2012 | Yuen et al. | |
| 2012/0109676 A1 | 5/2012 | Landau | |
| 2012/0150074 A1 | 6/2012 | Yanev et al. | |
| 2012/0150483 A1 | 6/2012 | Vock et al. | |
| 2012/0221634 A1 | 8/2012 | Treu et al. | |
| 2012/0226111 A1 | 9/2012 | LeBoeuf et al. | |
| 2012/0239173 A1 | 9/2012 | Laikari et al. | |
| 2012/0254987 A1 | 10/2012 | Ge et al. | |
| 2012/0274508 A1 | 11/2012 | Brown et al. | |
| 2012/0297229 A1 | 11/2012 | Desai et al. | |
| 2012/0297440 A1 | 11/2012 | Reams et al. | |
| 2013/0106684 A1 | 5/2013 | Weast et al. | |
| 2013/0289889 A1 | 10/2013 | Yuen et al. | |
| 2014/0012512 A1 | 1/2014 | Yuen et al. | |
| 2014/0018706 A1 | 1/2014 | Yuen et al. | |
| 2014/0095208 A1 | 4/2014 | Goldberg | |
| 2014/0099614 A1 | 4/2014 | Hu et al. | |
| 2014/0182952 A1 | 7/2014 | Yuen et al. | |

(56) References Cited

U.S. PATENT DOCUMENTS

| | | | |
|---|---|---|---|
| 2014/0257709 A1 | 9/2014 | Yuen et al. |
| 2014/0343443 A1 | 11/2014 | Yuen et al. |
| 2014/0371887 A1 | 12/2014 | Hoffman et al. |
| 2014/0377729 A1 | 12/2014 | Yuen et al. |
| 2014/0379275 A1 | 12/2014 | Yuen et al. |
| 2015/0011845 A1 | 1/2015 | Yuen et al. |
| 2015/0018991 A1 | 1/2015 | Arnold et al. |

FOREIGN PATENT DOCUMENTS

| | | |
|---|---|---|
| JP | 11-347021 | 12/1999 |
| WO | WO 02/28123 A1 | 4/2002 |
| WO | WO 02/084568 A1 | 10/2002 |
| WO | WO 2007/102708 A1 | 9/2007 |
| WO | WO 2010/001318 A1 | 1/2010 |

OTHER PUBLICATIONS

US Office Action, dated Sep. 26, 2012, issued in U.S. Appl. No. 13/346,275.
US Final Office Action, dated Feb. 4, 2013, issued in U.S. Appl. No. 13/346,275.
US Notice of Allowance, dated Mar. 7, 2013, issued in U.S. Appl. No. 13/346,275.
US Office Action, dated Oct. 9, 2013, issued in U.S. Appl. No. 13/929,868.
US Notice of Allowance, dated Feb. 5, 2014, issued in U.S. Appl. No. 13/929,868.
US Office Action, dated Dec. 3, 2013, issued in U.S. Appl. No. 14/027,164.
US Notice of Allowance, dated Apr. 9, 2014, issued in U.S. Appl. No. 14/027,164.
US Office Action, dated Dec. 18, 2013, issued in U.S. Appl. No. 14/027,166.
US Final Office Action, dated Apr. 30, 2014, issued in U.S. Appl. No. 14/027,166.
"Activator is One of the Best Cydia iPhone Hacks | Control your iPhone with Gestures," iphone-tips-and-advice.com, [retrieved on Jul. 9, 2013 at http://www.iphone-tips-and-advice.com/activatior. html], 10 pp.
Antoniou, Z, et al., "Intuitive mobile user interaction in smart spaces via NFC-enhanced devices," Proceedings of the Third International Conference on Wireless and Mobile Communications (ICWMC'07), pp. 1-6.
Chudnow, Alan (Dec. 3, 2012) "Basis Wristband Make Its Debut," The Wired Self, Living in a Wired World, published in Health [retrieved on Jul. 22, 2013 at http://thewiredself.com/health/basis-wrist-band-make-its-debut/], 3pp.
Clifford et al., (Nov. 2006) "Altimeter and Barometer System," Freescale Semiconductor Application Note AN1979, Rev 3, pp. 1-10.
DesMarais, Christina (posted on Sep. 3, 2013) "Which New Activity Tracker is Best for You?" Health and Home, Health & Fitness , Guides & Reviews, [Retrieved on Sep. 23, 2013 at http://www.techlicious.com/guide/which-new-activity-tracker-is-right-for-you/] 4 pp.
Empson, Rip, (Sep. 22, 2011) "Basis Reveals an Awesome New Affordable Heart and Health Tracker You Can Wear on Your Wrist," [retrieved on Sep. 23, 2013 at http://techcrunch.com/2011/09/22/basis-reveals-an-awesome-new . . . ], 3 pp.
Fang et al., (Dec. 2005) "Design of a Wireless Assisted Pedestrian Dead Reckoning System—The NavMote Experience," IEEE Transactions on Instrumentation and Measurement, 54(6):2342-2358.
Fitbit User's Manual, Last Updated Oct. 22, 2009, 15 pages.
Forerunner® 201 personal trainer owner's manual, (Feb. 2006) Garmin Ltd., 48 pp.
Forerunner® 301 personal trainer owner's manual, (Feb. 2006) Garmin Ltd., 66 pp.
Forerunner® 50 with ANT+Sport™ wireless technology, Owner's Manual, (Nov. 2007) Garmin Ltd., 44 pp.
Forerunner® 205/305 Owner's Manual, GPS-enabled trainer for runners, (2006-2008), Garmin Ltd., 80 pp.
Forerunner® 405CX Owner's Manual, "GPS-Enabled Sports Watch Sync," (Mar. 2009), Garmin Ltd., 56 pp.
Forerunner® 110 Owner's Manual, (2010) "GPS-Enabled Sport Watch," Garmin Ltd., 16 pp.
Forerunner® 210 Owner's Manual, (2010) "GPS-Enabled Sport Watch," Garmin Ltd., 28 pp.
Forerunner® 410 Owner's Manual, (Jul. 2012) "GPS-Enabled Sport Watch With Wireless Sync," Garmin Ltd., 52 pp.
Forerunner® 10 Owner's Manual (Aug. 2012), Garmin Ltd., 10 pp.
Forerunner® 310XT Owner's Manual, Multisport GPS Training Device, (2009-2013), Garmin Ltd., 56 pp.
Forerunner® 405 Owner's Manual, (Mar. 2011) "GPS-Enabled Sport Watch With Wireless Sync," Garmin Ltd., 56 pp.
Forerunner® 910XT Owner's Manual, (Jan. 2013) Garmin Ltd., 56 pp.
Garmin Swim™ Owner's Manual (Jun. 2012), 12 pp.
Godfrey et al., (2008) "Direct measurement of human movement by accelerometry," Medical Engineering & Physics, 30:1364-1386.
Godha et al., (May 2008) "Foot mounted inertial system for pedestrian navigation," Measurement Science and Technology, 19(7):1-9.
Gonzalez-Landaeta et al. (Jul. 2008) "Heart rate detection from an electronic weighing scale," Physiological Measurement, 29(8):979.
Inan et al., (Mar. 2010) "Adaptive cancellation of Floor vibrations in standing ballistocardiogram measurements using a seismic sensor as a noise reference," IEEE Trans. on Biomedical Engineering, 57(3):722-727.
Ladetto et al., (Sep. 2000) "On Foot Navigation: When GPS alone is not enough," Journal of Navigation, 53(2):279-285.
Lammel et al., (Sep. 2009) "Indoor Navigation with MEMS sensors," Proceedings of the Eurosensors XXIII conference, 1(1):532-535.
Larklife, User Manual, (2012) Lark Technologies, 7 pp.
Lark/Larkpro, User Manual, (2012) "What's in the box," Lark Technologies, 7 pp.
Lester et al., (2005) "A Hybrid Discriminative/Generative Approach for Modeling Human Activities," Proc. of the Int'l Joint Conf. Artificial Intelligence, pp. 766-772.
Lester et al., (2009) "Validated caloric expenditure estimation using a single body-worn sensor," Proc. of the Int'l Conf. on Ubiquitous Computing, pp. 225-234.
Nike+ FuelBand GPS Manual, User's Guide (Product Release Date Unknown, downloaded Jul. 22, 2013), 26 pages.
Nike+SportBand User's Guide, (Product Release Date Unknown, downloaded Jul. 22, 2013), 36 pages.
Nike+SportWatch GPSs Manual, User's Guide, Powered by TOMTOM, (Product Release Date Unknown, downloaded Jul. 22, 2013), 42 pages.
Ohtaki et al. (Aug. 2005) "Automatic classification of ambulatory movements and evaluation of energy consumptions utilizing accelerometers and a barometer," Microsystem Technologies, 1(8-10):1034-1040.
Pärkkä et al., (Jan. 2006) "Activity Classification Using Realistic Data From Wearable Sensors," IEEE Transactions on Information Technology in Biomedicine, 10(1):119-128.
Pärkkä, J. et al., (2000) "A wireless wellness monitor for personal weight management," IEEE, pp. 83-88.
"Parts of Your Band," (Product Release Date Unknown, downloaded Jul. 22, 2013) Jawbone UP Band, 1 page.
Perrin et al., (2000) "Improvement of walking speed prediction by accelerometry and altimetry, validated by satellite positioning," Perrin, et al, Medical & Biological Engineering & Computing, 38:164-168.
Polar WearLink® + Coded Transmitter 31 Coded Transmitter W.I.N.D. User Manual, Polar® Listen to Your Body, Manufactured by Polar Electro Oy, 11 pages.
Rainmaker, (Jun. 25, 2012, updated Feb. 16, 2013) "Garmin Swim watch In-Depth Review," [retrieved on Sep. 9, 2013 at http://www.dcrainmaker.com/2012/06/garmin-swim-in-depth-review.html, 38 pp.
Retscher (2006) "An Intelligent Multi-sensor System for Pedestrian Navigation," Journal of Global Positioning Systems, 5(1):110-118.

(56) References Cited

OTHER PUBLICATIONS

Sagawa et al. (Aug.-Sep. 1998) "Classification of Human Moving Patterns Using Air Pressure and Acceleration," Proceedings of the 24th Annual Conference of the IEEE Industrial Electronics Society, 2:1214-1219.
Sagawa et al. (Oct. 2000) "Non-restricted measurement of walking distance," IEEE Int'l Conf. on Systems, Man, and Cybernetics, 3:1847-1852.
"SCP1000-D01/D11 Pressure Sensor as Barometer and Altimeter," VTI Technologies, Jun. 2006, Application Note 33, 3 pages.
Stirling et al., (2005) "Evaluation of a New Method of Heading Estimation for Pedestrian Dead Reckoning Using Shoe Mounted Sensors," Journal of Navigation, 58:31-45.
"Suunto Lumi User Guide," Suunto Oy, Jun. and Sep. 1997, 49 pages.
Tanigawa et al., (Mar. 2008) "Drift-free dynamic height sensor using MEMS IMU aided by MEMS pressure sensor," Workshop on Positioning, Navigation and Communication, pp. 191-196.
"Tanita Ironman InnerScan body Composition Monitor," Tanita Corporation, Model MC-554 Manual, 2005.
"Using MS5534 for altimeters and barometers," Intersema App., Note AN501, Jan. 2006, 12 pp.
U.S. Appl. No. 14/476,128, filed Sep. 3, 2014, Yuen et al.
U.S. Appl. No. 14/476,143, filed Sep. 3, 2014, Yuen et al.
U.S. Appl. No. 14/493,156, filed Sep. 22, 2014, Yuen et al.
U.S. Appl. No. 14/497,177, filed Sep. 25, 2014, Arnold et al.
US Office Action, dated Oct. 16, 2014, issued in U.S. Appl. No. 14/201,467.
US Office Action, dated Sep. 25, 2014, issued in U.S. Appl. No. 14/201,478.
US Office Action, dated Dec. 19, 2014, issued in U.S. Appl. No. 14/476,128.
US Office Action, dated Dec. 17, 2014, issued in U.S. Appl. No. 14/476,143.
US Office Action, dated Dec. 3, 2014, issued in U.S. Appl. No. 14/448,965.
US Final Office Action, dated Feb. 10, 2015, issued in U.S. Appl. No. 14/201,467.
US Office Action, dated Mar. 5, 2015, issued in U.S. Appl. No. 14/493,156.
US Final Office Action, dated Feb. 11, 2015, issued in U.S. Appl. No. 14/201,478.
US Office Action, dated Feb. 24, 2015, issued in U.S. Appl. No. 14/027,166.
US Office Action, dated May 21, 2015, issued in U.S. Appl. No. 14/497,177.
US Notice of Allowance, dated May 6, 2015, issued in U.S. Appl. No. 14/201,478.
US Notice of Allowance, dated May 7, 2015, issued in U.S. Appl. No. 14/476,128.
US Final Office Action, dated Apr. 8, 2015, issued in U.S. Appl. No. 14/476,143.
US Notice of Allowance, dated Apr. 15, 2015, issued in U.S. Appl. No. 14/448,965.
Linde et al., (2005) "Self-Weighing in Weight Gain Prevention and Weight Loss Trials," Annals of Behavioral Medicine, 30(3):210-216.

\* cited by examiner

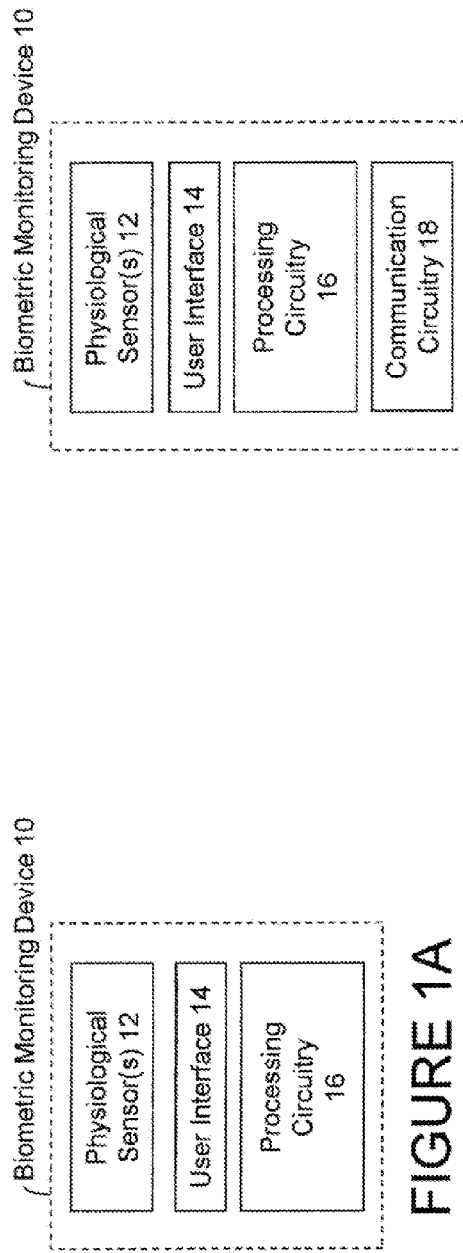
FIGURE 1A
FIGURE 1B
FIGURE 1C
FIGURE 1D

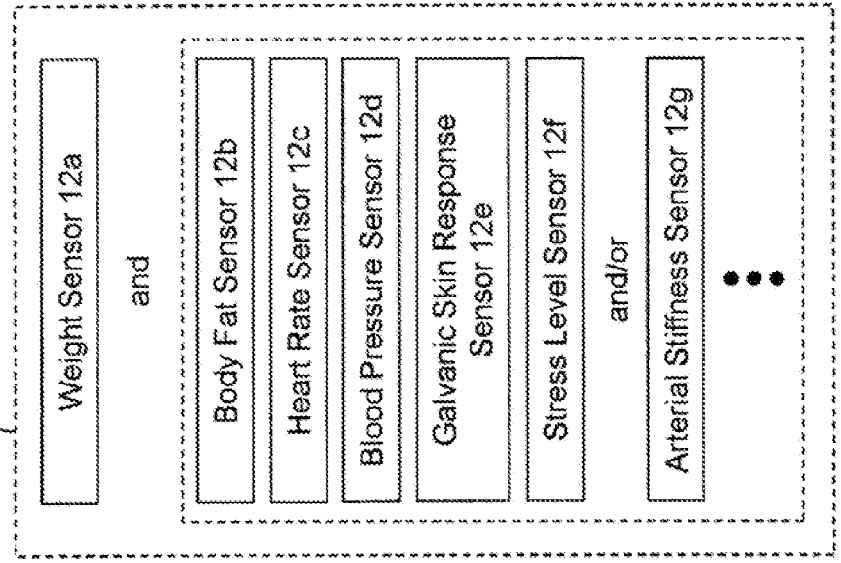
FIGURE 2C
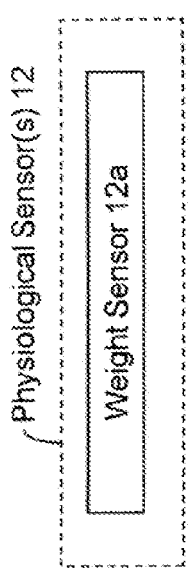
FIGURE 2A
FIGURE 2B

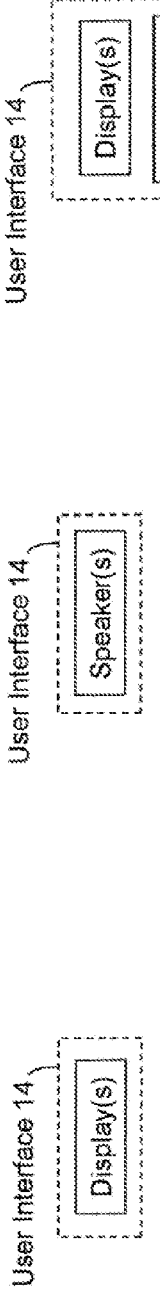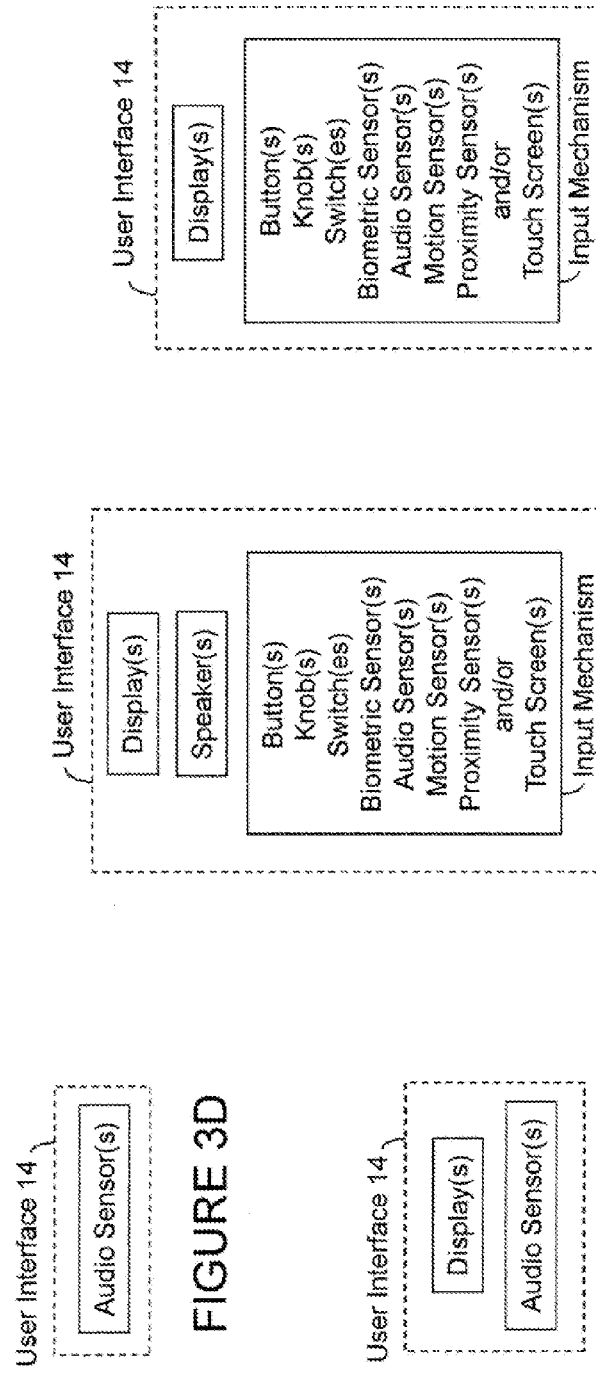

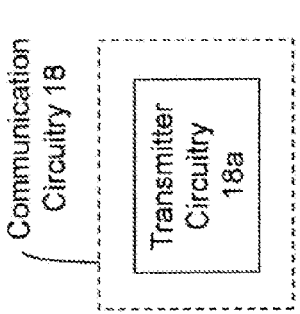
FIGURE 5A
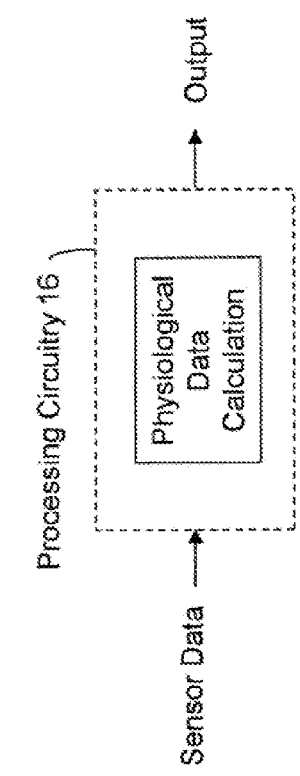
FIGURE 4
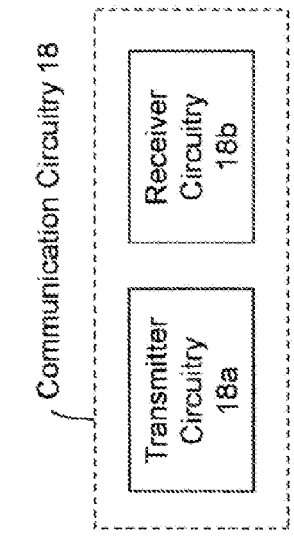
FIGURE 5C
FIGURE 5B

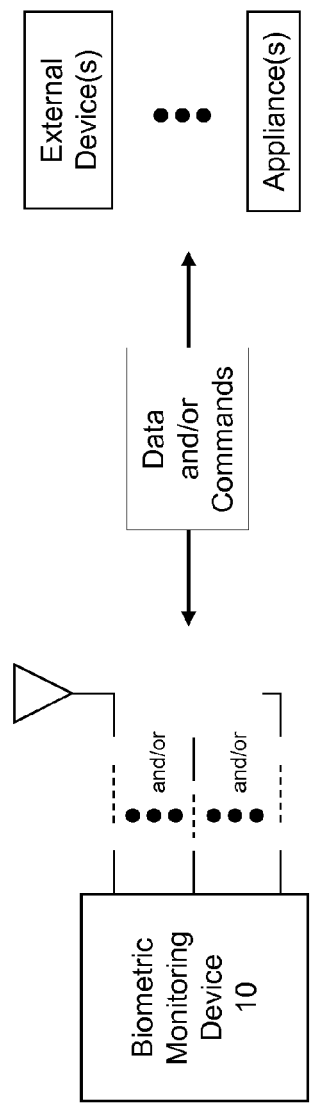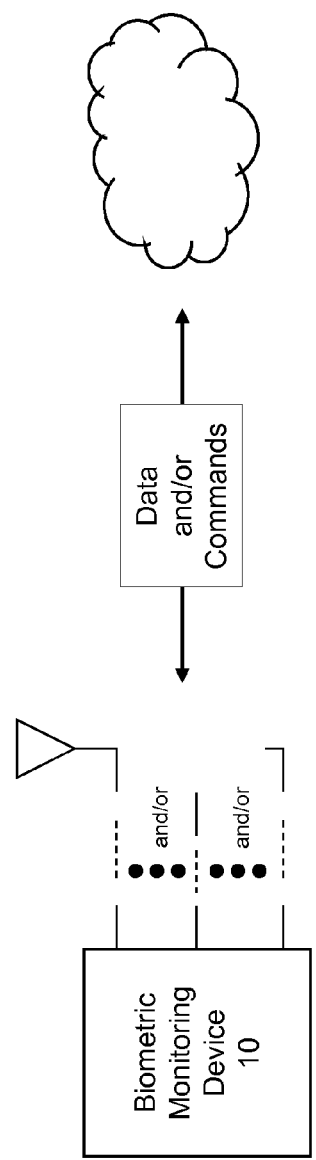

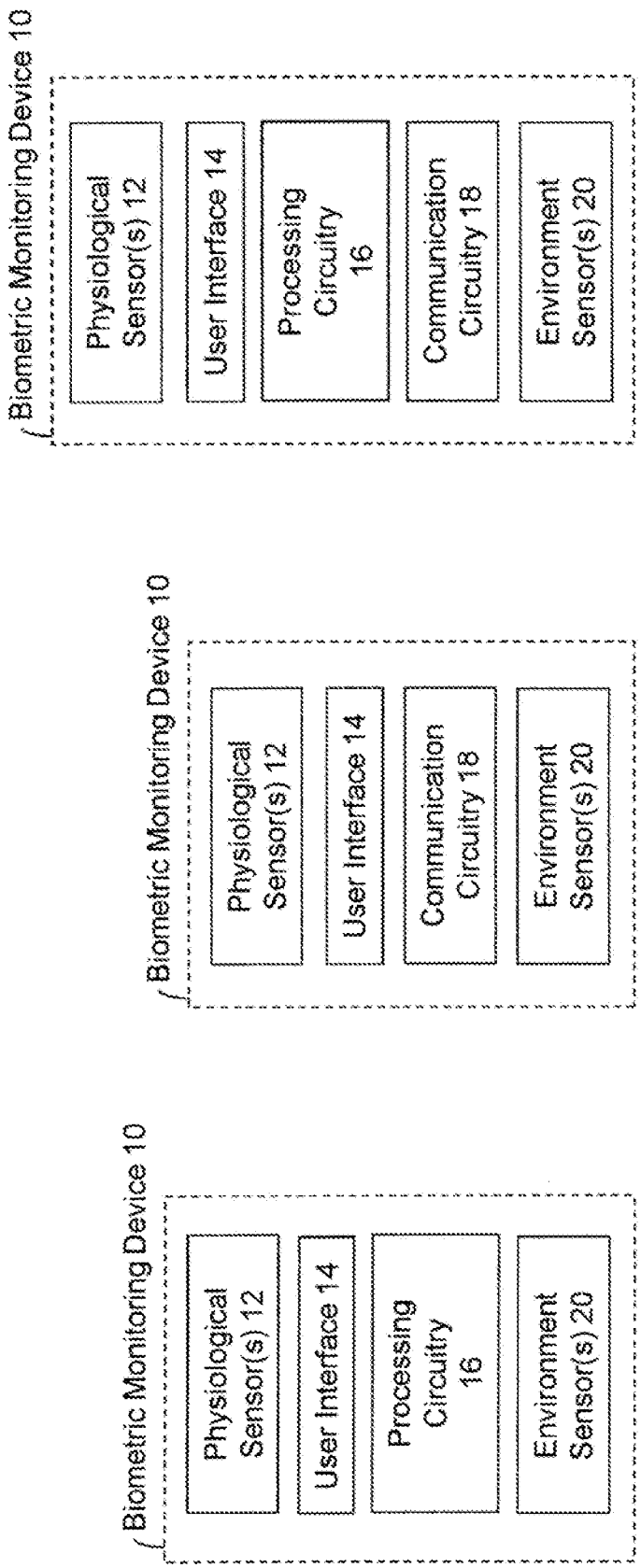

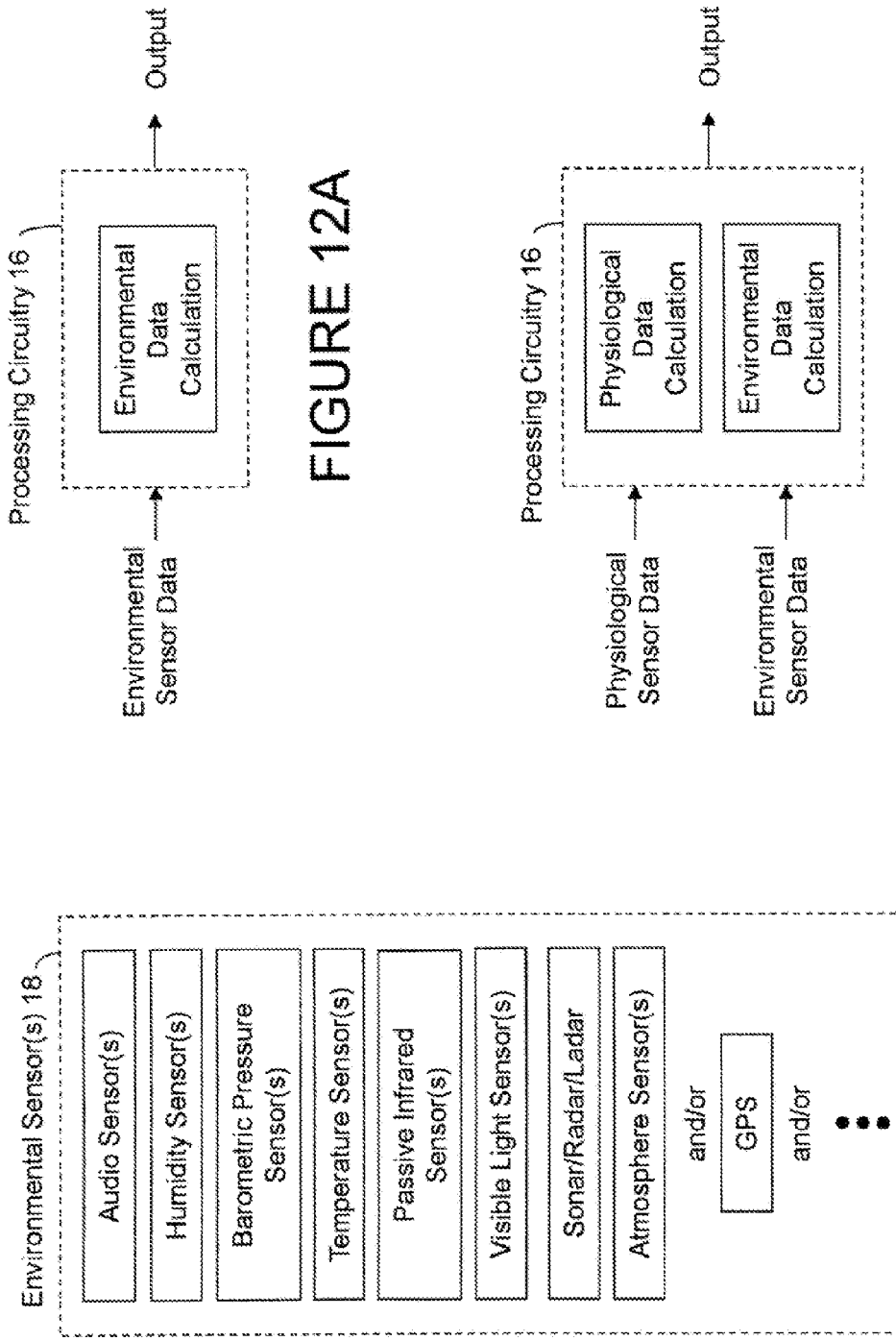

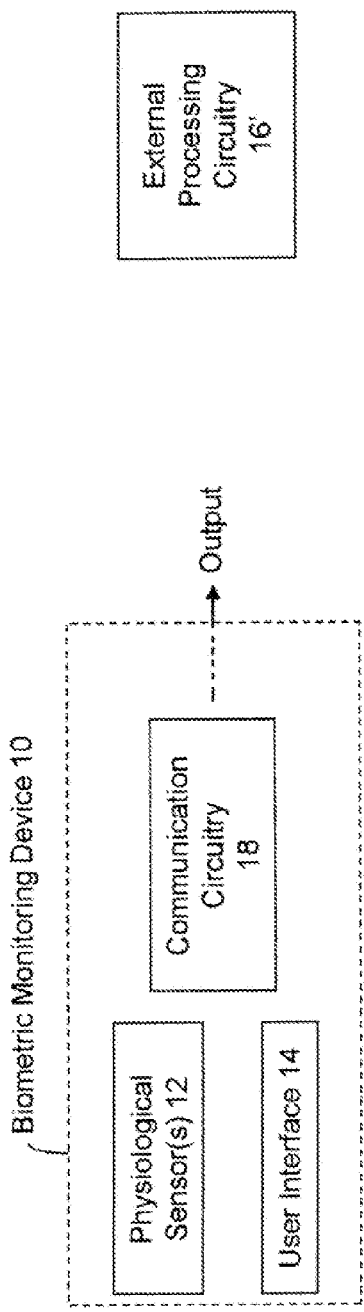
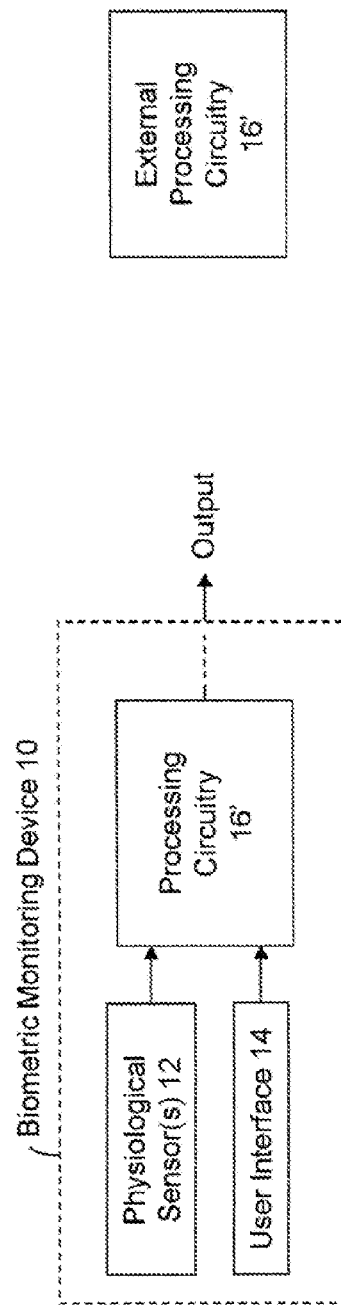

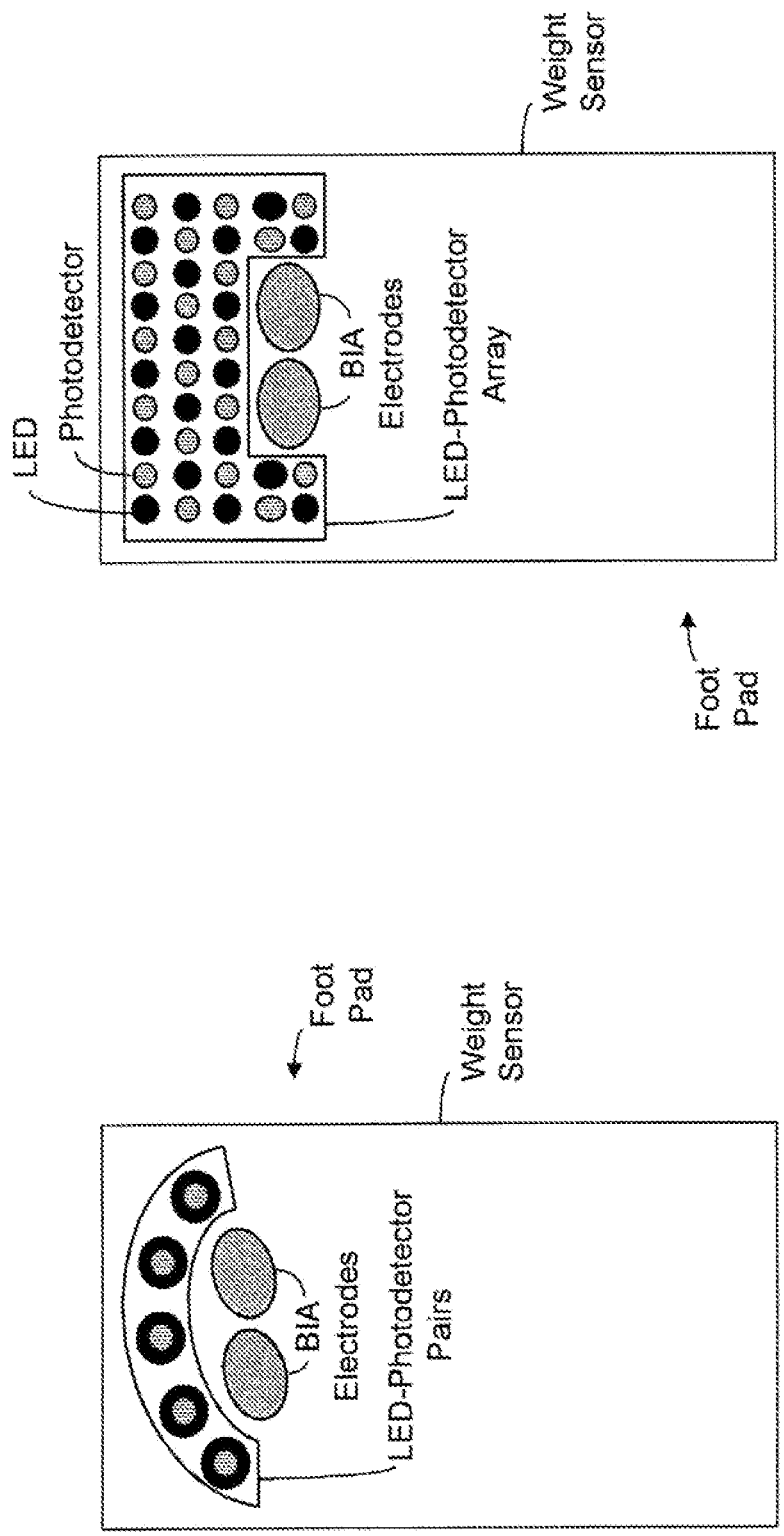

BIOMETRIC MONITORING DEVICE HAVING A BODY WEIGHT SENSOR, AND METHODS OF OPERATING SAME

RELATED APPLICATIONS

This application is a continuation of U.S. patent application Ser. No. 14/027,164, filed Sep. 14, 2013, which is itself a divisional of U.S. patent application Ser. No. 13/929,868, filed Jun. 28, 2013 and which issued as U.S. Pat. No. 8,696,569 on Apr. 15, 2014, which is itself a divisional of U.S. patent application Ser. No. 13/346,275, filed Jan. 9, 2012 and which issued as U.S. Pat. No. 8,475,367 on Jul. 2, 2013, which itself claims benefit under 35 U.S.C. §119(e) to U.S. Provisional Application No. 61/431,020, filed Jan. 9, 2011, titled "BIOMETRIC MONITORING DEVICE HAVING A BODY WEIGHT SENSOR, AND METHODS OF OPERATING SAME," all of which are hereby incorporated by reference herein in their entireties.

INTRODUCTION

The present inventions relate to a biometric monitoring device to calculate, measure, assess and/or determine physiologic data using data from one or more sensors including a personal weight sensor or scale, to measure the weight of a user. The biometric monitoring device of the present inventions further includes a user interface to input data/commands and display physiologic information including, for example, current information, historical information and/or current information in view of historical information. Notably, the biometric monitoring device may also include one or more additional sensors to sense, measure and/or detect other physiologic data, for example, data which is representative of body fat, fat-free mass, hydration, body cell mass, height, eye color, sun exposure, heart rate, respiratory rate, blood pressure and/or arterial stiffness.

The biometric monitoring device of the present inventions may include communication circuitry (wireless and/or wired) to transmit biometric or physiologic data and/or receive, for display via the user interface, web content, news, traffic, weather, social content (for example, instant messaging), advertisement, emails, calendar schedule, exercise or diet coaching, instructions and/or data, and goal oriented information (for example, a user's progress toward biometric or physiological goals (weight, body fat composition, caloric consumption, activity and/or sleep)) as well as biometric or physiologic information including, for example, current information, historical information and/or current information in view of historical information.

The historical information or data may include, for example, historical weight and/or body fat data measured by the monitoring device (which may be stored internally to and/or externally from the biometric monitoring device), historical user activity data, food consumption data, and/or sleep data (which may be measured or monitored by other personal and/or portable devices (for example, Fitbit's activity monitoring/tracking device and acquired by the biometric monitoring device), historical user biometric or physiologic data (for example, heart rate, blood pressure, arterial stiffness, blood glucose levels, cholesterol, duration of TV watching, duration of video game play and/or mood). Notably, such historical data may be presented in graphical and/or textual form.

The communication circuitry of the biometric monitoring device of the present inventions may facilitate or provide external connectivity to, for example, the Internet and/or local external devices and/or appliances. In certain embodiments, the biometric monitoring device may operate, program and/or control such local external devices and/or appliances.

In certain aspects, the biometric monitoring device includes processing circuitry to calculate physiologic data using data from one or more physiological sensors of the biometric monitoring device. For example, processing circuitry in the monitoring device may employ the biometric or physiologic data to calculate, measure, assess and/or determine the user's weight, body fat, fat-free mass, hydration (total body water, extracellular water, and intracellular water), body cell mass, heart rate, respiratory rate, blood pressure, height, eye color, sun exposure and/or arterial stiffness. The processing circuitry may employ any technique now known or later developed to calculate such biometric or physiologic information. Notably, the processing circuitry may be partially or wholly disposed external to the biometric monitoring device wherein the external processing circuitry receives processed, partially processed and/or "raw" sensor data. Here, the external processing circuitry partially or wholly calculates, assesses and/or determines certain physiologic data of the user via the processes, partially processed and/or "raw" sensor data.

In another aspect of the present inventions, the biometric monitoring device (for example, as described above) may also include one or more environmental sensors to detect, measure and/or sense ambient environmental conditions. For example, the environmental sensors may detect, measure and/or sense ambient pressure, temperature, sound, light, humidity, location and/or atmosphere. In response thereto, the biometric monitoring device of this aspect of the inventions, in addition to monitoring, calculating, determining and/or sensing physiologic data of a user, may provide status information to the user and/or control or operate such local external devices and/or appliances in accordance with, for example, predetermined instructions In yet another aspect of the present inventions, the biometric monitoring device (for example, as described above) may include communication circuitry to receive and store and/or communicate/forward (for example, to local or remote data storage) activity and/or environmental data from one or more other monitoring devices that may be portable (for example, a device affixed to the user) or stationary (for example, a household appliance or fixture). Here, the other monitoring devices may include one or more activity sensors (e.g., to detect the activity of the user) and/or environmental sensors to detect, measure and/or sense ambient environmental conditions. For example, the environmental sensors of the other monitoring devices may detect, measure and/or sense ambient pressure, temperature, sound, light, humidity, location and/or atmosphere. In response thereto, the biometric monitoring device of this aspect of the inventions, in addition to monitoring, calculating, determining and/or sensing physiologic data of a user, may store (for example, in one or more resident storage devices), and/or process data received from the other monitoring devices, and/or upload such data (whether or not processed) to one or more local or remote data storage devices (for example, via a local area network ("LAN"), wide area network ("WAN") or the Internet).

The biometric monitoring device may also transmit user identification data to correlate the physiologic data and/or activity data with a particular user or particular device (external monitoring device and/or biometric device). Here, the user identification data, or the like, is any data that identifies a particular user, a particular device and/or from which a particular user and/or device may be determined. For example, the user identification data may be data associated with a particular user (for example, a particular value, character, number, combination thereof, and/or sequence thereof) and/or a particular device (for example, a particular value, character, number, combination thereof, and/or sequence thereof). Indeed, in one embodiment, the biometric monitoring device may be paired with one or more external monitoring devices (for example, one or more portable activity monitoring devices) and receipt of data therefrom may be "assumed", inferred or presumed to be associated with a user and/or external device.

Notably, the user identification data may be data separate from the physiologic, activity and/or environmental data and/or may be incorporated or integrated in the physiologic, activity and/or environmental data. Moreover, the user identification data may be implied or inferred from the communication with an external device (for example, portable activity monitoring device and/or biometric device) and/or implied or inferred from other data (for example, the physiologic data from a biometric monitoring device and/or activity data or physiologic data from a portable activity monitoring device and/or biometric device). Indeed, the user identification data may be determined automatically (via data transfer using the communication circuitry) or manually (via user input using the user interface). As such, in one embodiment, the biometric monitoring device may automatically obtain the user identification data to provide/acquire data which is representative of particular details of the user (for example, height, weight, gender and/or age) from data storage (for example, resident, local and/or remote data storage). Such details may be employed by the processing circuitry to determine or calculate physiologic data (for example, body fat and lean muscle mass).

In addition to receiving, storing and/or transmitting physiologic, activity data and/or environment data (for example, from one or more external devices), the biometric monitoring device may provide status information to the user and/or control or operate such local external devices and/or appliances in accordance with, for example, predetermined instructions based on or in response to the activity and/or environmental data received from the other monitoring devices and/or the external devices itself.

BRIEF DESCRIPTION OF THE DRAWINGS

In the course of the detailed description to follow, reference will be made to the attached drawings. These drawings show different aspects of the present inventions and, where appropriate, reference numerals illustrating like structures, components, materials and/or elements in different figures are labeled similarly. It is understood that various combinations of the structures, components, and/or elements, other than those specifically shown, are contemplated and are within the scope of the present inventions.

Moreover, there are many inventions described and illustrated herein. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, certain permutations and combinations are not discussed and/or illustrated separately herein.

FIGS. 1A-1D are block diagram representations of exemplary biometric monitoring devices, according to at least certain aspects of certain embodiments of the present inventions, wherein the biometric monitoring devices, according to at least certain aspects of certain embodiments of the present inventions, includes one or more physiological sensors (for example, a weight sensor/scale) and user interface, and, in certain embodiments, may also include processing circuitry and/or communication circuitry;

FIG. 2A is a block diagram representation of an exemplary physiological sensor including a weight sensor according to at least certain aspects of certain embodiments of the present inventions;

FIGS. 2B and 2C are block diagram representations of exemplary physiological sensors including a weight sensor and a body fat sensor, heart rate sensor, blood pressure sensor, galvanic skin sensor, stress level sensor and/or arterial stiffness sensor according to at least certain aspects of certain embodiments of the present inventions;

FIGS. 3A-3G are block diagram representations of exemplary user interfaces that may be incorporated in the exemplary biometric monitoring devices according to at least certain embodiments of the present inventions;

FIG. 4 is a block diagram representation of exemplary processing circuitry to calculate, assess and/or determine physiologic information of the user based on data from one or more physiological sensors; the processing circuitry may include memory (for example, Flash memory, DRAM and/or SRAM) to store, for example, (i) sensor data and (ii) information which is representative of the user's weight, percentage body fat, heart rate, blood pressure, arterial stiffness—for example, instantaneous, cumulative and/or over time (historically based data); notably, the processing circuitry may be discrete or integrated logic, and/or one or more state machines, processors/controllers (suitably programmed) and/or field programmable gate arrays (or combinations thereof); indeed, any circuitry (for example, discrete or integrated logic, state machine(s), processor(s)/controller(s) (suitably programmed) and/or field programmable gate array(s) (or combinations thereof)) now known or later developed may be employed to calculate, determine, assess and/or determine the physiologic information of the user based on sensor data;

FIGS. 5A-5C are block diagram representations of communication circuitry that may be incorporated in the exemplary biometric monitoring devices according to at least certain embodiments of the present inventions; notably, the communication circuitry may implement or employ any form of communications (for example, wireless, optical, or wired) and/or protocol (for example, standard or proprietary) now known or later developed, all forms of communications and protocols are intended to fall within the scope of the present inventions (for example, Bluetooth, ANT, WLAN, Wi-Fi, power-line networking, all types and forms of Internet based communications, and/or SMS);

FIG. 6A is a block diagram representation of an exemplary biometric monitoring device, according to one or more of the embodiments described and/or illustrated herein, in communication with one or more external devices and/or appliances, according to at least certain embodiments of the present inventions;

FIG. 6B is a block diagram representation of an exemplary biometric monitoring device, according to one or more of the embodiments described and/or illustrated herein, in communication with the Internet, according to at least certain embodiments of the present inventions;

FIGS. 10A-10C are block diagram representations of exemplary biometric monitoring devices having one or more environment sensors, according to at least certain aspects of certain embodiments of the present inventions, wherein the biometric monitoring devices, according to at least certain aspects of certain embodiments of the present inventions, includes one or more physiological sensors (for example, a weight sensor/scale) and user interface, and, in certain embodiments, may also include processing circuitry and/or communication circuitry;

FIG. 11 is a block diagram representation of one or more exemplary environmental sensors according to at least certain aspects of certain embodiments of the present inventions;

FIG. 12A is a block diagram representation of exemplary processing circuitry to calculate, assess and/or determine ambient environment data based on data from one or more environmental sensors; the processing circuitry may include memory (for example, Flash memory, DRAM and/or SRAM) to store, for example, (i) sensor data and (ii) information which is representative of the ambient environment—for example, instantaneous, cumulative and/or over time (historically based data); notably, the processing circuitry may be discrete or integrated logic, and/or one or more state machines, processors/controllers (suitably programmed) and/or field programmable gate arrays (or combinations thereof); indeed, any circuitry (for example, discrete or integrated logic, state machine(s), processor(s)/controller(s) (suitably programmed) and/or field programmable gate array(s) (or combinations thereof)) now known or later developed may be employed to calculate, determine, assess and/or determine ambient environment information based on environmental sensor data;

FIG. 12B is a block diagram representation of exemplary processing circuitry to calculate, assess and/or determine physiologic information of the user based on data from one or more physiological sensors (like that illustrated in FIG. 5) and ambient environment data from one or more environmental sensors (like that illustrated in FIG. 12A);

FIG. 13A is a block diagram representation of an exemplary biometric monitoring device, according to at least certain aspects of certain embodiments of the present inventions, wherein the processing circuitry which calculates or determines physiologic information of the user based on or using sensor data of the biometric monitoring device is external to the biometric monitoring device;

FIG. 13B is a block diagram representation of an exemplary biometric monitoring device, according to at least certain aspects of certain embodiments of the present inventions, wherein the biometric monitoring device includes certain processing circuitry and certain other processing circuitry is external to the biometric monitoring devices—wherein the internal and external processing circuitry, in combination, calculates or determines physiologic information of the user based on or using sensor data of the biometric monitoring device;

FIGS. 15A-15D are exemplary configurations of physiological sensor layouts of exemplary foot pads of an exemplary biometric monitoring device (for example, illustrated in FIG. 14) having a plurality of physiological sensors including a weight sensor, one or more LED-photo detector pairs and one or more bioelectrical impedance analysis (BIA) electrodes;

Figure 6C:
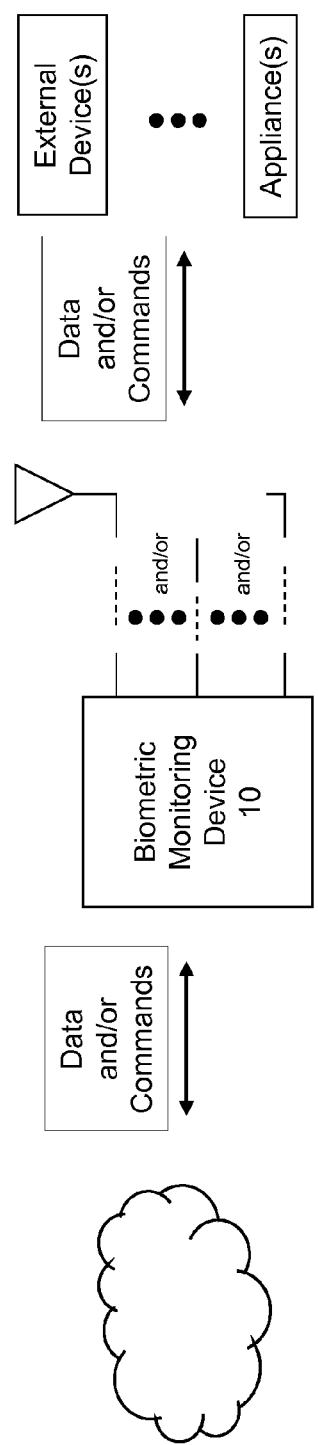
FIG. 6C is a block diagram representation of an exemplary biometric monitoring device, according to one or more of the embodiments described and/or illustrated herein, in communication with (i) one or more external devices and/or appliances and (ii) the Internet, according to at least certain embodiments of the present inventions, wherein in this illustrative embodiment, the exemplary biometric monitoring device is a communications hub between the one or more external devices and/or appliances and the Internet.
Figure 6D:
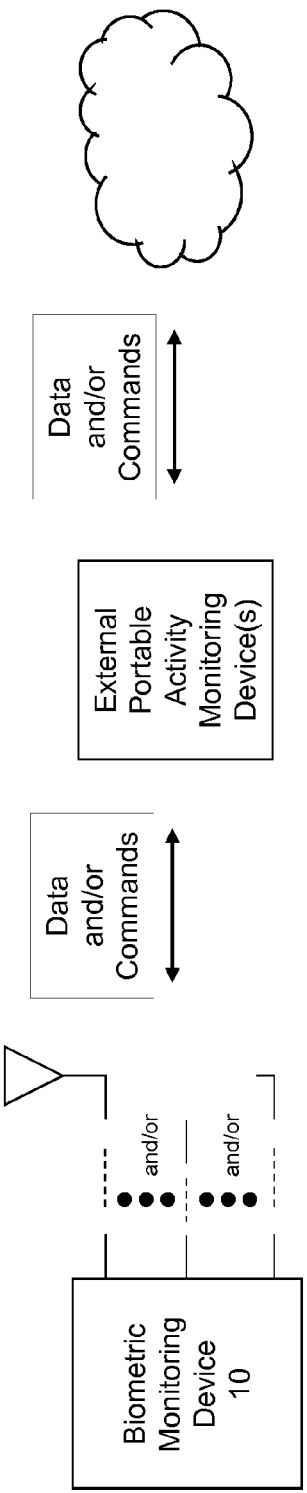
FIG. 6D is a block diagram representation of an exemplary external portable monitoring device(s), according to one or more of the embodiments described and/or illustrated herein, in communication with (i) biometric monitoring device and (ii) the Internet, according to at least certain embodiments of the present inventions, wherein in this illustrative embodiment, the exemplary external portable monitoring is a communications hub between the biometric monitoring device and the Internet.
Figure 7A:
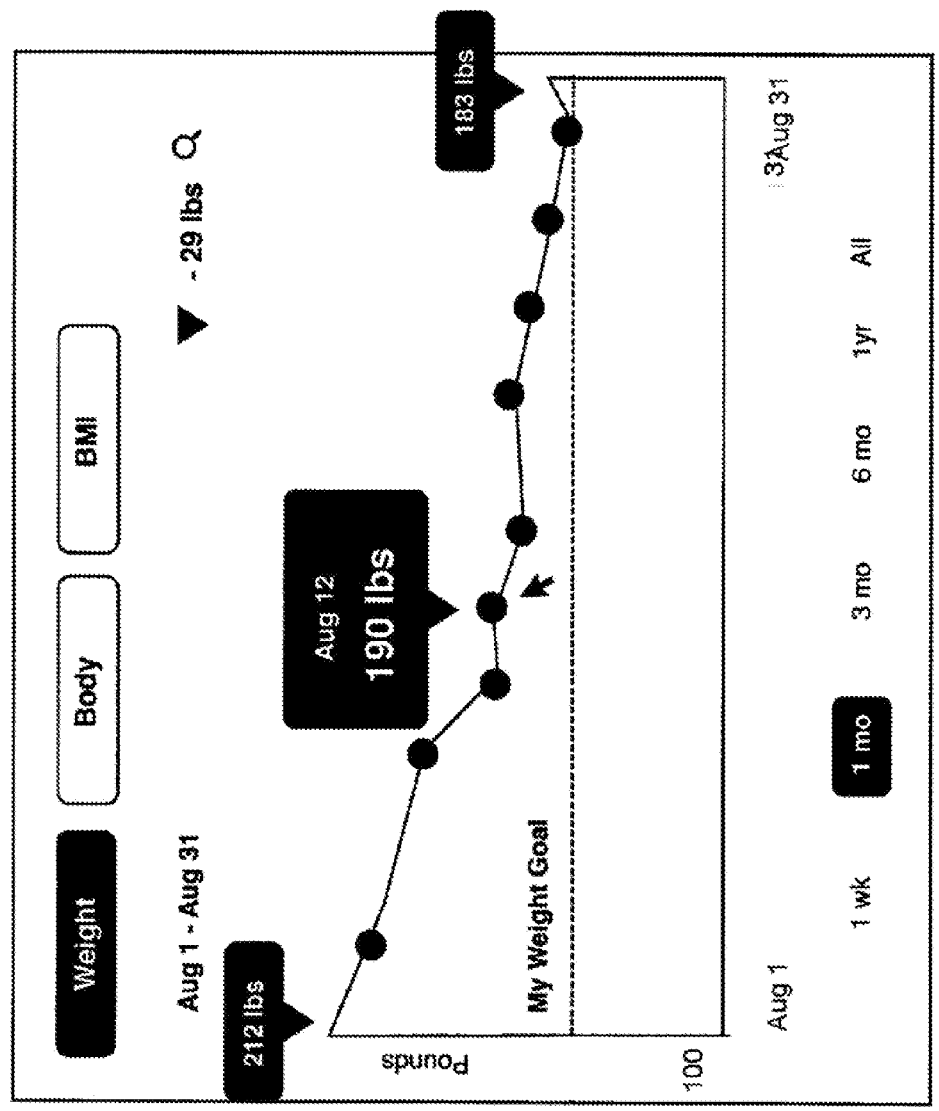
FIGS. 7A-7D are exemplary illustrations of formats and presentations of exemplary biometric-type data and content in a user interface incorporated in the biometric monitoring device and/or separate therefrom (including, for example, a website (accessed via, for example, the Internet), mobile phone application, or program operating on a personal computer), according to at least one embodiment of the present inventions.
Figure 7B:
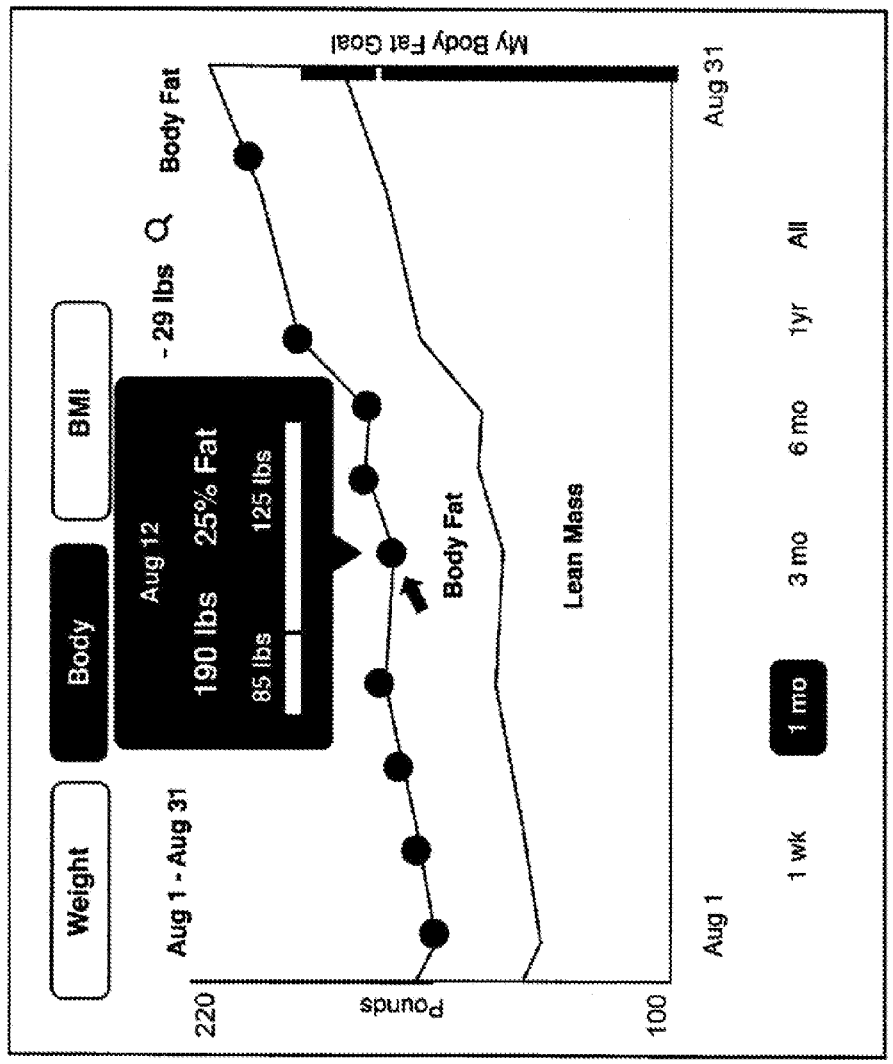
Figure 7C:
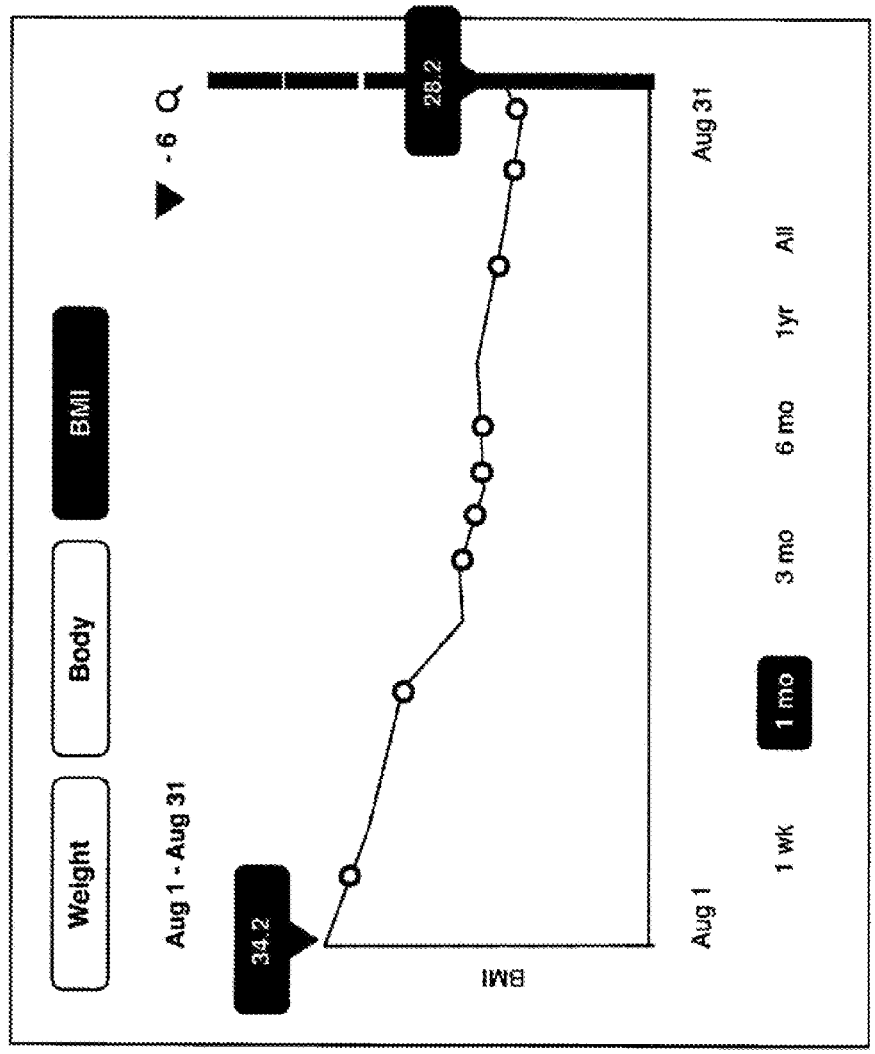
Figure 7D:
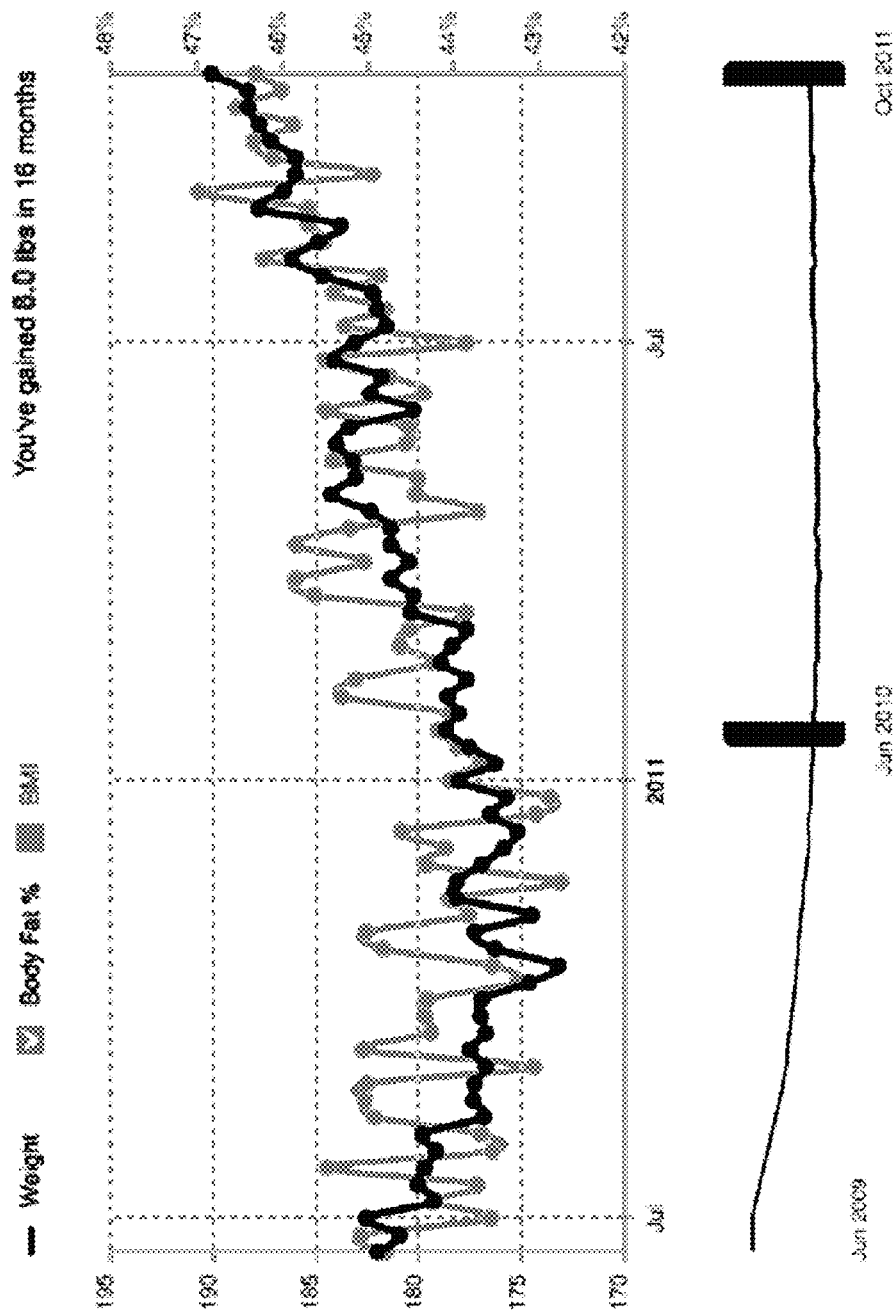
Figure 8A:
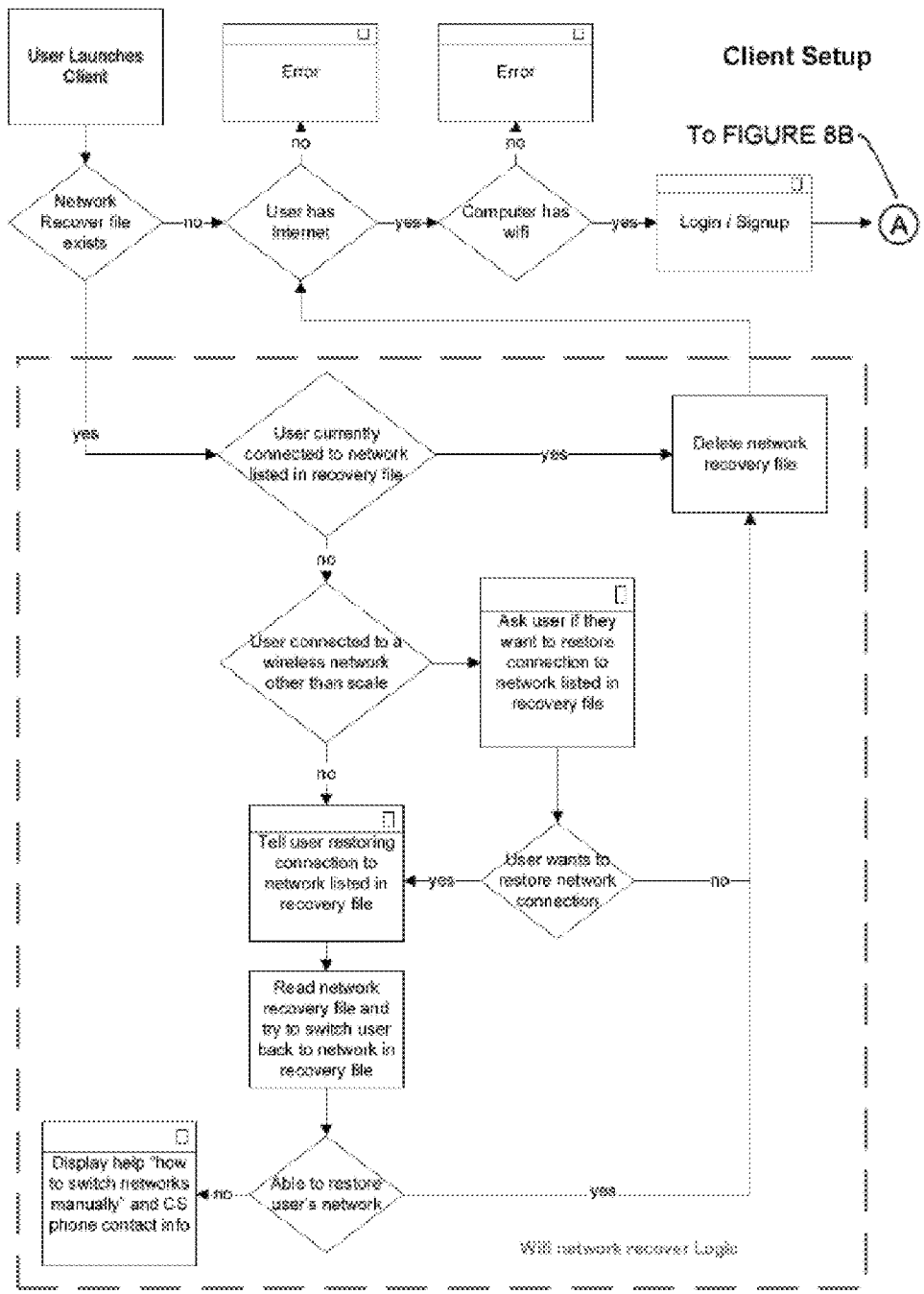
FIGS. 8A-8M illustrate exemplary work-flows of initial client/user set-up, site workflow and other programming workflow routines, according to at least one embodiment of the present inventions; wherein in one embodiment, the user/client may program or customize the operations of the biometric monitoring device via the user interface, an external device via the communication circuitry (for example, via wired or wireless connection to a computer or personal computing device) and/or through a web interface (e.g., www.fitbit.com) on the user interface of the biometric monitoring device or external device; notably, in a preferred embodiment, the setup of the biometric monitoring device for a first client/user may be implemented without wired communication; moreover, these processes, including the initial setup of the biometric monitoring device is accomplished by a client application or web browser running on a secondary device, for example, a personal computer or mobile phone; in one embodiment, network credentials, for example WiFi SSID and password, may be stored on the secondary device and communicated or transferred to the biometric monitoring device without the user manually entering information by way of switching the secondary device to the network broadcast by the biometric monitoring device.
Figure 8B:
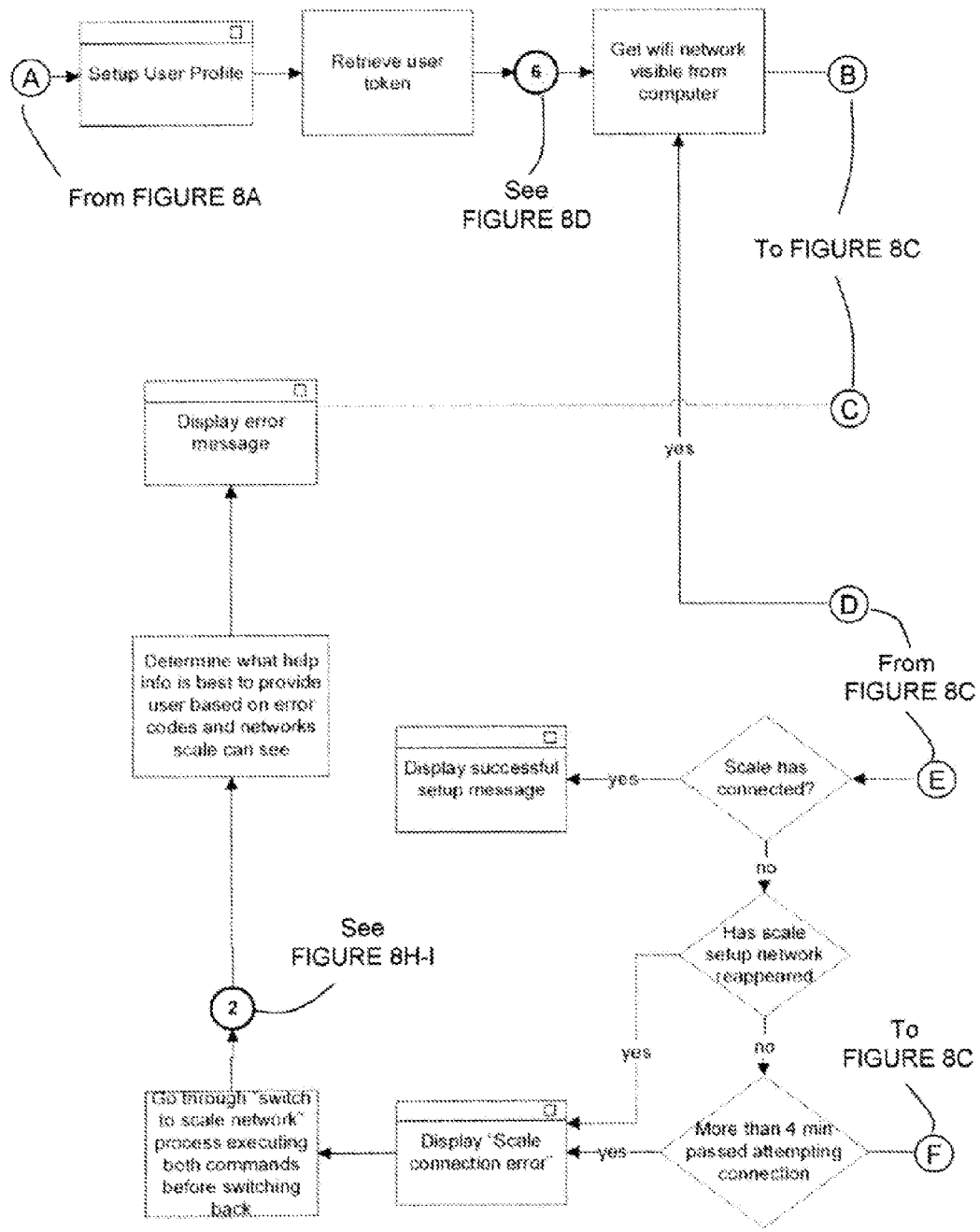
Figure 8C:
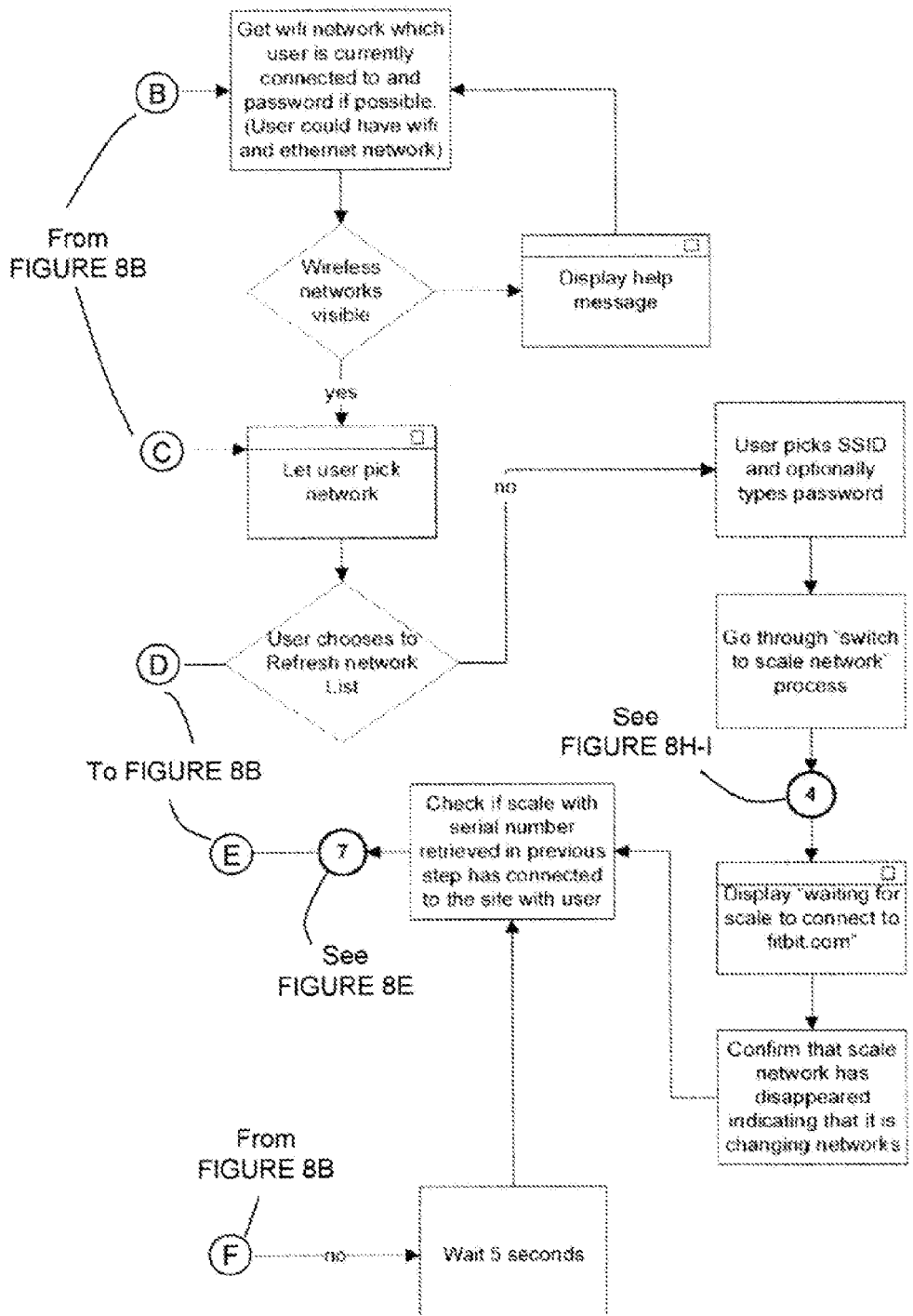
Figure 8D:
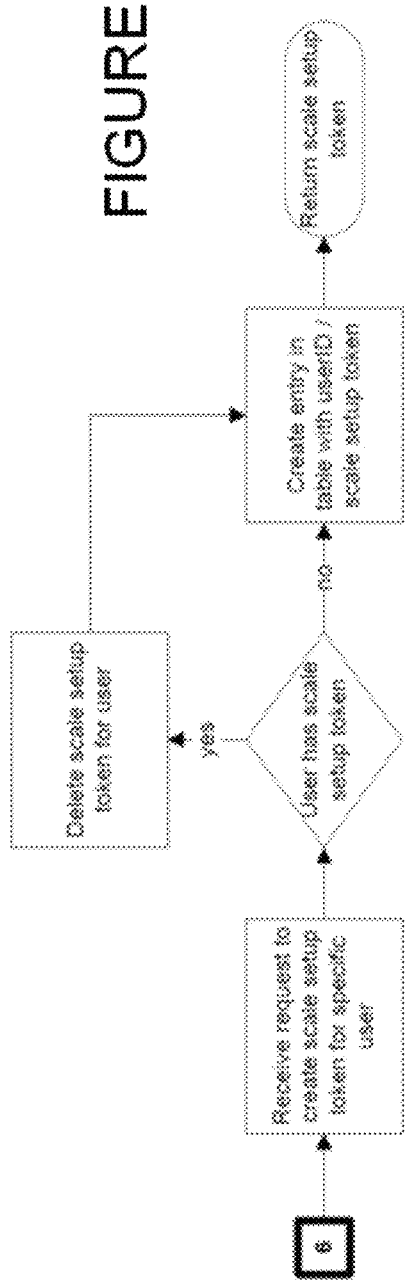
Figure 8E:
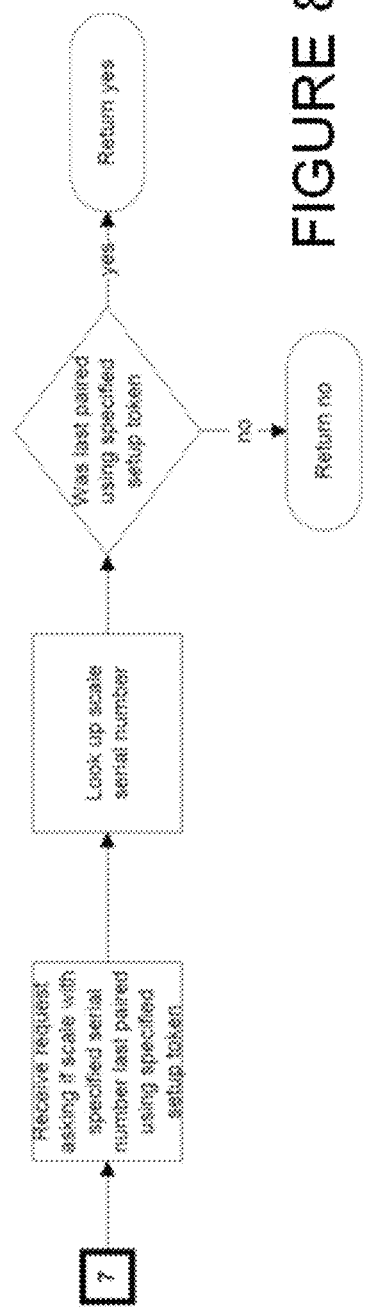
Figure 8F:
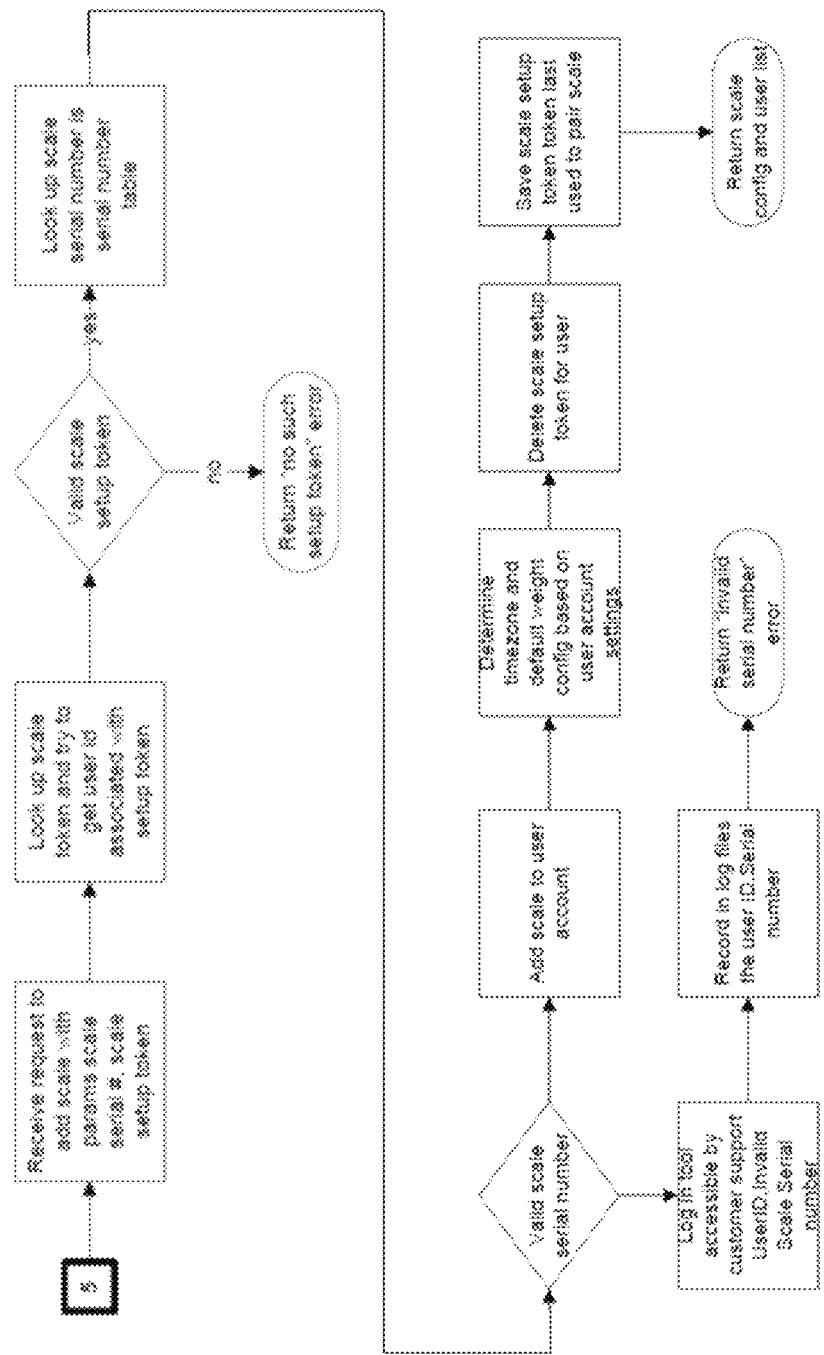
Figure 8G:
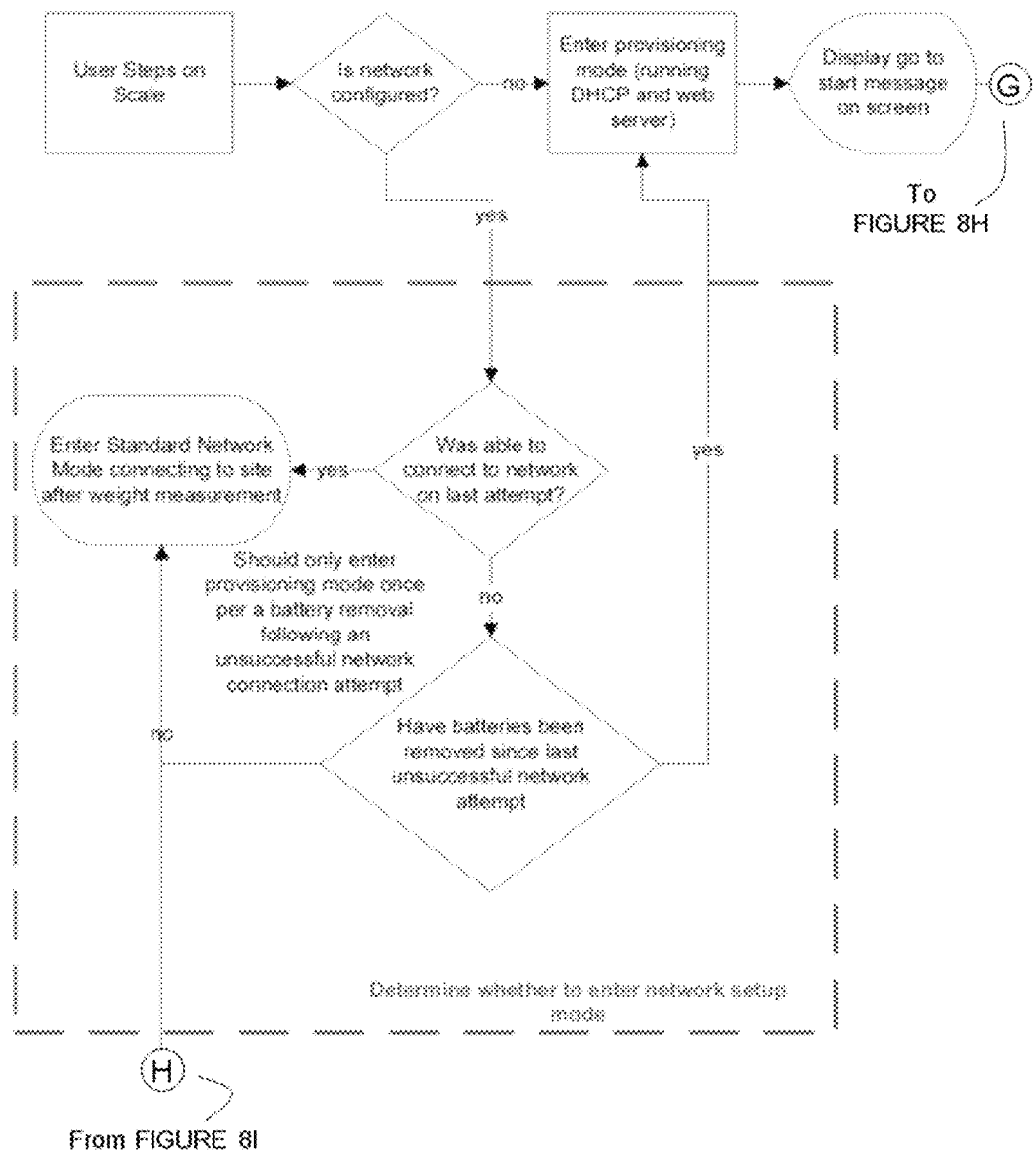
Figure 8H:
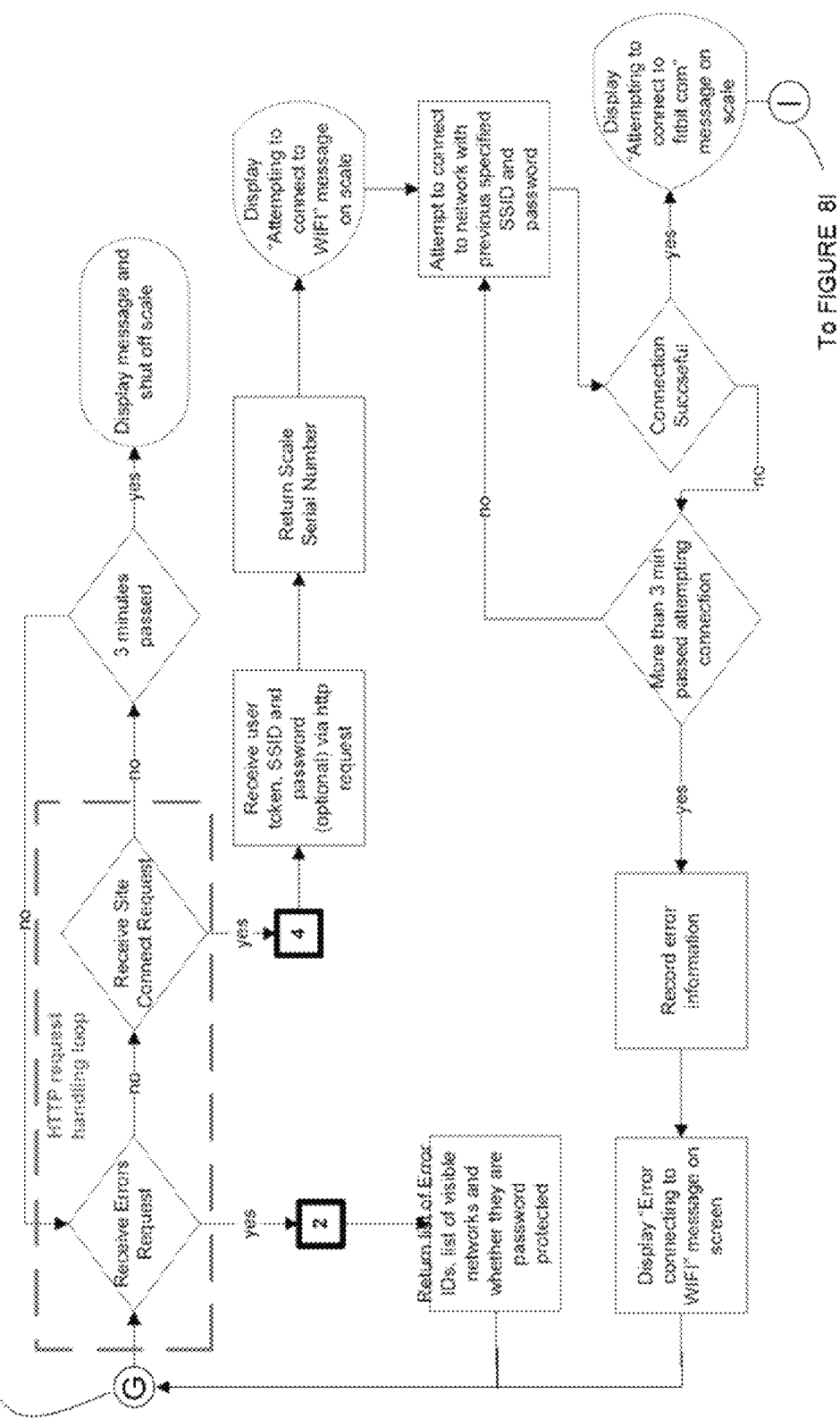
Figure 8I:
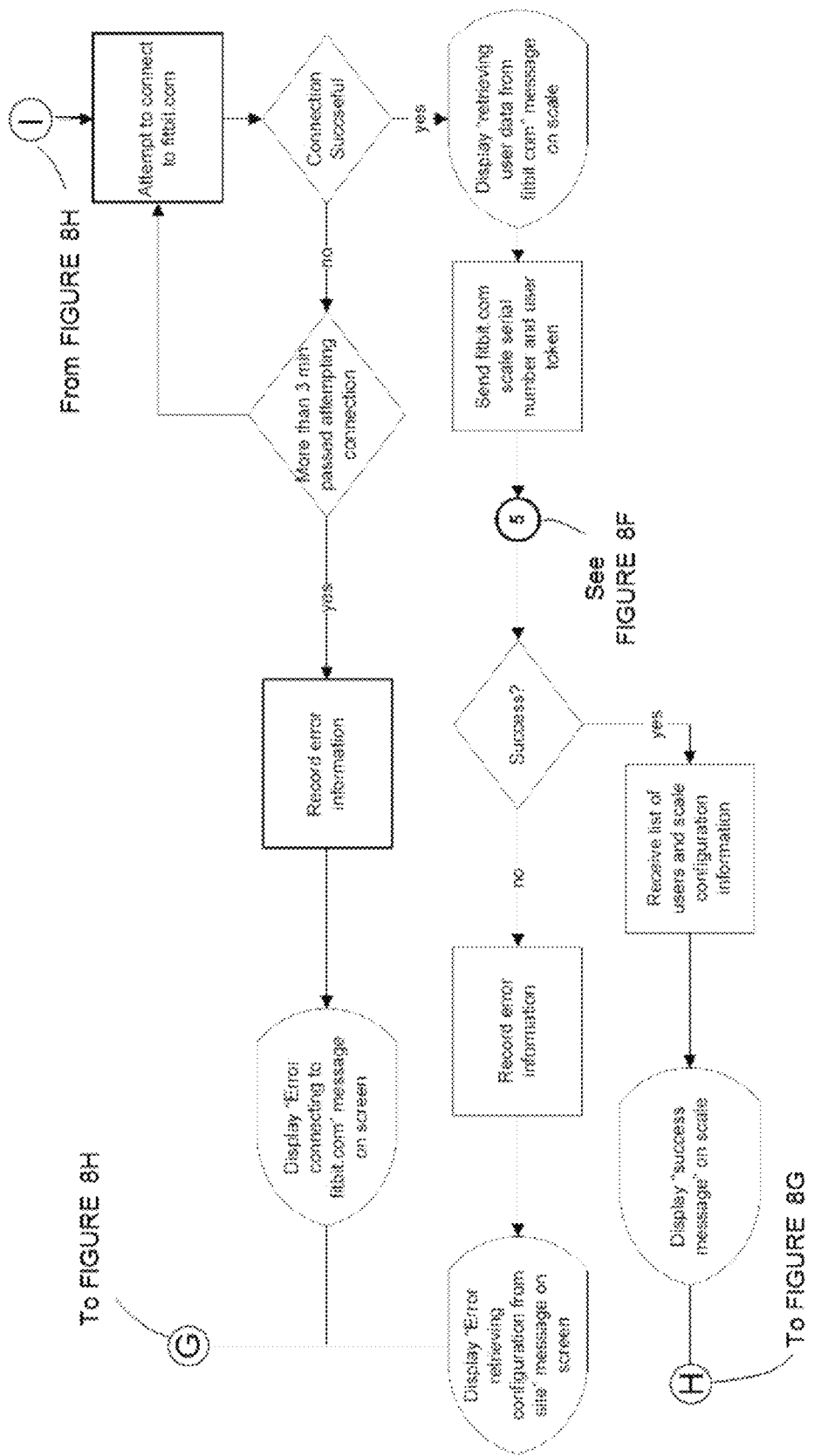
Figure 8J:
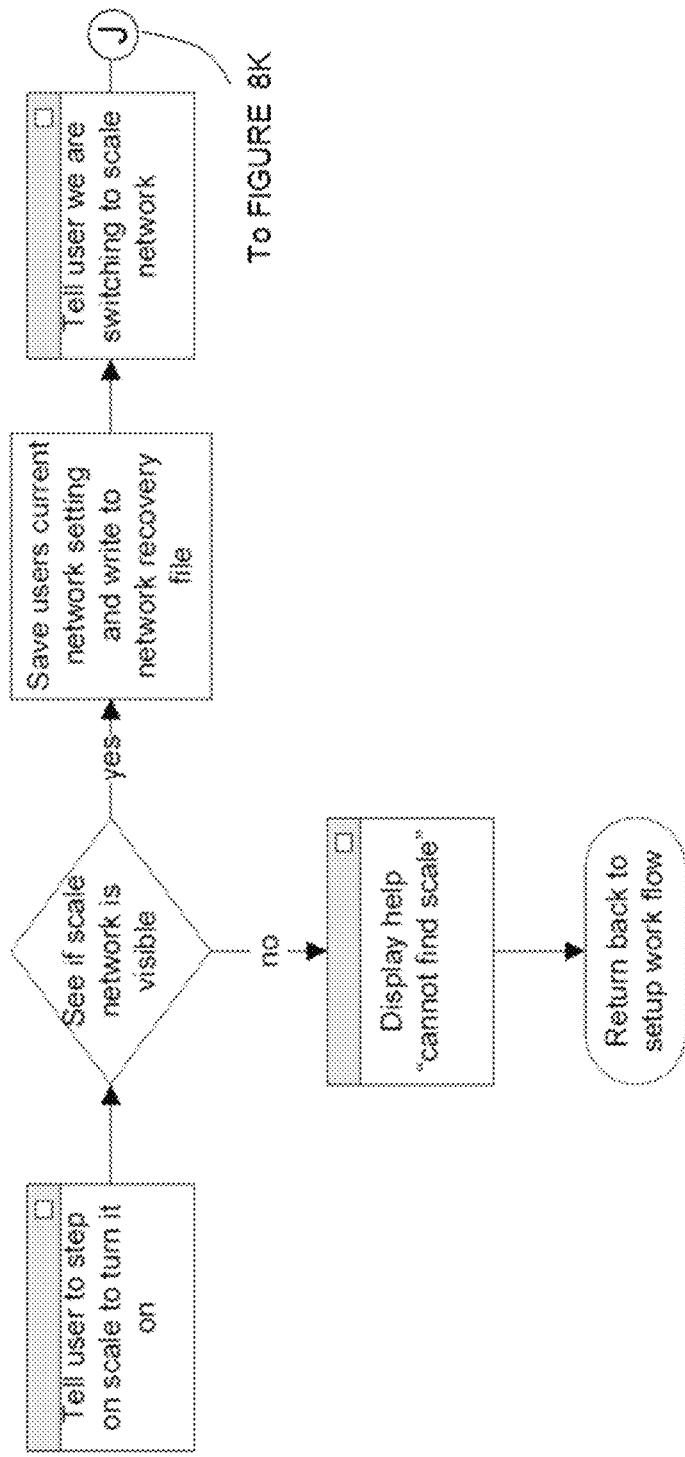
Figure 8K:
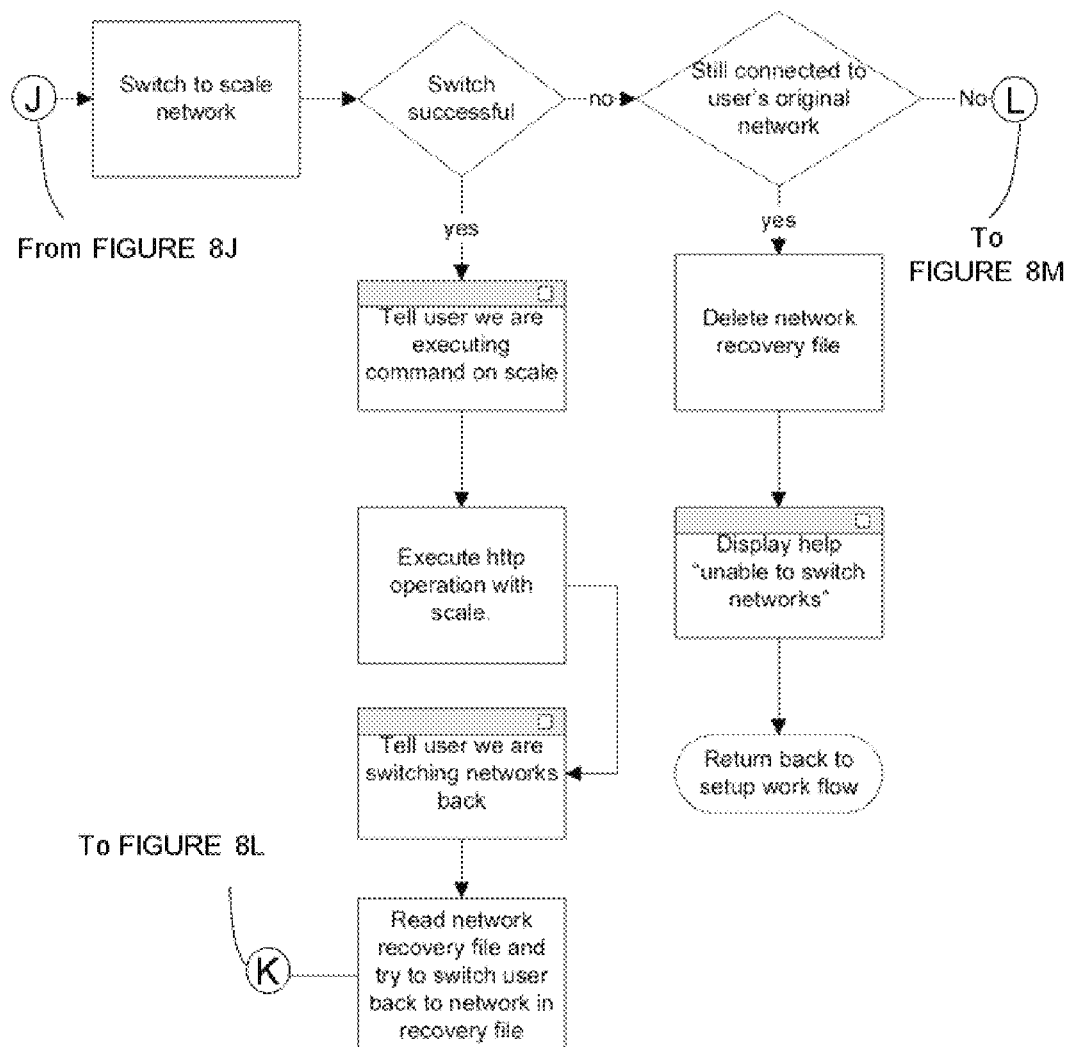
Figure 8L:
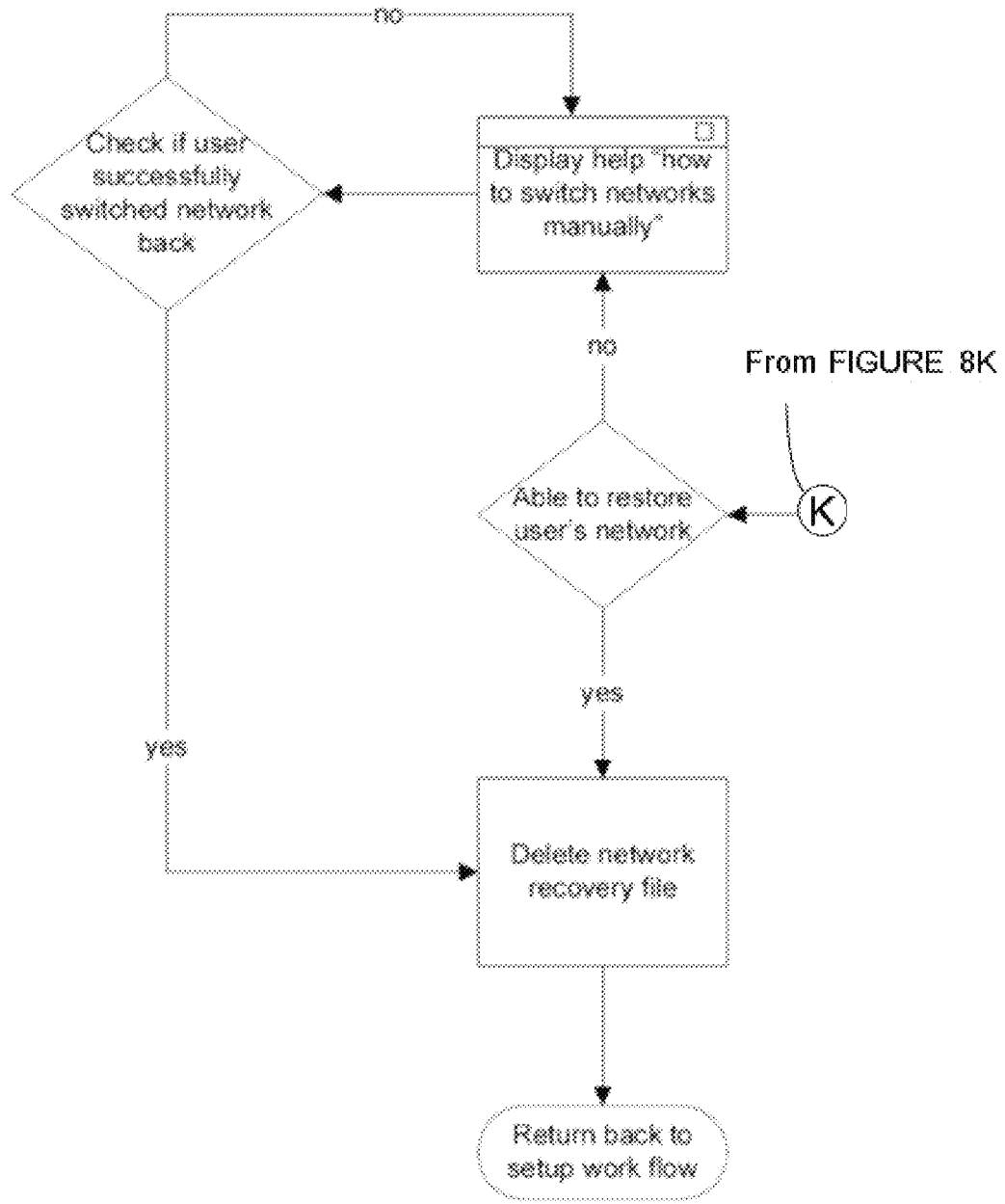
Figure 8M:
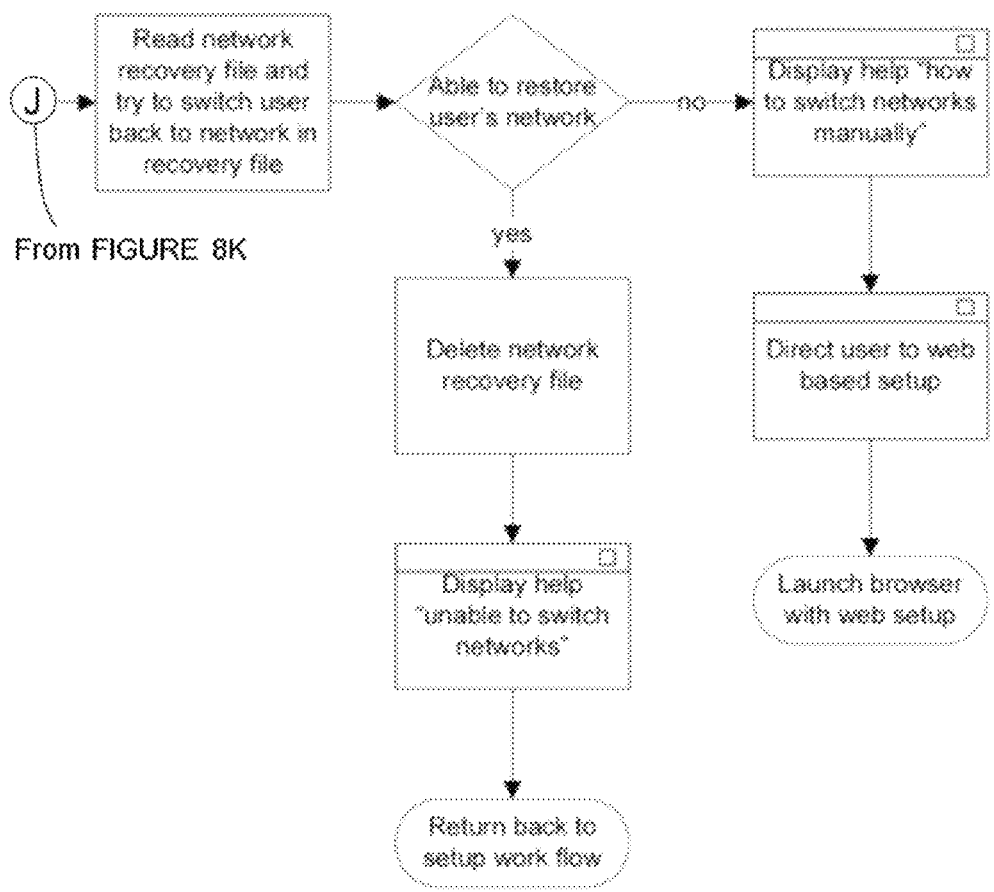

Again, there are many inventions described and illustrated herein. The present inventions are neither limited to any single aspect nor embodiment thereof, nor to any combinations and/or permutations of such aspects and/or embodiments. Each of the aspects of the present inventions, and/or embodiments thereof, may be employed alone or in combination with one or more of the other aspects of the present inventions and/or embodiments thereof. For the sake of brevity, many of those combinations and permutations are not discussed separately herein.

DETAILED DESCRIPTION

There are many inventions described and illustrated herein. In one aspect, the present inventions are directed to biometric monitoring devices, and method of operating and controlling same, which monitor, calculate, determine and/or sense physiologic data, including the weight of a user (for example, a human or non-human animal) and, via a user interface, display biometric or physiologic information including, for example, current information, historical information and/or current information in view of historical information.

In another aspect of the present inventions, the biometric monitoring device also includes one or more environmental sensors to detect, measure and/or sense ambient environmental conditions. For example, the one or more environmental sensors may detect, measure and/or sense ambient pressure, temperature, sound, light, humidity, location and/or atmosphere. In response thereto, the biometric monitoring device of this aspect of the present inventions, in addition to monitoring, calculating, determining and/or sensing biometric or physiologic data of a user, may provide status information to the user and/or control or operate such local external devices and/or appliances in accordance with predetermined instructions.

With reference to FIG. 1A, in one embodiment biometric monitoring device 10 includes one or more physiological sensors, a user interface and processing circuitry. The biometric monitoring device 10 includes a physiological sensor to detect, measure and/or sense a weight of a user. (See, FIG. 2A). The biometric monitoring device 10 may include additional physiological sensors including, for example, a body fat sensor. (See, for example, FIG. 2B). Indeed, biometric monitoring device 10 may include other additional physiological sensors including, for example, sensors to detect, measure and/or sense data which is representative of heart rate, respiratory rate, hydration, height, sun exposure, blood pressure and/or arterial stiffness. (See, FIG. 2C). Notably, in addition thereto, or in lieu thereof, biometric monitoring device 10 of the present inventions may detect, measure and/ or sense (via appropriate sensors) other physiologic data; all such physiologic data or parameters, whether now known or later developed, are intended to fall within the scope of the present inventions. Similarly, although the sensors of FIGS. 2B and 2C are depicted as independent, they may be collaborative and perform multiple types of measurements. For example, a weight sensor in combination with bio-impedance analysis circuitry may be used to measure body fat, hydration, and/or fat-free mass.

The user interface 14 of biometric monitoring device 10 provides or facilitates exchange of physiologic information and, in certain embodiments, other information or data. For example, biometric monitoring device 10 may include one or more displays (see, for example, FIG. 3A) to present physiologic information including, for example, current information, historical information and/or comparison like information, for example, current information in view of historical information. Briefly, the historical information or data may include, for example, historical weight and/or body fat data measured by the monitoring device (which may be stored internally to and/or externally from biometric monitoring device 10), historical user activity data, food consumption data, and/or sleep data (which may be measured or monitored by other personal and/or portable devices (for example, Fitbit's portable activity monitoring/tracking device and acquired by biometric monitoring device 10, see, for example, U.S. patent application Ser. No. 13/156,304, filed on Jun. 8, 2011, entitled "Portable Monitoring Devices and Methods of Operating Same" (which is incorporated herein by reference in its entirety)), historical user biometric or physiologic data (for example, heart rate, blood pressure, arterial stiffness, blood glucose levels, cholesterol, duration of TV watching, duration of video game play and/or mood). Notably, such historical data may be presented in pictorial, graphical and/or textual form.

In addition to or in lieu of one or more displays, user interface 14 may include one or more speakers to provide the user with such physiologic data or information (whether current, historical or both) in aural form. (See, FIGS. 3B and 3C).

The user interface 14 may also include an input mechanism to facilitate input of, for example, user data, commands and/or selections. In one embodiment, the user may communicate with biometric monitoring device 10 via a user interface including, for example, a touch pad, touch screen, buttons, switches and/or knobs. In another embodiment, user interface 14 of a biometric monitoring device includes one or more audio sensors to detect speech or sounds. (See, for example, FIGS. 3D and 3E). In this way, for example, the user may input data, commands and/or selections to biometric monitoring device 10. For example, in response to speech or sounds from the user, biometric monitoring device 10 may determine or identify the appropriate user (for example, from a list stored therein) which facilitates correlation of physiologic data (acquired by the one or more physiological sensors) with a particular user.

Notably, user interface 14 may include any output and/or input device now known or later developed including such input devices as touch screens, motion sensors, biometric sensors and/or proximity sensors. (See, FIGS. 3F and 3G). Moreover, all combinations and permutations of output and input devices are intended to fall within the scope of the present inventions. For example, user interface 14 may include one or more biometric sensors (for example, a toe print detector) to identify or determine a particular user and/or a touch screen to facilitate selection of a particular user or user profile. (See, FIGS. 3F and 3G). In response thereto, biometric monitoring device 10 may, in addition to correlating the current physiologic data with the particular user, present the associated historical information to the user via visual and/or audio techniques of user interface 14.

As noted above, in one embodiment, biometric monitoring device 10 may include processing circuitry to calculate, assess and/or determine physiologic information using data sensed, detected and/or measured from physiological sensor(s) 12. (See, FIG. 4). For example, processing circuitry 16 calculates or determines the user's weight based on or using a weight sensor. In another embodiment, using data from a body fat sensor (for example, bioelectrical impedance analysis (BIA) electrodes), processing circuitry 16 may calculate or determine a user's body fat composition and/or body mass index. For example, via the BIA electrodes, a small current is applied to the body and the characteristics of the return current measured in the electrodes are representative of the body fat composition of the user. The processing circuitry 16, based on data acquired or detected by the BIA electrodes and in combination with information about the user (e.g., weight, height, age, and gender), may calculate or determine a user's body fat composition and/or body mass index. The processing circuitry 16 may employ similar measurement methods to derive a user's fat-free mass, hydration (e.g., total body water, intracellular water, and/or extracellular water) and body cell mass.

The processing circuitry 16 may also calculate, assess and/or determine other biometric or physiological quantities such as heart rate, blood pressure and/or arterial stiffness. For example, biometric monitoring device 10 may include one or more LED/photodetector pairs disposed therein such that when the user placing blood-perfused area of the foot (for example, the big toe) over the one or more LED/photodetector pairs, biometric monitoring device 10 may implement or perform photo plethysmography to calculate, assess and/or determine heart rate, respiratory rate, blood pressure and/or arterial stiffness. Indeed, biometric monitoring device 10 may employ an array of LEDs-photo detectors to adaptively determine which location on the foot provides the best plethysmography signal.

Notably, processing circuitry 16 of biometric monitoring device 10 may also determine or calculate the size and shape of the user's foot via analysis of data from LED/photo detectors, a camera, or multiple BIA electrodes placed on the top surface of device. Foot size may also be determined with designated array of electrodes, where for example, the electrodes may consist of discrete metal probes, indium-tin-oxide (ITO) coatings on a substrate, and/or a capacitive array. In this way, for example, a parent may measure and track (over time) the change in size and shape of a child's foot.

Where biometric monitoring device 10 includes a heart rate sensor, processing circuitry 16 may employ data from the heart rate sensor to calculate, assess and/or determine the user's heart rate using, for example, ballistocardiography or with a video camera instead of photo detectors. Based on the output of such sensors, processing circuitry 16 may calculate, assess and/or determine the user's heart rate and store and/or output such information (for example, display).

Notably, biometric monitoring device 10 may be programmed or configured (for example, by the user via user interface 14 of biometric monitoring device 10 and/or an external device that communication with biometric monitoring device) to enable or engage (or disable or disengage) one or more physiological sensors and/or enable or disable the monitoring, calculating and/or determining of one or more physiological parameters (based on or using data from such sensors). In this way, the user may configure biometric monitoring device 10 to acquire selected physiologic data (via enabling and/or disabling selected physiological sensors) and/or calculate, monitor and/or determine selected physiological parameters (via enabling or disabling processing circuitry 16 accordingly). Such configuration may be on a user basis (each user includes his/her unique configuration) and/or on a device basis (the device is programmed into a particular configuration regardless of the user).

For example, where biometric monitoring device 10 includes a body fat sensor having electrodes for implementing BIA, it may be advantageous to disable such sensor where the user is pregnant or is equipped with a pace maker. In this regard, pregnant women are often discouraged from taking BIA measurements. However, the body fat sensor may be enabled for male users (for example, selected male users) or non-pregnant female users (for example, selected female users) wherein for such users, processing circuitry 16 (which may include control circuitry as well) enables the body fat sensor to acquire corresponding data. Thereafter, processing circuitry 16 may responsively calculate, assess and/or determine the user's blood pressure and/or arterial stiffness (based on or using data from such sensor). Moreover, processing circuitry 16 may store body fat information for certain of the users and/or output such information (for example, display) thereto.

Notably, the processing circuitry may be discrete or integrated logic, and/or one or more state machines, processors/controllers (suitably programmed) and/or field programmable gate arrays (or combinations thereof); indeed, any circuitry (for example, discrete or integrated logic, state machine(s), processor(s)/controller(s) (suitably programmed) and/or field programmable gate array(s) (or combinations thereof)) now known or later developed may be employed to calculate, determine, assess and/or determine the physiologic information of the user based on sensor data. In addition thereto, or in lieu thereof, the processing circuitry may control the physiologic sensors and/or implement user commands as described herein. In operation, the processing circuitry may perform or execute one or more applications, routines, programs and/or data structures that implement particular methods, techniques, tasks or operations described and illustrated herein. The functionality of the applications, routines or programs may be combined or distributed. Further, the applications, routines or programs may be implementing by the processing circuitry using any programming language whether now known or later developed, including, for example, assembly, FORTRAN, C, C++, and BASIC, whether compiled or uncompiled code; all of which are intended to fall within the scope of the present invention.

With reference to FIGS. 1B, 1C and 5A-5C, embodiments of biometric monitoring device 10 may include communication circuitry (wireless and/or wired) to transmit biometric or physiologic data and/or receive, for display via user interface 14, web content, news, traffic, weather, social content (for example, instant messaging), advertisement, emails, calendar schedule, exercise or diet coaching, instructions and/or data, and goal oriented information (for example, a user's progress toward biometric or physiological goals (weight, body fat composition, hydration, caloric consumption, activity and/or sleep)) as well as biometric or physiologic information including, for example, current information, historical information and/or comparison information (for example, current information in view of historical information).

As noted above, the historical information or data may include, for example, historical weight and/or body fat data measured by the monitoring device (which may be stored internally to and/or externally from biometric monitoring device 10), historical user activity data, food consumption data, and/or sleep data (which may be measured or monitored by other personal and/or portable activity monitoring devices (for example, Fitbit's portable activity monitoring/tracking device and acquired by biometric monitoring device 10), historical user biometric or physiologic data (for example, heart rate, blood pressure, arterial stiffness, blood glucose levels, cholesterol, duration of TV watching, duration of video game play and/or mood). Notably, such historical data may be presented in pictorial, graphical and/or textual form.

The communication circuitry 18 may implement or employ any form of communications (for example, wireless, optical, or wired) and/or protocol (for example, standard or proprietary (for example, Bluetooth, ANT, WLAN, powerline networking, cell phone networks, and Internet based and/or SMS) now known or later developed, all forms of communications and protocols are intended to fall within the scope of the present inventions.

In one preferred embodiment, biometric monitoring device is a multi-protocol LAN to WAN gateway where local devices can be Bluetooth, ANT, Zigbee, etc. and the biometric gateway communicates to the Internet via or over a communication path (for example, a cell phone network, WLAN, etc.). The biometric monitoring device may operate as an "open hotspot" so that no user setup is required. For instance, a user may have elsewhere established a network account (e.g., www.fitbit.com or another website) to an external device (e.g., a Fitbit Tracker) through its unique device ID, then the gateway automatically recognizes the device and sends data to the suitable, predetermined, associated and/or correct account and location. The data may go directly to the destination (for example, via the Internet) or through an intermediary first. Destinations or intermediaries could be other devices or a network service (e.g., www.fitbit.com). The original device to account/location link setup may be completed as part of a user initiated setup process or may have been pre-configured as part of the purchasing or acquisition process at the manufacturer or another intermediary. The following are additional exemplary embodiments:

A user sets up her first Fitbit Tracker at work. She already owns and has setup the current invention at home. She takes her Fitbit Tracker home and it automatically starts syncing data through the invention without further setup.

A user owns a Garmin ANT device that is set up to sync data to Garmin's website.

She then acquires the current invention. Once she connects the invention to the internet, the Garmin device can automatically send its data to Garmin's website through the invention without any further setup. The invention could also send the data to Garmin's website via an intermediary website (e.g., www.fitbit.com).

The user may also enable or disable (for example, turn on or off) communication of the activity or physiologic data via the biometric monitoring device. In addition thereto, or in lieu thereof, the user may enable or disable acquisition or storage of data by the external destination (for example, a server connected thereto or to the Internet; for example, a website associated with the server). In this way, the user controls, among other things, the ability of or for data destinations to receive the data.

The communication circuitry 18 may provide for one-way or two-way communication to, for example, facilitate or provide input of data and/or commands. Indeed, where the biometric monitoring device includes two-way communications, communication circuitry 18 facilitates or provides data or command transmission to and from peripheral devices and/or the Internet. Thus, in certain embodiments, communication circuitry 18 facilitates or provides external connectivity to, for example, the Internet and/or remote or local external devices and/or appliances. Here, the biometric monitoring device acts or functions as a communication hub or path in relation to local external devices and/or appliances.

Where communication circuitry 18 provides one-way or two-way communication to the Internet and/or (remote or local) external devices and/or appliances (see, for example, FIGS. 6A-6C), biometric monitoring device 10 may upload data and/or commands to and/or download data and/or commands from, for example, selected websites, health professionals, trainers, weight or health oriented monitoring groups/organizations or specialists, and/or the like (hereinafter collectively "third party" or "third parties"). In this way, biometric monitoring device 10 may manually or automatically provide physiologic data to such third parties. The biometric monitoring device 10 may also receive data and/or instructions/comments, for example, health or training guidance or feedback via biometric monitoring device 10. For example, where biometric monitoring device 10 provides physiologic data (for example, weight, heart rate and/or blood pressure) to one or more third party devices or websites, such third parties (for example, health professionals or trainers) may monitor and/or provide feedback based on such physiologic data. In this way, such third party or parties may provide periodic, continuous and/or intermittent monitoring and/or feedback, notwithstanding the user/patient is substantially remote or distant from such third parties, or where significant monitoring of the user/patient is inconvenient or not feasible (for example, due to costs or locations).

The communication circuitry 18 may also facilitate programming of biometric monitoring device 10, for example, programming the device to acquire selected physiologic data (for example, via enabling and/or disabling selected physiological sensors) and/or calculate, monitor and/or determine selected physiological parameters (for example, via enabling or disabling processing circuitry 16 accordingly). The programming of biometric monitoring device 10 may be via the user or third party. In this way, for example, a third party may customize or tailor the acquisition of physiologic data based on the user, the situation (for example, physical condition of the user), and the acquisition of desired information.

Indeed, communication circuitry 18 of biometric monitoring device 10 may also facilitate programming of the activity monitoring device, for example, programming the device to acquire selected activity and/or physiologic data (for example, via enabling and/or disabling selected sensors), acquiring activity and/or physiologic data, and/or calculate, monitor and/or determine selected activity parameters (for example, via enabling or disabling processing circuitry 16 accordingly). In this way, for example, a user (via biometric monitoring device 10) may upload, transmit or communicate activity data and/or physiologic data to, for example, one or more selected data storage devices.

In addition thereto, biometric monitoring device 10 may also transmit user identification data to correlate the physiologic data and/or activity data with a particular user or particular device (external monitoring device and/or biometric device). Here, the user identification data is any data that identifies a particular user, a particular device and/or from which a particular user and/or device may be determined. For example, the user identification data may be data associated with a particular user (for example, a particular value, character, number, combination thereof, and/or sequence thereof) and/or a particular device (for example, a particular value, character, number, combination thereof, and/or sequence thereof). Indeed, in one embodiment, biometric monitoring device 10 may be paired with one or more external monitoring devices (for example, one or more portable activity monitoring devices) and receipt of data therefrom may be "assumed" or implied to be associated with a user or external device.

The user identification data may be separate data (associated with a particular user and/or device) and/or may be inherent, incorporated in or implied from other data (for example, physiologic data from a biometric monitoring device or activity (which may include sleep)) or physiologic data from a portable activity monitoring device and/or biometric device. Thus, where the user identification data is in the form of a device identification data (for example, a serial number), biometric monitoring device 10 may, in addition to transmitting physiologic data and/or activity data of a user, transmit device identification data. In one embodiment, the device identification data may be associated with or correlated to a data storage location or an account wherein the transmitted data is stored in relation thereto or connection therewith. Thus, such device identification data may be associated with or correlate to a particular user. Here, the device identification data is user identification data.

In another embodiment, biometric monitoring device 10 is paired with or recognizes one or more external devices (for example, a particular code, signal or data stream of one or more portable activity monitoring devices). In this embodiment, data received from the external device (for example, portable activity monitoring device) may be "assumed" or implied to be associated with a particular user or external device (for example, via biometric monitoring device 10, external local data storage and/or remote data storage). Here, the user identification data may be inherent, incorporated in or implied from the communication or other data with the external device.

The user identification data may be (associated with a particular user and/or device) and from the physiologic, activity and/or environmental data. In addition thereto, or in lieu thereof, the user identification data may be incorporated or integrated in the physiologic, activity and/or environmental data. Moreover, the user identification data may be inherent, incorporated in or implied from other data (for example, physiologic data from a biometric monitoring device or activity (which may include sleep)) or physiologic data from a portable activity monitoring device and/or biometric device. Indeed, the user identification data may be implied from the communication with an external device (for example, portable activity monitoring device and/or biometric device).

The user identification data may be determined automatically (via data transfer using the communication circuitry) or manually (via user input using the user interface). As such, in one embodiment, the biometric monitoring device may automatically obtain the user identification data to provide/acquire data which is representative of particular details of the user (for example, height, weight, gender and/or age) from data storage (for example, resident, local and/or remote data storage). Such details may be employed by the processing circuitry of the biometric monitoring device to determine or calculate physiologic data (for example, body fat and lean muscle mass).

Notably, the data storage devices may be resident, local and/or remote wherein remote off-site data storage devices may be accessed, for example, via the Internet. Notably, the one or more data storage devices may store the data in digital and/or analog form; indeed, any data storage device, whether now known or later developed, is intended to fall within the scope of the present inventions.

As discussed in more detail herein, in certain embodiments, the biometric monitoring device may also operate, program and/or control local external devices and/or appliances. For example, the communication circuitry of the biometric monitoring device may also function or operate as a relay or hub to provide or facilitate communication for external devices to each other or to the Internet. For example, the biometric monitoring device may connect to the Internet via WLAN but also be equipped with an ANT radio. An ANT device may communicate with the biometric monitoring device to transmit its data to the Internet through the WLAN of the biometric monitoring device (and vice versa). Moreover, where the communication circuitry is equipped with Bluetooth, other Bluetooth-enabled devices (for example, mobile or smart telephones) that come within suitable or effective reach or range, the biometric monitoring device may transmit data to or receive data from such Bluetooth-enable device and/or the Internet through the network of the mobile or smart telephones. Indeed, data from another device may also be transmitted to the biometric monitoring device and stored (and vice versa) or subsequently transmitted at a later time.

In addition, the communication circuitry may also be employed to detect or identify a particular user via acquisition of data which identifies the particular user. In this regard, in one embodiment, the communication circuitry acquires data or information (for example, a code that correlates to the particular user) from a separate device that designates, identifies and/or is unique to the user (for example, Fitbit's portable activity monitoring/tracking device or a mobile communication device, for example, a tablet, laptop or mobile phone or RFID tag). In this way, the biometric monitoring device (for example, the processing circuitry) determines or identifies a particular user and may, in response thereto, configure the biometric monitoring device in accordance with the user's profile (in the event that the biometric monitoring device is configured on a user basis), present the associated historical information or data via the user interface and/or receives, for display via the user interface, selected web content, news, traffic, weather, social content (for example, instant messaging), advertisement, emails, calendar schedule, exercise or diet coaching, instructions and/or data, and goal oriented information (for example, a user's progress toward biometric or physiological goals (weight, body fat composition, hydration, caloric consumption, activity and/or sleep)).

Notably, in those situations where the biometric monitoring device determines or identifies a particular user via another technique (for example, biometric sensor, such as speech or sound recognition or a toe, finger and/or foot print detection, and/or user selection from a list of pre-programmed users or user profiles), the aforementioned discussion is entirely applicable. That is, in the event that the biometric monitoring device is configured or configurable on a user basis, upon determining or identifying a particular user, the biometric monitoring device in accordance with the user's profile, presents the associated historical information or data via the user interface and/or receives, for display via the user interface, selected web content, news, traffic, weather, social content (for example, instant messaging), advertisement, emails, calendar schedule, exercise or diet coaching, instructions and/or data, and goal oriented information as well as physiologic information including, for example, current information, historical information and/or current information in view of historical information.

As indicated above, the biometric monitoring device, in addition to monitoring, calculating and/or determining of one or more physiological parameters (based on or using data from resident sensors), may receive web content for display on the user interface of the biometric monitoring device. The following are examples of the types and/or content of information that may be provided to the user.

- Historical graphs of weight and/or body fat data measured by the scale but stored remotely;
- Historical graphs of user activity and/or foods consumed and/or sleep data that are measured by other devices and/or stored remotely (e.g., fitbit.com);
- Historical graphs of other user-tracked data stored remotely. Examples include heart rate, blood pressure, arterial stiffness, blood glucose levels, cholesterol, duration of TV watching, duration of video game play, mood, etc.;
- Physiologic data corresponding to average or norms, for example, for comparison purposes wherein, in one embodiment, the user's physiologic data is compared to or contrasted with average physiologic data (for example, on an age, gender or condition basis (for example, a pregnant women's physiologic data is compared with typical physiologic data based on stage, size and age));
- "Mash-up" data pertaining to user's physiologic data and user's water intake—for example, correlations of (i) hydration levels to manually logged water consumption and (ii) hydration levels to automatically measured water consumption via a "smart" water bottle (e.g., Camelbak flow meter hydration gauge system);
- "Mash-up" data pertaining to user's physiologic data and user's sleep—for example, correlations of (i) heart rate to blood pressure and (ii) body weight and/or fat to sleep time, patterns and/or quality;
- "Mash-up" data pertaining to user's physiologic data and user's activity—for example, correlations of (i) hydration to activity levels and (ii) heart rate and/or variability to activity levels and/or patterns;
- "Mash-up" data pertaining to physiologic data and potentially related external events such as correlations of (i) user's body weight and/or fat to ambient environment for example, geography, temperature, traffic and/or weather, (ii) user's heart rate and/or blood pressure to financial markets (for example, S&P 500, NASDAQ or Dow Jones); here the data analysis of the user's biometric or physiologic data is correlated to web content and/or external devices that are in communication with the biometric monitoring device;
- Coaching and/or dieting data based on one or more of the user's current weight, weight goals, food intake, activity, sleep, and other data;
- User progress toward weight, activity, sleep, and/or other goals;
- Summary statistics, graphics, badges, and/or metrics (e.g., "grades") to describe the aforementioned data;
- The aforementioned data displayed for the user and his/her "friends" with similar devices and/or tracking methods;
- Social content such as Twitter feeds, instant messaging, and/or Facebook updates;
- Other online content such as newspaper articles, horoscopes, stock, traffic, sports and/or weather reports, RSS feeds, comics, crossword puzzles, classified advertisements, and websites; and
- Email messages and calendar schedules.

For the avoidance of doubt, it should be understood that the aforementioned examples are provided for exemplary or illustration purposes and are not intended to limit the scope of data that may be transmitted, received, calculated and/or displayed by the device, nor any intermediate processing that may employed during such transfer and display.

Notably, predetermined or selected content may be delivered according to different contexts. For example, in the morning, news, traffic and weather reports may be displayed along with the user's sleep data from the previous night. In the evening, a daily summary of the day's activities may be displayed. Notably, sleep and activity may be monitored and derived from a separate device (for example, Fitbit Tracker), manual log entries on a website, etc.—not the biometric monitoring device. Such information, however, may be communicated to, for example, the user and/or the Internet via the biometric monitoring device.

In addition thereto, or in lieu thereof, the aforementioned data and content may also be presented to the user through user interface 14 (for example, one or more displays other than the display incorporated in the biometric monitoring device). Indeed, such data and content may be presented in any form now known or later developed; all of which are intended to fall within the scope of the present invention. For example, a website, mobile phone application, or program operating on a personal computer. (See, for example, FIGS. 7A-7D which provide illustrative examples of biometric data measured by the biometric monitoring device and displayed on a website accessed via, for example, the Internet). Notably, other data obtained from other devices or input mechanisms (e.g., manual data entry) may be overlaid on the data from said biometric monitoring device. These include user activity levels, calorie burn, sleep quality and duration, water intake, etc. Furthermore, as a motivational tool, the user's biometric data may be used to rank users against each other (e.g., a "leaderboard" composed of friends in a social network) by, for example, recent weight lost, cumulative weight lost, and/or other progress toward a biometric goal. New "friends" and/or social groups may likewise be recommended to the user based on the user's profile, biometric goals (e.g., weight loss goal), and/or biometric data (e.g., progress toward weight loss goal). Virtual badges may be rewarded to the user for progress toward biometric goals such as lifetime weight loss.

As discussed above, the biometric monitoring device may identify the user via a number of techniques including detection based on a separate device ((for example, the Fitbit Tracker portable activity monitoring device) which communicates with the biometric monitoring device and identifies a unique/particular user via data transfer from the activity monitoring device to the biometric monitoring device), speech recognition, audio pattern classification and/or other biometric signature (for example, a toe, foot and/or finger print). The biometric monitoring device may also employ physiologic conditions or information to detect the user—for example, matching a weight, heart rate, bioelectrical impedance analysis signals and/or body fat to particular user data/information. The dynamic weight fluctuations and imbalance on the scale surface as measured by the load cells may also provide a unique signature for the user when she steps on the biometric monitoring device. A user's step sequence onto the biometric monitoring device may also assist in automated user identification: two users with similar characteristics may be distinguished by the fact that one steps on the device with the left foot first and the other with the right foot first. Indeed, in such cases, the users may also be coached by the biometric monitoring device to step first with either the left or right foot in order to facilitate user recognition.

Moreover, selection may be implemented manually by inputting a particular user via user interface 14. That is, the user may be identified by selection via buttons, touchpad, switches, etc. The biometric monitoring device may employ any circuitry and/or technique to automatically or manually identify the user whether now known or later developed; all such circuitry and techniques are intended to fall within the scope of the present inventions.

As noted above, the biometric monitoring device of the present inventions may be programmed or configured on a user, group and/or a global basis. In this regard, the biometric monitoring device may be customizable and programmable on an individual user basis as well as a global basis. For example, in one embodiment, the biometric monitoring device may run modular pieces of software (i.e., "apps") that perform a variety of functions/operations such as displaying the weather report, analyze weight/activity/food data to provide user coaching, etc. Furthermore, the data that is displayed to the user is configurable: the user may personalize (for example, user inputs) the physiologic data, historical graphs, web content (for example, weather or traffic information), etc. that are displayed and furthermore configure other parameters that control the display of the biometric monitoring device.

Figure 9A:
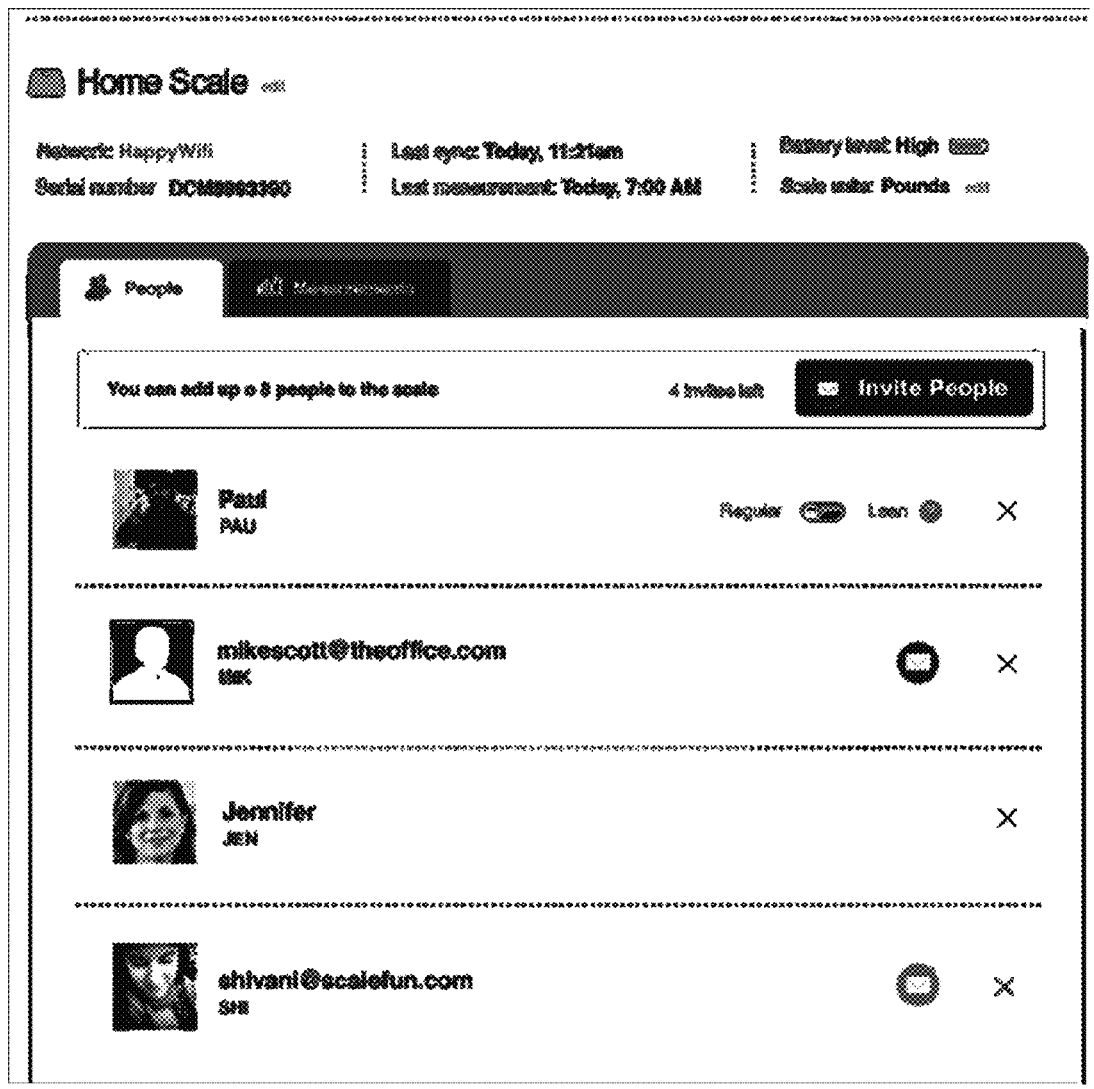
FIG. 9A-G illustrative exemplary website-based and/or mobile phone user interfaces to control, interface and/or review settings and authorized users for the biometric monitoring device, according to at least one embodiment of the present inventions; notably, as depicted in FIG. 9A, a user of the biometric monitoring device may have administrative access to invite other users, delete other users, change device settings, etc., but are not able to view personal information (e.g., weight measurements) for users other than their own; indeed, this administrative access model is adapted for situations in which multiple users share the device.
Figure 9B:
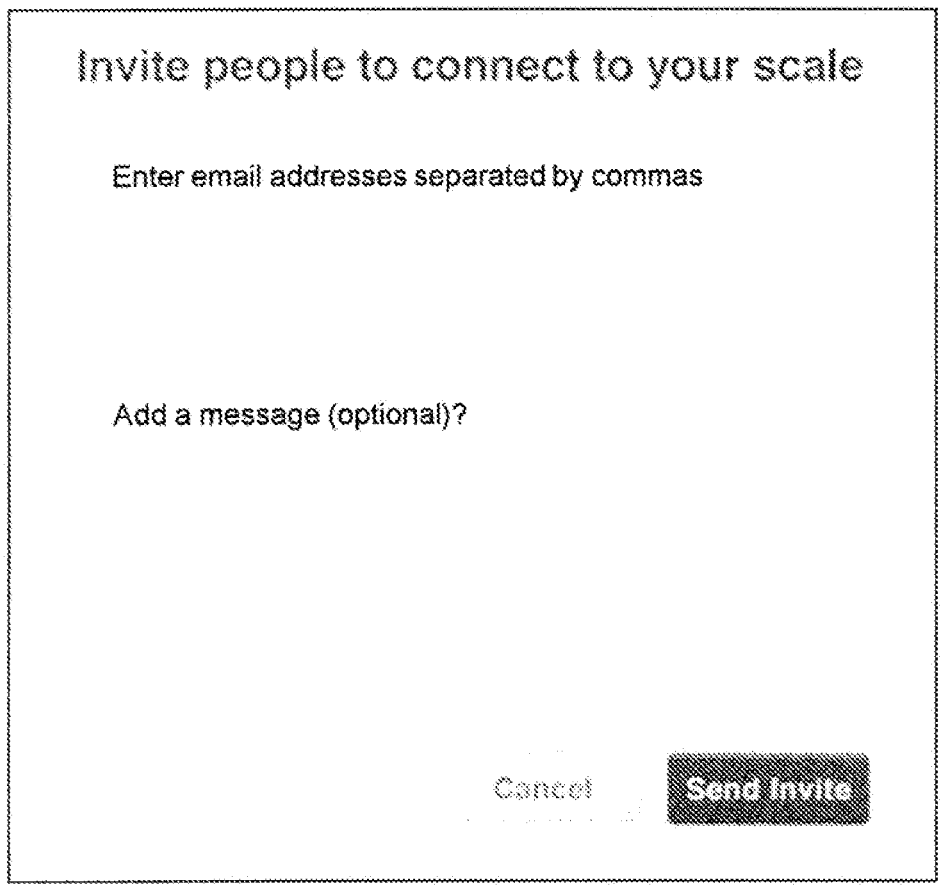
Figure 9C:
Figure 9D:
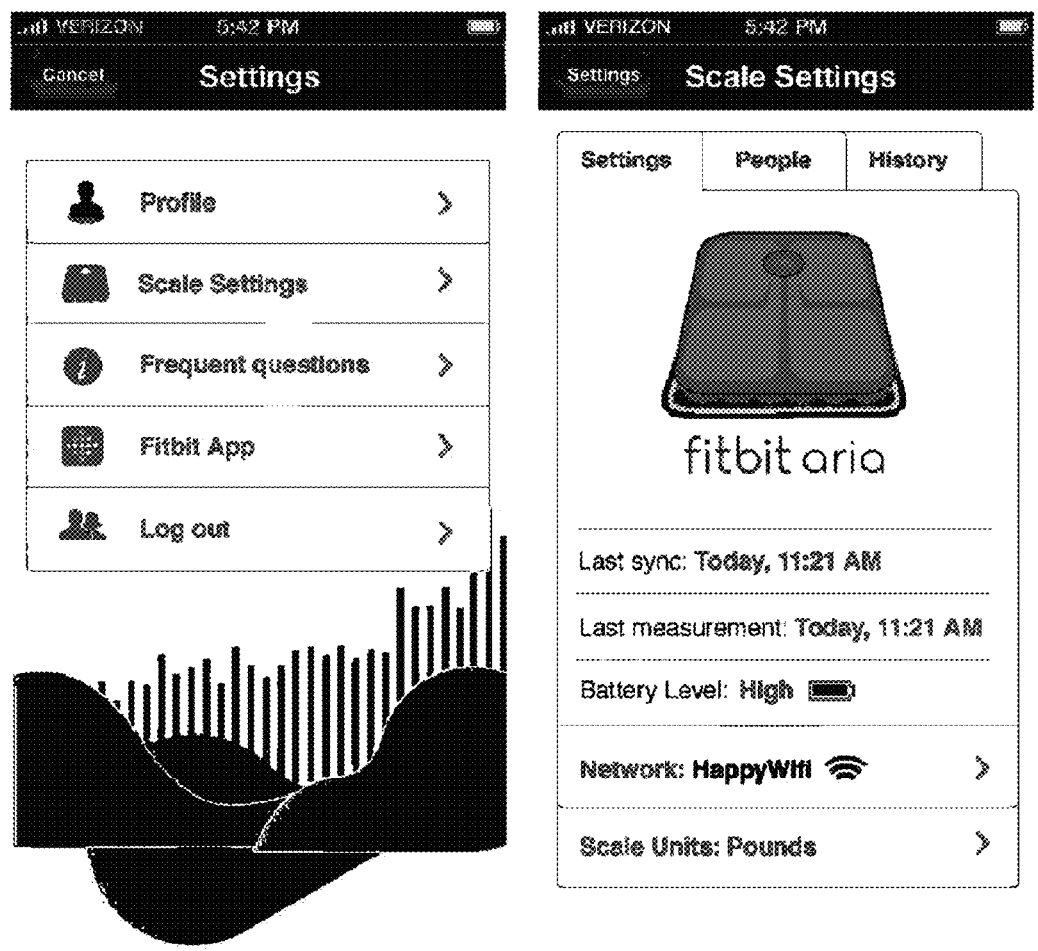
Figure 9E:
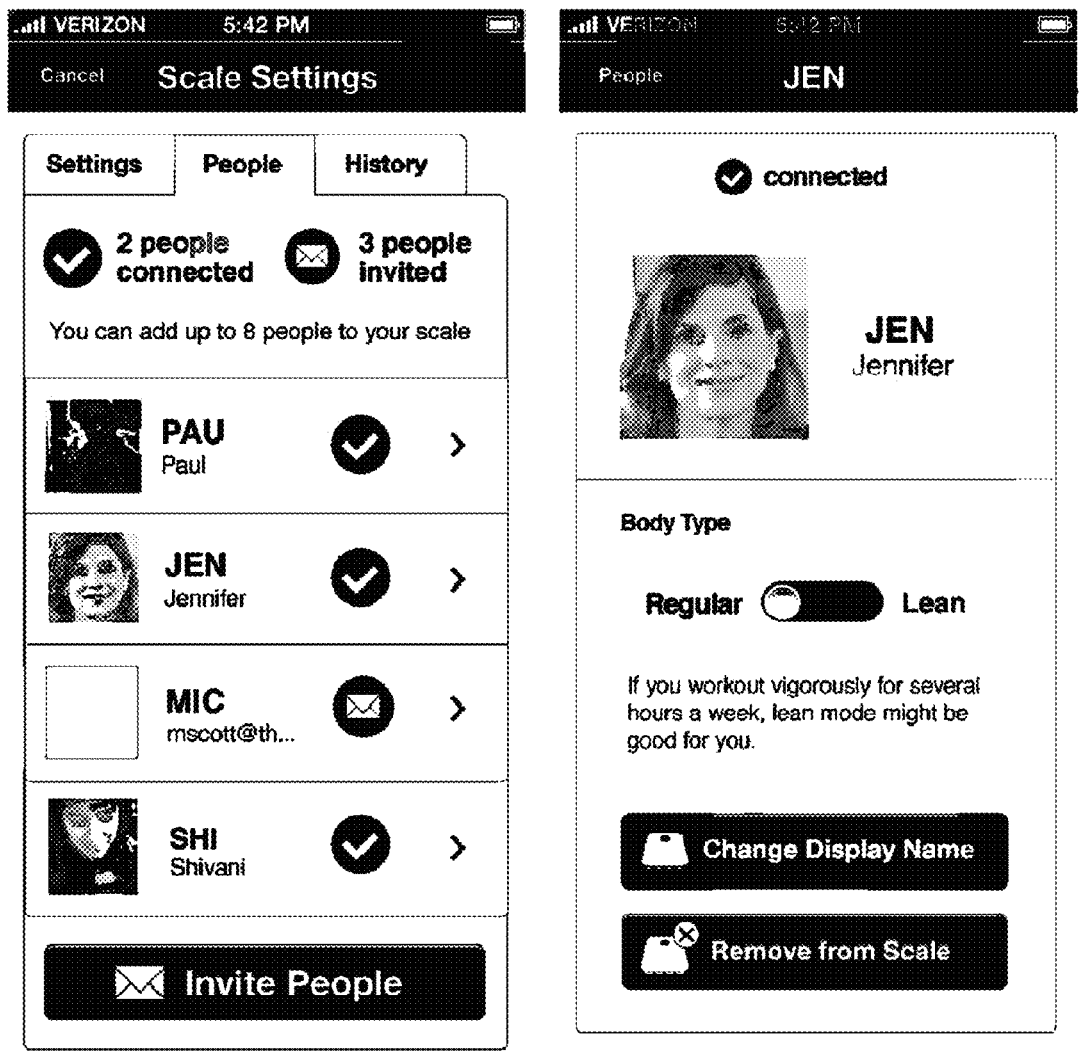
Figure 9F:
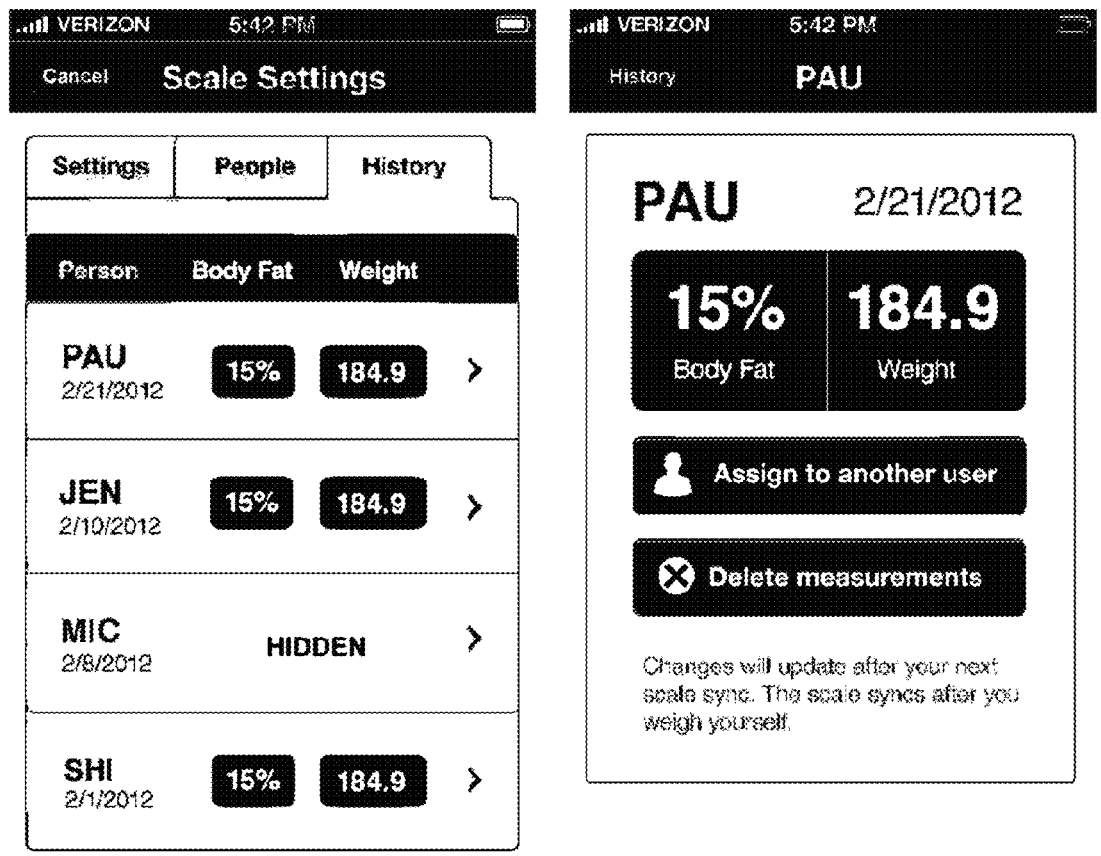
Figure 9G:
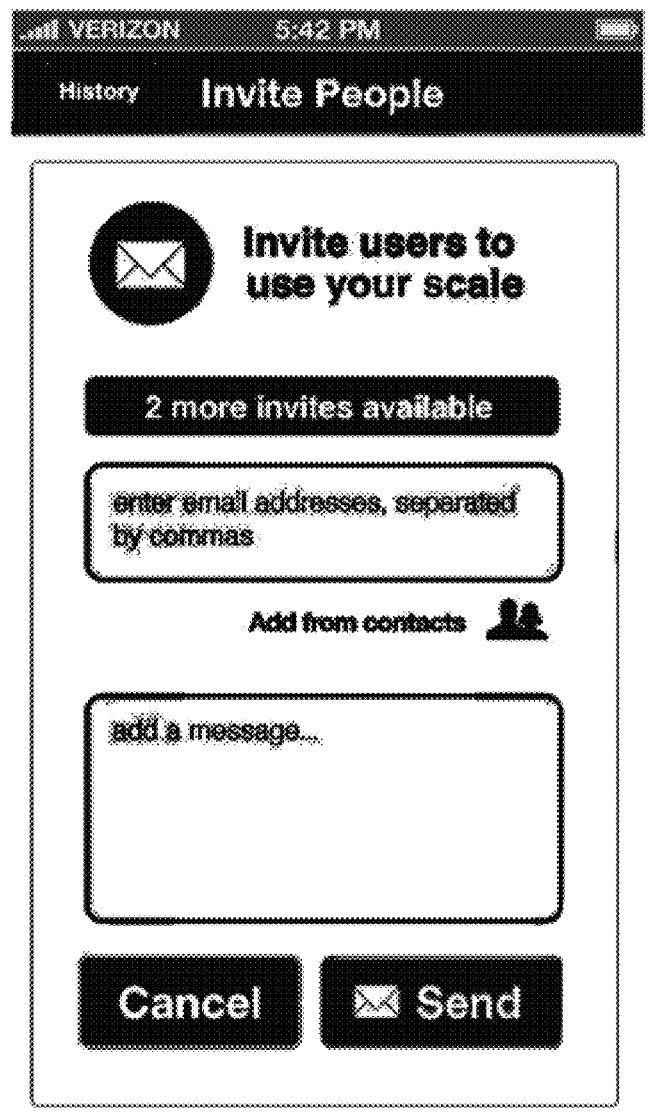

Programming or customizing may be implemented via the user interface, an external device via communication circuitry 18 (for example, via wired or wireless connection to a computer or personal computing device) and/or through a web interface (e.g., www.fitbit.com) on the user interface of the biometric monitoring device. In a preferred embodiment, the setup of the biometric monitoring device for a first user is accomplished without any wired communication. FIGS. 8A-M depicts exemplary processes where the initial setup of the device for a single user is accomplished by a client application or web browser running on a secondary device, for example, a personal computer or mobile phone. Network credentials, for example WiFi SSID and password, that are stored on the secondary device may be transferred to biometric monitoring device 10 without the need for the user to manually enter this information by way of switching the secondary device to the network broadcast by biometric monitoring device 10. FIGS. 9A-G provide illustrative examples of website-based and/or mobile phone user interfaces to control the settings and authorized users for biometric monitoring device 10. Notably, as depicted in FIG. 9A, a user of biometric monitoring device 10 may have administrative access to invite other users, delete other users, change device settings, etc., but are not able to view personal information (e.g., weight measurements) for users other than their own. This administrative access model is well adapted for situations in which multiple users share the device. In another embodiment, a single user or subset of users have administrative privileges.

Similarly, the firmware loaded on biometric monitoring device 10 may be updated and configured by the user through communication circuitry 18 (for example, via wireless connection). Indeed, functions and features of biometric monitoring device 10 (for example, certain sensors or data processing) as described here may also be modified, enabled and/or disabled (for example, on an individual, group or global basis).

In another aspect of the present inventions, biometric monitoring device 10 includes one or more environmental sensors to detect, measure and/or sense ambient environmental conditions. (See, for example, FIGS. 10A-10C). In this embodiment, the one or more environmental sensors may detect, measure and/or sense, for example, ambient pressure, temperature, sound, light, humidity, location and/or atmosphere. In response thereto, biometric monitoring device 10, in addition to monitoring, calculating, determining and/or sensing one or more aspects of the physiological state, condition or data of a user, may provide status information to the user and/or control or operate local external devices and/or appliances.

With reference to FIG. 11, the environment sensors may include one or more audio sensors to detect, measure and/or sense ambient sounds (for example, use of the shower, bath, sink or toilet), one or more humidity sensors to detect, measure and/or sense the ambient humidity, one or more pressure sensors to detect, measure and/or sense the ambient pressure, one or more temperature sensors to detect, measure and/or sense the ambient temperature, one or more atmospheric sensors to detect, measure and/or sense odors, air quality, pollen count, carbon dioxide, etc., GPS circuitry to sense location of biometric monitoring device 10.

In operation, biometric monitoring device 10 may detect, monitor and/or sense ambient environment conditions and/or use, control or operate local appliances, devices and fixtures in the local environment surrounding biometric monitoring device 10. For example, if biometric monitoring device 10 is located in the bathroom, it may detect, measure, monitor and/or sense an individual and/or overall household use of the shower/bathtub, sink, and toilet. In this way, biometric monitoring device 10 may obtain data and generate metrics such as the number and duration of showers/baths, total time spent in the bathroom, number of visits to the bathroom, number of toilet flushes, number and type of various bodily functions, number and duration of teeth brushing, duration of sink use, estimated power consumption from light fixtures, estimated water usage from the sink, toilet, and shower/bath individually or in total, and/or control external devices or mechanisms to impact the environment conditions (for example, enable/disable a fan to control temperature and/or humidity). These metrics may be determined on an individual, group and/or a global basis (for example, an entire household or locker room basis).

The biometric monitoring device 10 having environmental sensors may employ processing circuitry to analyze data from the environmental sensor(s). (See, FIGS. 12A and 12B). Such processing circuitry may be similar to processing circuitry 16 discussed above in connection with biometric monitoring device 10 embodiments having physiological sensors.

Where biometric monitoring device 10 also includes communication circuitry to provide one-way or two-way communication to the Internet and/or external devices and/or appliances (see, for example, FIGS. 6A-6D), biometric monitoring device 10 may upload physiological and/or environmental data to or download data from, for example, non-local data storage and/or selected third parties. In this way, biometric monitoring device 10 may manually or automatically provide physiological and/or environmental data to such data storage and/or third parties. As noted above, biometric monitoring device 10 may also receive data and/or instructions/comments, for example, health or training guidance or feedback via biometric monitoring device 10. For example, such third parties (for example, health professionals or trainers) may monitor and/or provide feedback based on such physiological and/or environmental data. In this way, such third party or parties may provide periodic, continuous and/or intermittent monitoring and/or feedback, notwithstanding, for example, the user/patient is substantially remote or distant from such third parties, or where significant monitoring of the user/patient is not feasible or convenient.

Notably, the discussion herein with respect to communication, including circuitry therefor and techniques thereof, is applicable to and may be employed with those biometric monitoring device embodiments having environment sensors; for the sake of brevity, such discussions will not be repeated.

In those embodiments where the environmental sensors include an audio sensor, processing circuitry 16 may include statistical classifiers of sound to differentiate, determine and/or sense between different users and activities. The audio sensor may be mounted to biometric monitoring device 10 so as to sample ambient noise or affixed to the scale so as to be receptive to sounds transmitted through the ground (i.e., using the ground as a sound board).

In another embodiment, one or more "smart" beacons may be disposed on one or more of the fixtures of interest to "communicate" usage and status with biometric monitoring device 10. In addition thereto, or in lieu thereof, biometric monitoring device 10 may also include humidity, temperature, passive infrared (PIR), visible light, barometric pressure, sonar, radar, and/or laser range finding sensors individually or in combination to enable this functionality. Based on such data, biometric monitoring device 10 may control external devices or mechanisms to adjust, control or impact the local or ambient environment (for example, enable/disable a heating source, air conditioning source and/or fan to adjust the temperature or humidity of the ambient environment). In this way, metrics of the environment may be monitored and, in certain embodiments, aspects of the ambient controlled (for example, temperature and humidity adjusted via control of local equipment).

In yet another exemplary embodiment, the environmental sensor includes an atmospheric sensor to detect, measure and/or sense to acquire data which is representative of air quality, pollen count, carbon dioxide, etc. In this way, metrics of the environment may be monitored and, in certain embodiments, aspects of the ambient controlled.

To that end, as noted above, processing circuitry 16 may include control circuitry to control or program room activity. For example, biometric monitoring device 10 may, in response to detecting the presence of a user, enable a "night light" when advantageous (for example, in the evening when other lighting is disable). The illumination device of the "night light" may be disposed internal or external to biometric monitoring device 10. Where the illumination device is external, the functionality may be achieved by controlling one or more external light fixtures. Where the illumination device is disposed or integrated in the platform or housing of biometric monitoring device 10, the functionality may be achieved by controlling one or more onboard lights. (See, for example, FIG. 1D). Indeed, biometric monitoring device 10 may also directly control the light levels in the room by communicating with the lighting (integrated and/or external) and/or window coverings. In addition, the control circuitry may engage environment control equipment (for example, heating, ventilation, air conditioning and/or humidifying or dehumidifying equipment) to control, adjust and/or manage the ambient environmental conditions (for example, temperature and humidity).

In another embodiment, circuitry of biometric monitoring device 10 may detect the teeth brushing activity and, upon detecting the conclusion, turn on the sink faucet and/or thereafter off. The circuitry may control the sink faucet water flow before, during and after teeth brushing activity. Indeed, the circuitry of biometric monitoring device 10 may also be programmed to detect and control the use of water flow of the shower/bath—for example, after a certain amount of time has elapsed with use of the shower water, biometric monitoring device 10 may audibly warn the user and/or eventually turn off the water in an effort to control or conserve water usage.

In addition thereto, or in lieu thereof, circuitry of biometric monitoring device 10 may, in response to detection of certain odors or after identification of particular bathroom activities (for example, use of the shower or toilet), or after a detecting the user exiting the room, enable a dispenser of a counter-order (for example, air freshener sprayer), ventilation equipment and/or air conditioning equipment to maintain and/or control the atmospheric status and/or odor of the ambient environment.

In another embodiment of the present inventions, biometric monitoring device 10 may include circuitry or other mechanisms to adjust the temperature of the surface engaged by the user (for example, heat the top surface of biometric monitoring device 10) to provide a more comfortable temperature, which is preferably a temperature close to body temperature. Where the surface engaged by the user is glass, this may be achieved by one or more heating elements that are disposed beneath or in the glass (for example, beneath the surface engaged by the user. They may be controlled to a specific temperature by actively monitoring the temperature of the glass, or they may be heated in an open loop manner with no active sensing of the temperature of the glass. In one embodiment, the biometric device may include circuitry to enable heating wherein such circuitry may be programmed to enable the heating elements at one or more program or specific times (e.g., in the morning a predetermined time (for example, 10 minutes) prior to a user's routine weigh-in). In another embodiment, heating may triggered by a button push or other user interface command (e.g., on the biometric device or via a mobile phone app).

Notably, biometric monitoring device 10 may be employed in other local environments (for example, other rooms of a premise). For example, where biometric monitoring device 10 is disposed or located in living, family or TV room, biometric monitoring device 10 may monitor, control and/or track usage of the television, playing video games, and/or computer. In this embodiment, processing circuitry 16 may employ one or more of the environmental sensors described herein (using methods similar to those described herein). Indeed, biometric monitoring device 10 may be employed in any room in a standard household setting (e.g., dining room, bed room, study) and perform functions specific to its location. It may automatically detect which type of room it is in or it may be configured by the user to be a specific room.

In one embodiment, biometric monitoring device 10 includes a geolocation identification device or component (for example, GPS, mobile telephone and/or altimeter). In this embodiment, the geolocation identification device facilitates locating biometric monitoring device 10 on the Earth, which may, for example, facilitate calibration or accuracy enhancement in connection with the ambient gravitational constant. In another embodiment, the geolocation identification device/component of a biometric monitoring device allows a user to log, monitor and/or track trips or visits. Such a configuration may allow businesses to more accurately track employee routes (for example, in connection with deliveries) or an individual to log, monitor and/or track trips or visits to a gym, store or friend's house.

Thus, in these embodiments, biometric monitoring device 10 may also include the environmental sensor(s) in addition to physiological sensor(s). Notably, all permutations and combinations of sensors (physiological and environmental) may be employed or implemented in a biometric monitoring device according to the present inventions. All such combinations and permutations are intended to fall within the scope of the present inventions.

There are many inventions described and illustrated herein. While certain embodiments, features, attributes and advantages of the inventions have been described and illustrated, it should be understood that many others, as well as different and/or similar embodiments, features, attributes and advantages of the present inventions, are apparent from the description and illustrations. As such, the above embodiments of the inventions are merely exemplary. They are not intended to be exhaustive or to limit the inventions to the precise forms, techniques, materials and/or configurations disclosed. Many modifications and variations are possible in light of this disclosure. It is to be understood that other embodiments may be utilized and operational changes may be made without departing from the scope of the present inventions. As such, the scope of the inventions is not limited solely to the description above because the description of the above embodiments has been presented for the purposes of illustration and description.

Figure 13C:
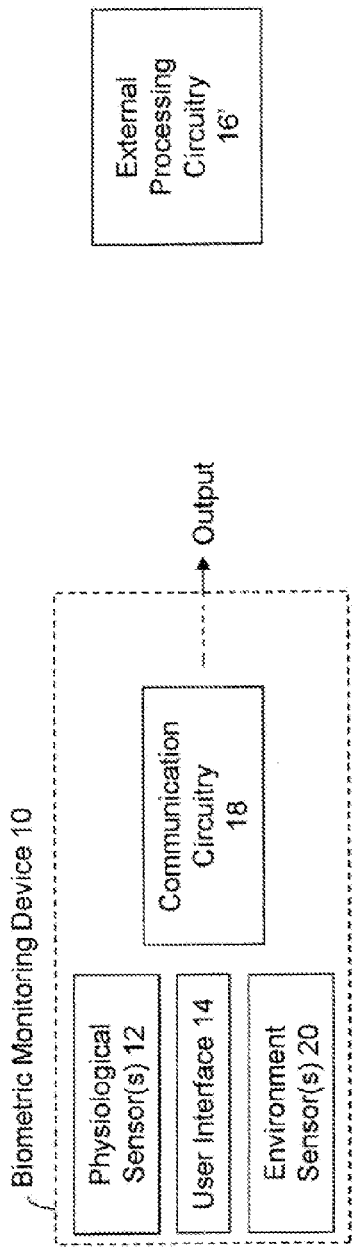
FIG. 13C is a block diagram representation of an exemplary biometric monitoring device including one or more physiological sensors and one or more environment sensors, according to at least certain aspects of certain embodiments of the present inventions, wherein external processing circuitry calculates or determines physiologic information of the user and/or ambient environmental information based on or using sensor data of the biometric monitoring device.

For example, as noted above, processing circuitry 16 may include control circuitry to implement the control operations described herein—including, for example, control of on-device circuitry and sensors, external circuitry and devices and/or external local appliances. The control circuitry of processing circuitry 16 may be implemented via discrete or integrated logic, and/or may include one or more state machines, processors/controllers (suitably programmed) and/or field programmable gate arrays (or combinations thereof); indeed, any circuitry (for example, discrete or integrated logic, state machine(s), processor(s)/controller(s) (suitably programmed) and/or field programmable gate array(s) (or combinations thereof)) now known or later developed may be employed to control, for example, on-device circuitry and sensors, external circuitry and devices and/or external local appliances is intended to fall within the scope of the present inventions;

In addition, in one embodiment, biometric monitoring device 10 of the present inventions may not include processing circuitry to monitor, calculate, determine and/or detect physiologic information, condition and/or state of the user (for example, a human or non-human animal). In this embodiment, some or all of the monitoring, calculating, determining and/or detecting may be implemented "off-device" or external to biometric monitoring device 10. Here, biometric monitoring device 10 may store and/or communicate data which is representative of the physiologic information, condition(s) and/or state(s) of the user to external processing circuitry wherein such external processing circuitry may monitor, calculate, determine and/or detect physiological condition of the user. (See, FIGS. 13A and 13C). Such external circuitry may implement the calculation processes and techniques in near real-time or after-the-fact. The data which is representative of the physiological condition(s) and/or state(s) of the user (as represented by the data of physiological sensor(s) 12) may be communicated to such external processing circuitry, for example, via transmitter circuitry, removable memory, electrical or optical communication (for example, hardwired communications via USB). Importantly, such an architecture/embodiment is intended to fall within the scope of the present inventions.

As discussed herein, physiological sensor(s) may sense, detect, assess and/or obtain data which is representative of physiologic information of the user (for example, weight, body fat, blood pressure, pulse rate, blood sugar and the waveform shape corresponding to the heart beat).

Figure 13D:
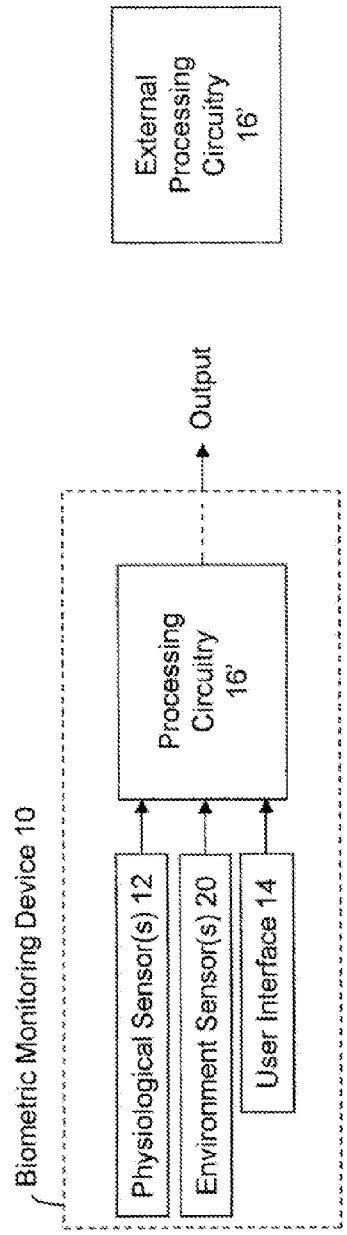
FIG. 13D is a block diagram representation of an exemplary biometric monitoring device, according to at least certain aspects of certain embodiments of the present inventions, wherein the biometric monitoring device includes certain processing circuitry and certain other processing circuitry is external to the biometric monitoring devices—wherein the internal and external processing circuitry, in combination, calculates or determines physiologic information of the user and/or ambient environmental information based on or using sensor data of the biometric monitoring device.

Moreover, biometric monitoring device 10 of this embodiment (i.e., external processing circuitry) may include all permutations and combinations of sensors (for example, one or more physiological sensor(s). Notably, in one embodiment, processing circuitry 16 to monitor, calculate, determine and/or detect physiologic information, condition and/or state of the user may be distributed between resident (on-device) circuitry and external (off-device) circuitry. (See, FIGS. 13B and 13D). In this embodiment, circuitry disposed in biometric monitoring device 10 may implement certain processes and algorithms and the external processing circuitry may implement other processes and algorithms wherein, the circuitry, in combination, monitors, calculates, determines and/or detects physiologic information, condition and/or state of the user.

Figure 14:
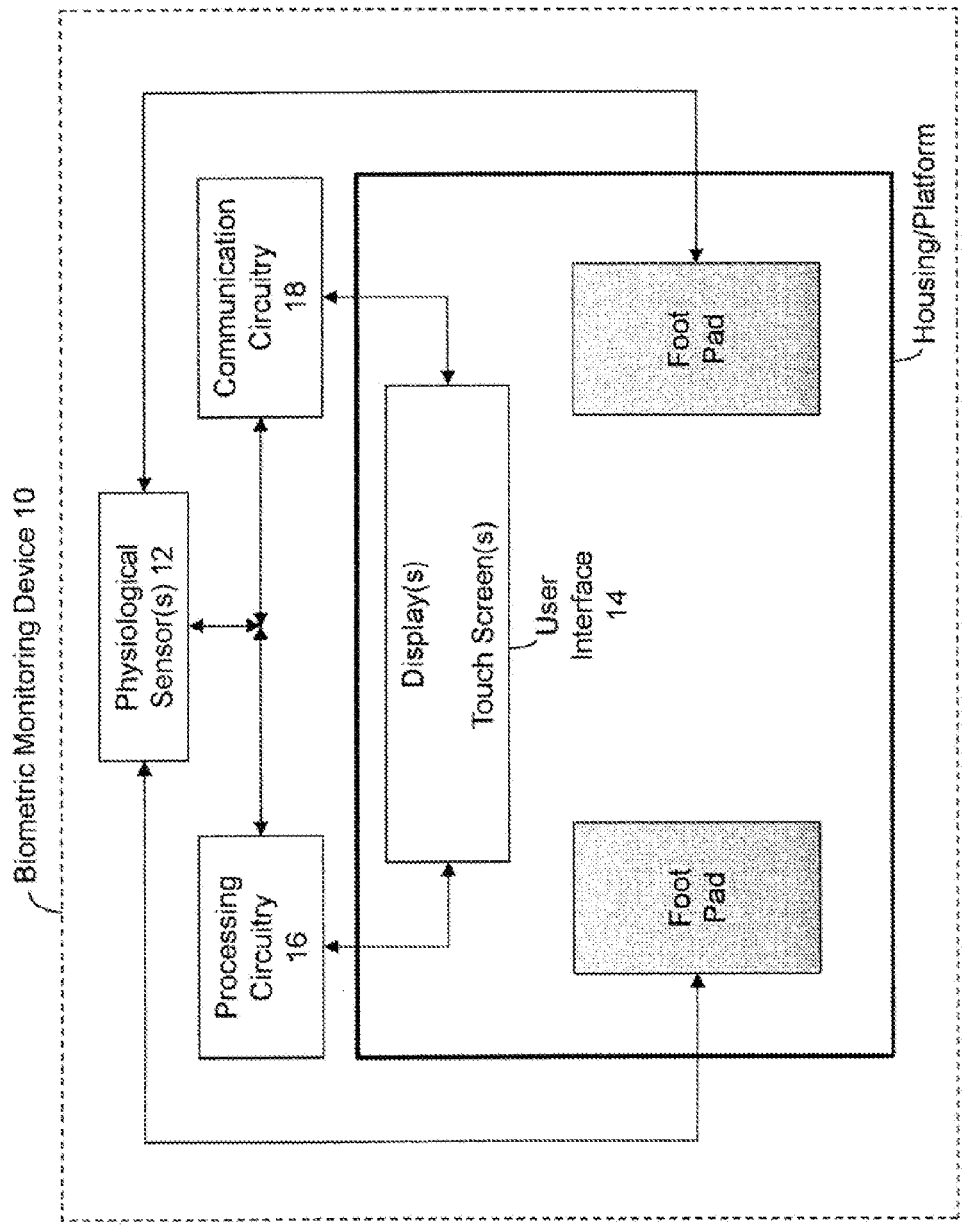
FIG. 14 is an exemplary biometric monitoring device for calculating and/or determining the weight of a user, according to at least certain aspects of certain embodiments of the present inventions, wherein the exemplary biometric monitoring device includes footpads, user interface (having one or more displays and one or more touch screens), processing circuitry for calculating or determining physiologic information (including the user's weight) of the user, and communication circuitry for (wireless and/or wired) transmission of physiologic data and/or receipt of physiologic data and/or web content, news, traffic, weather, social content (for example, instant messaging), advertisement, emails, calendar schedule, diet coaching content, instructions and/or data, and goal oriented information (for example, a user's progress toward biometric goals (weight, body fat composition, caloric consumption, activity and/or sleep)) as well as biometric information including, for example, current information, historical information and/or current information in view of historical information.

With reference to FIG. 14, in an exemplary embodiment, biometric monitoring device 10 includes physiological sensors including weight, body fat, hydration, heart rate, respiratory rate, blood pressure and/or arterial stiffness sensors, wholly or partially disposed, incorporated and/or embedded in foot pads. Physiological sensors 12 are electrically coupled to processing circuitry (which may also include control circuitry to control the operations of biometric monitoring device 10). As discussed above, processing circuitry 16 calculates, assesses and/or determines physiologic information using data sensed, detected and/or measured from physiological sensors 12. In this embodiment, processing circuitry 16 may calculate the user's weight as well as one or more of the user's body fat, hydration, heart rate, respiratory rate, blood pressure and/or arterial stiffness.

The communications circuitry (wireless and/or wired) transmit biometric or physiologic data to one or more external devices (for example, via the Internet) and/or receive, for display via user interface 14, web content, news, traffic, weather, social content (for example, instant messaging), advertisement, emails, calendar schedule, exercise or diet coaching, instructions and/or data, and goal oriented information (for example, a user's progress toward biometric or physiological goals (weight, body fat composition, caloric consumption, activity and/or sleep)) as well as biometric or physiologic information including, for example, current information, historical information and/or current information in view of historical information. Thus, as noted above, communication circuitry 18 of biometric monitoring device 10 of the present inventions may facilitate or provide external connectivity to, for example, the Internet and/or local external devices and/or appliances. The communication circuitry 18 may also facilitate operation, programming and/or control of such local external devices and/or appliance.

With continued reference to FIG. 14, the user interfaces may employ any input/output devices now known or later developed including such input devices as touch screens and displays. The user interface may also include motion sensors, biometric sensors and/or proximity sensors (not illustrated). The touch screen may be employed to identify, determine and select a particular user and/or user profile (for example, set-up of biometric monitoring device 10).

Although not illustrated, user interface 14 of the exemplary biometric monitoring device illustrated in FIG. 14 may also include one or more biometric sensors (for example, speech recognition, audio pattern classification and/or toe print detector) to identify or determine a particular user and/or a touch screen to facilitate selection of a particular user or user profile. In response thereto, biometric monitoring device 10 may, in addition to correlating the current physiologic data with the particular user, present the associated historical information to the user via visual and/or audio techniques of user interface 14.

In addition thereto, or in lieu thereof, communication circuitry 18 may also be employed to detect or identify a particular user. In this regard, communication circuitry 18 acquires information from a separate/external personal device that is unique to the user (for example, Fitbit's activity monitoring/tracking device). In this way, biometric monitoring device 10 determines or identifies a particular user based on signals or signature from the external personal device.

Figure 15B:
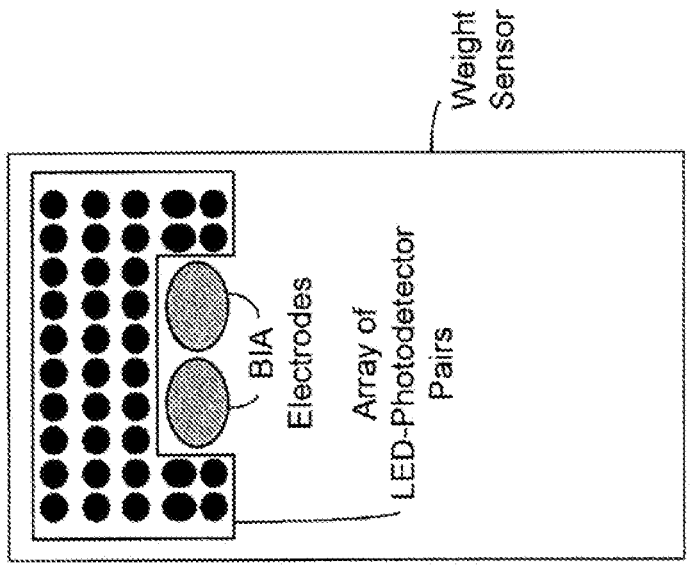
Figure 15A:
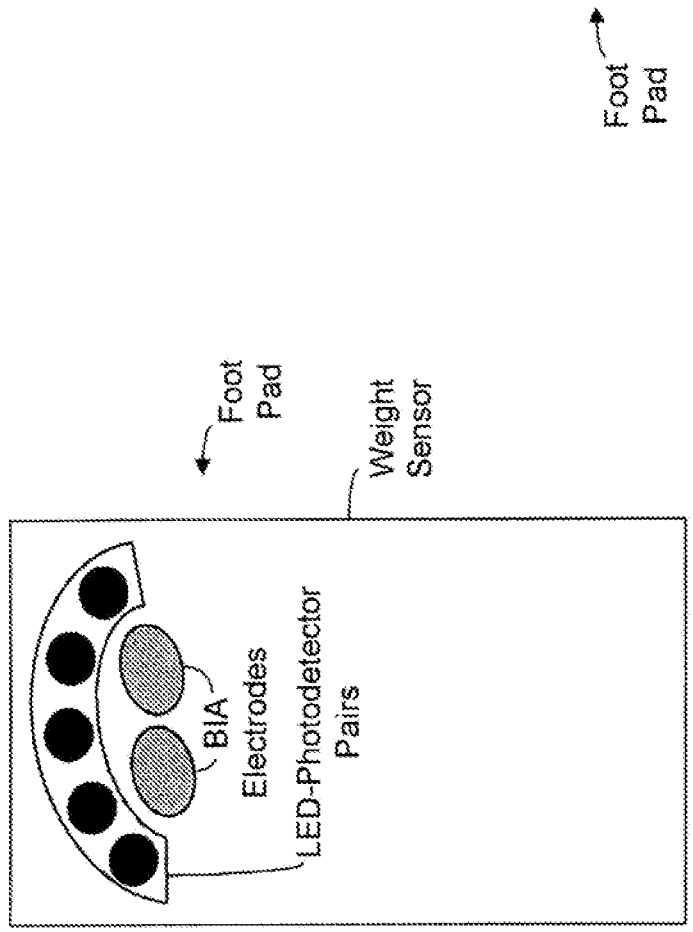
Figure 16A:
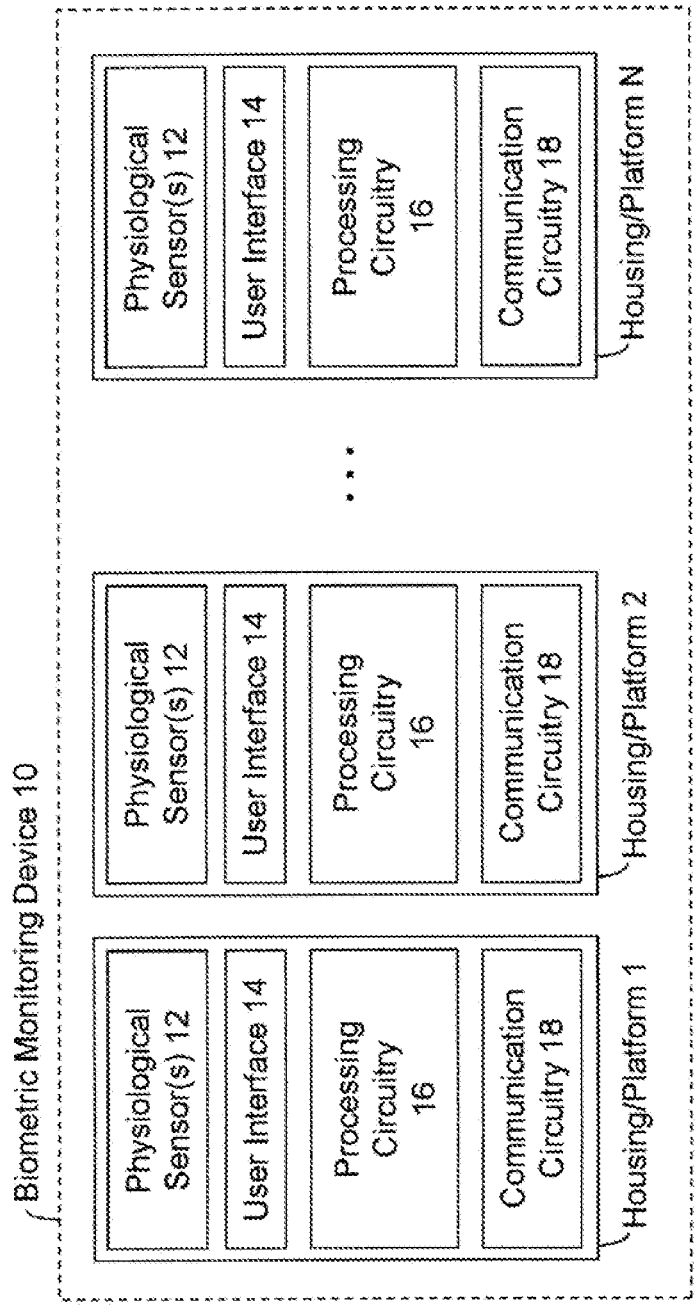
FIGS. 16A-16D are block diagram representations of exemplary biometric monitoring devices having a plurality of components disposed in or dispersed among a plurality of platforms/housings, according to at least certain aspects of certain embodiments of the present inventions, wherein the biometric monitoring devices, according to at least certain aspects of certain embodiments of the present inventions, includes one or more physiological sensors (for example, a weight sensor/scale) and user interface, and, in certain embodiments, may also include processing circuitry and/or communication circuitry; notably, the components, elements and/or circuitry of the biometric monitoring device may be disposed or integrated in or on one platform/housing or may be disposed or integrated in or on a plurality of platforms/housings (which are interconnected, for example, mechanically, electrically and/or optically); the present inventions are not limited to components, elements and/or circuitry of the biometric monitoring device disposed on or in one platform/housing but may be dispersed among a plurality of platforms/housings; indeed, all permutations and combinations of features, elements and/or circuitry of the biometric monitoring device (as described herein), whether integrated in conjunction with one platform/housing and or dispersed among a plurality of platforms/housings, are intended to fall within the scope of the present inventions.
Figure 16C:
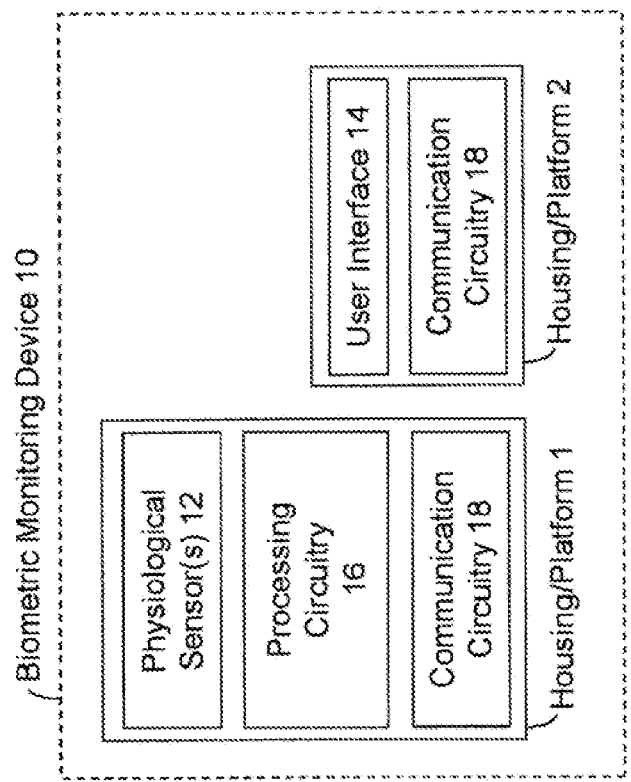
Figure 16B:
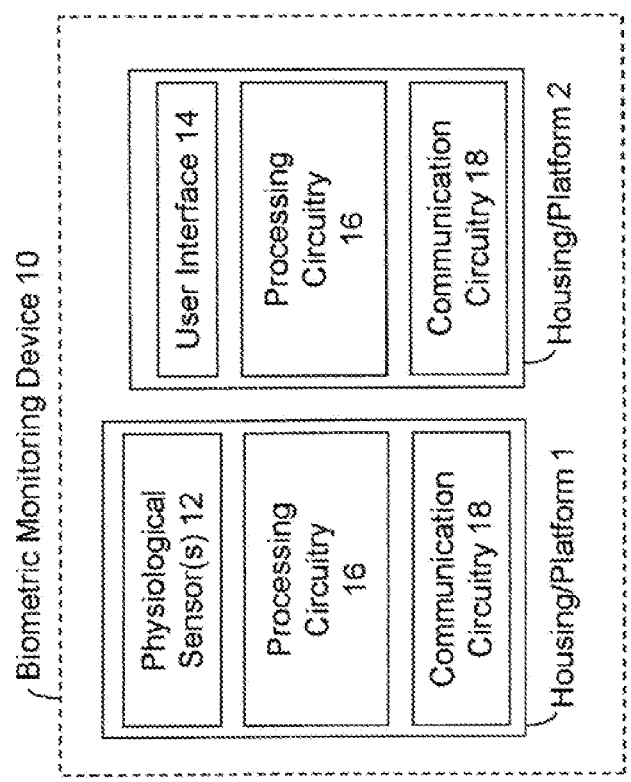
Figure 16D:
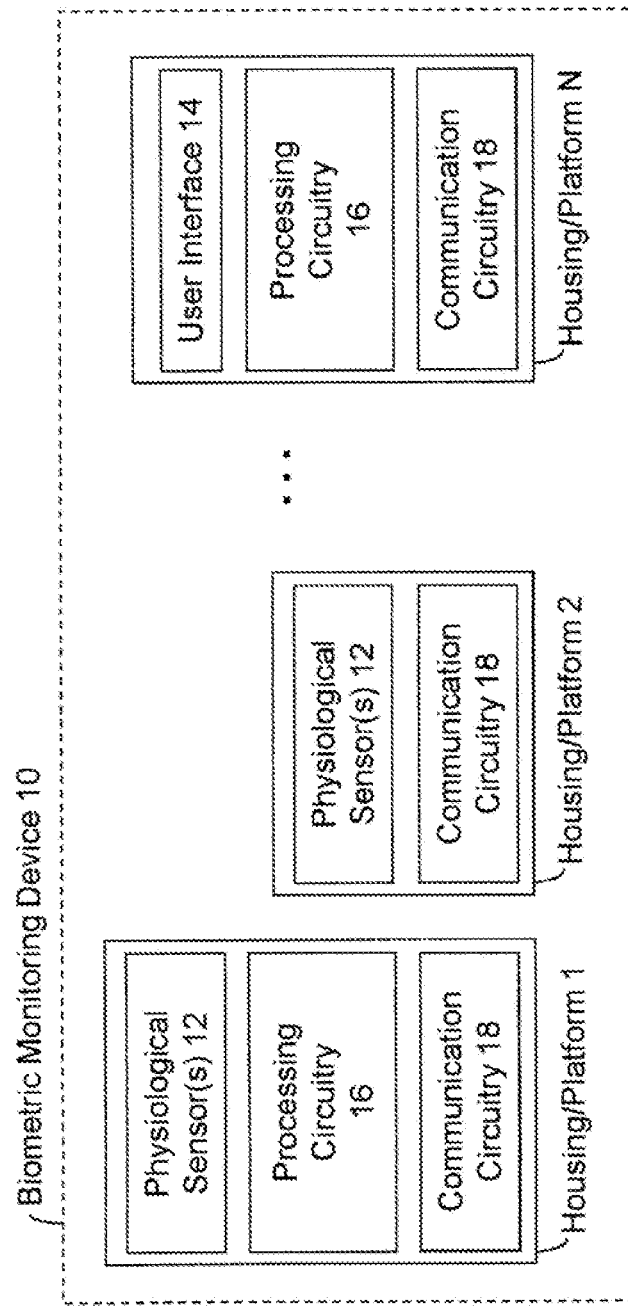

In one embodiment, in operation, processing circuitry 16 calculates or determines the user's weight based on or using data from the weight sensor incorporated and/or embedded in foot pads. (See, FIGS. 15A-15D). In addition, processing circuitry 16 may employ the data from a body fat sensor (in this illustrative embodiment, the bioelectrical impedance analysis (BIA) electrodes), to calculate or determine a user's body fat composition and/or body mass index. In this regard, via the BIA electrodes, a small current is applied to the body and the characteristics of the return current measured in the electrodes are representative of the body fat composition of the user. The processing circuitry, based on data acquired or detected by the BIA electrodes and user information (e.g., height, age, and gender), calculates or determines a user's body fat composition and/or body mass index With continued reference to FIGS. 15A-15D, the foot pads also include one or more LED/photo detector pairs disposed therein such that when the user placing blood-perfused area of the foot (for example, the big toe) over the one or more LED/photo detector pairs, biometric monitoring device 10 may implement or perform photo plethysmography to calculate, assess and/or determine blood pressure and/or arterial stiffness. Notably, an array of LEDs-photo detectors may be employed to adaptively determine which location on the foot provides the best plethysmography signal. (See, FIGS. 15B and 15D). Using data from the LED/photo detector pairs, processing circuitry 16 may calculate, assess and/or determine other biometric or physiological quantities such as heart rate, blood pressure and/or arterial stiffness. That is, processing circuitry 16 may employ data from a heart rate sensor to calculate, assess and/or determine the user's heart rate using, for example, ballistocardiography. Based on the output of such sensors, processing circuitry 16 may calculate, assess and/or determine the user's heart rate and store and/or output such information (for example, to a display (user interface) or external to biometric monitoring device 10 via communication circuitry 18).

In one embodiment, processing circuitry 16 may also determine or calculate the size and shape of the user's foot via analysis of data from LED/photo detectors or multiple BIA. Such an embodiment generates and/or stores information regarding the size and shape of the foot as well as how the feet or foot engages the surface. In this way, for example, a parent may measure and track (over time) the change in size and shape of a child's foot as well as the manner in which the user stands (which may provide information as to how the foot/feet engage the surface as well as the shape of the legs and hips).

The biometric monitoring device 10 of FIG. 14 may be programmed or configured (for example, by the user via user interface 14 of biometric monitoring device 10 and/or an external device that communication with biometric monitoring device) to enable or engage (or disable or disengage) one or more physiological sensors and/or enable or disable the monitoring, calculating and/or determining of one or more physiological parameters (based on or using data from such sensors). In this way, the user may configure biometric monitoring device 10 to acquire selected physiologic data (via enabling and/or disabling selected physiological sensors) and/or calculate, monitor and/or determine selected physiological parameters (via enabling or disabling processing circuitry 16 accordingly). Such configuration may be on a user basis (each user includes his/her unique configuration) and/or on a device basis (the device is programmed into a particular configuration regardless of the user).

For example, as indicated above, where biometric monitoring device 10 includes a body fat sensor having electrodes for implementing BIA, it may be advantageous to disable such sensor where the user is pregnant or equipped with a pace maker. However, the body fat sensor may be enabled for male users or non-pregnant female users wherein for such users, processing circuitry 16 (which may include control circuitry as well) enables the body fat sensor and responsively calculates, assesses and/or determines the user's blood pressure and/or arterial stiffness (based on or using data from such sensor). Moreover, processing circuitry 16 may store body fat information for certain of the users and/or output such information (for example, display) thereto.

As noted above, the user may communicate with biometric monitoring device 10 via user interface 14, which may include, for example, a touch pad, touch screen, buttons, switches and/or knobs. The biometric monitoring device 10 may also be programmed to detect and/or interpret other user interaction schemes such as tapping, stepping on, or shifting the user's weight on the device may control biometric monitoring device 10, for example, the display. Certain physiological and/or environmental sensors of biometric monitoring device may be employed to input user commands and/or information. For example, biometric monitoring device 10 may include a plurality of BIA electrodes, photo detectors, and/or a camera which may be used to sense the motion of the foot or toes to control biometric monitoring device 10. Such sensors may provide resolution on the top of biometric monitoring device 10 that facilitate user inputs and interaction. For example, the user may "swipe" the foot across the device (for example, from the right side to left side of biometric monitoring device 10) to transition displays on biometric monitoring device 10, scroll through a list of user names, etc. This can be resolved with a plurality of BIA electrodes as a transient change in impedance across the array of electrodes. It may also be seen as a transient change in received light or color by an array of photo detectors and/or a camera. Similar methods may be used to determine the location of specific toe/foot/finger presses on the surface of biometric monitoring device 10 and may then be used to virtually produce or create buttons and icons that launch specific "app" or application functionality. Here, processing circuitry 16 may be employed to interpret such user inputs via resident sensors. In this way, the resident sensors are employed as a user interface.

In another embodiment, biometric monitoring device 10 may monitor the time between user weight measurements and provide notifications to the user to weigh-in via email, instant message, posting to the user's calendar scheduling program, etc. The biometric monitoring device itself may display specific notifications to invite the user to perform a weight measurement. Indeed, biometric monitoring device 10 may also employ user interface 14 to alert the user or capture the user's attention (for example, use its LEDs to glow/throb in specific ways to provide messaging, or play music or provide audio messages). The onboard or integrated notification device(s) may also be used to provide the user reminders, alerts, and notices on the use of other devices (e.g., the Fitbit Tracker) and for other online content (for example, www.fitbit.com, RSS feeds, incoming email).

Notably, the weight sensor of the present inventions may implement rapid or automatically "taring" or zero calibration. Briefly, by way of background, certain digital weight sensors require a period of non-use (up to a few seconds) wherein the sensor zeros itself. Thereafter, the sensor displays "0 lbs" or 0 Kgs" and is available for use. Other digital weight sensors include automatically "taring" or zeroing wherein there is no required period of non-use to zero calibrate the sensor.

In one embodiment, the weight sensor of the present inventions employs rapid zero calibration or taring. In this embodiment, the weight sensor continuously samples or periodically samples (for example, on 10 second intervals) its load cells and stores the sample values in memory (for example, a data buffer). The number of sample values stored in memory may be limited or fixed by sizing the memory or data buffer.

In operation, when the user steps onto the sensor, the load cell of the weight sensor will detect and/or sense a significant change thereby indicating the sensor is in use. The processing circuitry 16 may then use the sample values stored in memory to zero calibrate the weight sensor. For example, in one embodiment, processing circuitry 16 determines a zero point by averaging the values stored in memory (for example, all of the sample values). Alternatively, processing circuitry 16 may average the samples periodically and thereafter, processing circuitry 16 may average the averages of the sample values. In yet another embodiment, processing circuitry 16 may average only those samples that are within a certain percentage of a median value; samples that are outside the percentage are discarded. Notably, the present inventions may employ any processing technique now known or later developed to determine a zero point from the aforementioned samples.

Importantly, the present inventions are neither limited to any single aspect nor embodiment, nor to any combinations and/or permutations of such aspects and/or embodiments. Moreover, each of the aspects of the present inventions, and/or embodiments thereof, may be employed alone or in combination with one or more of the other aspects and/or embodiments thereof. For the sake of brevity, many of those permutations and combinations will not be discussed and/or illustrated separately herein.

Further, biometric monitoring device 10 may communicate with external circuitry using the transmitter circuitry (see, for example, FIGS. 1B, 1C, 5A, 5C, 10B and 10C), receiver circuitry (see, for example, FIGS. 1B, 1C, 5B, 5C, 10B and 10C), removable memory, electrical or optical communication or connector (for example, hardwired communications via USB).

Moreover, as indicated above, biometric monitoring device 10 may communicate with local or remote external devices and/or appliances as well as selected or user-specified websites on the Internet. (See, for example, FIGS. 6A, 6B and 6C). In one embodiment, biometric monitoring device 10 is programmed or configured via local or remote devices (whether via or over the Internet or point-to-point connection). In another embodiment, the portable activity monitoring device may communicate with biometric monitoring device as well as selected or user-specified external devices and/or websites on the Internet. (See, for example, FIG. 6D). In this embodiment, the portable activity monitoring device acts as a communication hub in relation to biometric monitoring device 10 and a remote device or the Internet. For the avoidance of doubt, all means and/or techniques of communication, whether now known or later developed, are intended to fall within the scope of the present invention.

Notably, although much of the discussion above in connection with communication with a portable monitoring device having activity sensors (to detect the activity of the user), such secondary or external device(s) may include one or more environmental sensors to detect, measure and/or sense ambient environmental conditions (in addition to the activity sensors or in lieu thereof) and may be stationary (e.g., a household appliance). For example, the secondary monitoring device may include one or more environmental sensors to detect, measure and/or sense ambient pressure, temperature, sound, light, humidity, location and/or atmosphere. As noted above, biometric monitoring device 10 may include communication circuitry to receive data from the secondary monitoring device and, in one embodiment, store such data in resident memory and/or upload such data (whether or not processed) to one or more local (for example, via a LAN) or remote data storage devices (for example, remote data storage devices via the internet). All discussions regarding biometric monitoring device 10 in relation to the secondary monitoring device having one or more activity sensors is applicable to other monitoring devices having one or more activity sensors and/or environmental sensors. For the sake of brevity, such discussions will not be repeated.

As mentioned above, biometric monitoring device 10 may store and/or transmit the raw data or pseudo-raw (i.e., processed) data from one or more (or all) of the sensor(s). For example, biometric monitoring device 10 may store and/or transmit data which is representative of weight, body fat, heart waveform (for example, ECG trace), heart rate, blood sugar, blood pressure and/or EEG. Notably, the data which is stored and/or transmitted may be filtered versions of the aforementioned, for example, filtered using passive elements (for example, RC networks) and/or active elements (for example, active electronics), frequency-domain methods (Butterworth filter, etc.), statistical methods (Kalman filter, etc.), time-series analysis (ARX models, etc.) and/or wavelets.

The raw or pseudo-raw (for example, filtered versions) of the aforementioned data may be stored and/or transmitted in time epochs that differ from the original (e.g., 1 Hz instead of 100 Hz) or in summary versions (e.g., mean, variance, integral, power, coefficient of variation, etc.) and may include signal quantities that are derived typically for use in a classification algorithm and other downstream calculations. In addition, the raw or pseudo-raw (for example, filtered versions) of the aforementioned data may be stored and/or transmitted in compressed or uncompressed formats. Such data may also be stored and/or transmitted in a matched to a value format that, for example, captures the approximate or exact value of the data (e.g., look-up table, ranges like "small", "medium" and "large").

Notably, in addition to receiving activity data, environmental data and/or physiologic data (from, for example, a portable monitoring device and/or local application or sensor) to, for example, store (i) within the biometric monitoring device and/or (ii) remotely from the biometric monitoring device (for example, off-site via the internet) in one or more selected data storage devices, the communication circuitry of the biometric monitoring device may also facilitate programming of the activity monitoring device, for example, programming the device to acquire selected activity and/or physiologic data (for example, via enabling and/or disabling selected sensors), acquiring activity and/or physiologic data, and/or calculate, monitor and/or determine selected activity parameters (for example, via enabling or disabling processing circuitry 16 accordingly). In this way, for example, a user may upload activity data, environmental data or physiologic data to, for example, one or more selected data storage devices. Notably, the one or more data storage devices may store the data in digital and/or analog form; indeed, any data storage device, whether now known or later developed, is intended to fall within the scope of the present inventions.

It should be noted that the term "circuit" may mean, among other things, a single component or a multiplicity of components (whether in integrated circuit form or otherwise), which are active and/or passive, and which are coupled together to provide or perform a desired function. The term "circuitry" may mean, among other things, a circuit (whether integrated or otherwise), a group of such circuits, one or more processors, one or more state machines, one or more processors implementing software, one or more gate arrays, programmable gate arrays and/or field programmable gate arrays, or a combination of one or more circuits (whether integrated or otherwise), one or more state machines, one or more processors, one or more processors implementing software, one or more gate arrays, programmable gate arrays and/or field programmable gate arrays. The term "data" may mean, among other things, a current or voltage signal(s) whether in an analog or a digital form, which may be a single bit (or the like) or multiple bits (or the like).

The various features, elements and/or circuitry of the biometric monitoring device may be disposed or integrated in or on one platform/housing or may be disposed in or on, or dispersed among a plurality of platforms/housings. FIGS. 16A-16D depict exemplary embodiments of the distribution of components of biometric monitoring device 10 across multiple platforms/housings. In one embodiment, the components, elements or circuitry in/on the different platforms/housings may be "interconnected", for example, electrically, mechanically and/or optically. In addition thereto, or in lieu thereof, such components, elements or circuitry may be interconnected (and function together) through wireless communication circuitry (for example, electrical, optical or audio). In yet another embodiment, they may be configured to be attachable and detachable. The following configurations/embodiments are exemplary:

1. The biometric monitoring device consists of a platform situated on the ground and a separate display (for example, a wall-mounted display). The platform facilitates acquisition of the aforementioned physiologic data (for example, weight, body fat, lean muscle mass, and/or heart rate) and the display presents the user with the aforementioned or associated data. The display and platform may communicate, for example, via electrical, optical, wireless and/or wired communication including, for example, LAN or WAN. Indeed, in one embodiment, the display may be or resemble a mirror wherein a portion thereof is dedicated for display or the physiologic data is presented to the user in a manner similar to heads-up display.
2. The biometric monitoring device consists of a weighing platform situated on the ground and a separate wall-mounted device that measures heart rate, respiratory rate, blood pressure, user height, sun exposure, hair length, wrinkles, etc. with one or more video cameras. The wall-mounted and floor-situated devices may both have displays to present the user with information.
3. The biometric monitoring device of #2 with an additional device that acts as a detachable remote control.
4. The biometric monitoring device of #3 with an additional device that may act as a handheld pulse oximeter to measure heart rate and oxygen saturation, a thermometer to measure body temperature, a blood pressure cuff, a set of bio-impedance analysis electrodes for hand-to-foot body fat analysis, a blood glucose meter.
5. The biometric monitoring device consists of a weighing platform situated on the ground and a separate wall-mounted or hand-held device that measures heart rate through electrocardiography.
6. The biometric monitoring device consists of a weighing platform situated on the ground and a separate wall-mounted device that measures body temperature with an infrared sensor. The infrared sensor may comprise photodetectors, photodiodes, or a camera and the user may or may not be illuminated with an external light source. The wall-mounted and floor-situated devices may both have displays to present the user with information.
7. The biometric monitoring device consists of a weighing platform situated on the ground and a separate wall-mounted device that measures heart rate, respiratory rate, blood pressure with one or more photodetectors, either using ambient light or active illumination. Illumination may be achieved with onboard lighting or control of external lighting fixtures in the room. The wall-mounted and floor-situated devices may both have displays to present the user with information.
8. The aforementioned inventions that incorporate a wall-mountable display wherein the display is instead provided by wall projection.
9. The biometric monitoring device of #1 wherein the display comprises a plurality of camera sensors at known positions which may image the user to compose a 3D model of the user's face and/or body.
10. The biometric monitoring device of #1 wherein the display comprises one or more cameras and one or more light sources that can be controlled to illuminate the user in specific patterns so as to image the user and compose a 3D model of the user's face and/or body. The lights may optionally be a combination of external light fixtures and onboard lights.

As such, the present inventions are not limited a biometric monitoring device wherein the components, elements and/or circuitry of the biometric monitoring device are disposed or integrated in or on one platform/housing. Notable, the aforementioned exemplary embodiments are intended or presented for illustration purposes and all permutations and combinations of features, elements and/or circuitry of the biometric monitoring device (as described in this application) whether integrated in one platform/housing or dispersed among a plurality of platforms/housings, are intended to fall within the scope of the present inventions. For the sake of brevity, all of the permutations and combinations of components, elements and/or circuitry in conjunction with one platform/housing or a plurality of platforms or housings are not discussed and/or illustrated separately herein.

Figure 17:
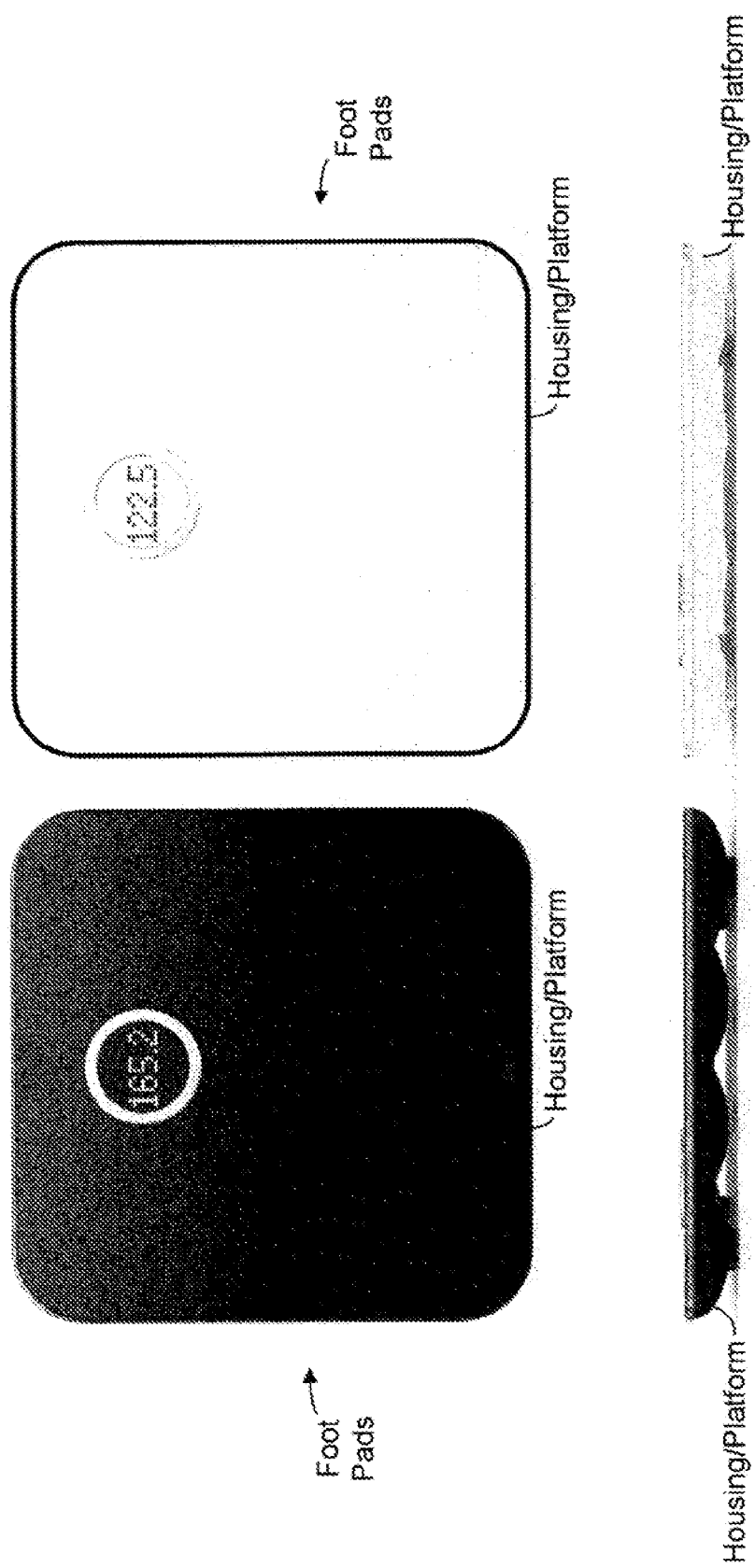
FIG. 17 illustrates exemplary platforms/housings of the biometric monitoring device from top and side views, according to at least certain aspects of certain embodiments of the present inventions.
Figure 18:
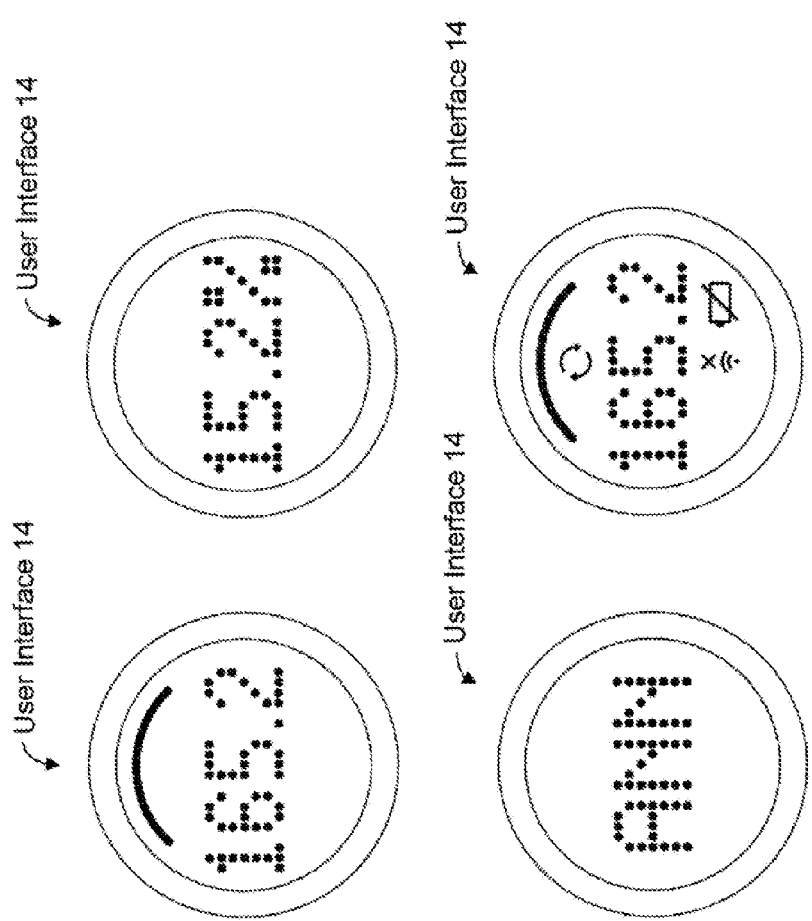
FIG. 18 illustrates exemplary user interfaces of the biometric monitoring device, wherein the user interface may provide information which is representative of biometric information (for example, weight, percent body fat and/or BMI) and operating conditions of the device (for example, power levels, communication conditions, etc.).

The platform/housing of biometric monitoring device 10 may take any shape or configuration, all of which are intended to fall within the scope of the present inventions. In one embodiment, biometric monitoring device 10 may include a housing/platform wherein user interface 14 is disposed between the foot pads and the bottom may be sculpted in an undulating form (see, FIG. 17). Where the device includes a thin film of conductive material on its surface (e.g., ITO) to be used in applications such as measuring body fat, hydration, and the like and/or used as a touch-based interface (e.g., buttons), the connections of the conductive film to the device's internal circuitry may be situated below the main display so that they not visible (see FIG. 17). The display may be made of or include a conductive material (e.g., a metal ring) in order to electrically connect different segments of the film. In a preferred embodiment, the display has an outer conductive metallic ring situated above a nonconductive plastic lens so that 1) the outer ring does not electrically connect to the conductive thin film on the top surface of the device and 2) the display may be viewed through the lens. Notably, user interface 14 of biometric monitoring device 10 may provide information which is representative of biometric information (for example, weight, percent body fat and/or BMI), activity data (for example, from a portable monitoring device, and/or operating conditions of biometric monitoring device 10 (for example, power levels, communication conditions, etc.) and/or the portable monitoring device. (See, FIG. 18).

It should be further noted that the various circuits and circuitry disclosed herein may be described using computer aided design tools and expressed (or represented), as data and/or instructions embodied in various computer-readable media, for example, in terms of their behavioral, register transfer, logic component, transistor, layout geometries, and/or other characteristics. Formats of files and other objects in which such circuit expressions may be implemented include, but are not limited to, formats supporting behavioral languages such as C, Verilog, and HLDL, formats supporting register level description languages like RTL, and formats supporting geometry description languages such as GDSII, GDSIII, GDSIV, CIF, MEBES and any other suitable formats and languages. Computer-readable media in which such formatted data and/or instructions may be embodied include, but are not limited to, non-volatile storage media in various forms (e.g., optical, magnetic or semiconductor storage media) and carrier waves that may be used to transfer such formatted data and/or instructions through wireless, optical, or wired signaling media or any combination thereof. Examples of transfers of such formatted data and/or instructions by carrier waves include, but are not limited to, transfers (uploads, downloads, e-mail, etc.) over the Internet and/or other computer networks via one or more data transfer protocols (e.g., HTTP, FTP, SMTP, etc.). The present inventions are also directed to such representation of the circuitry described herein, and/or techniques implemented thereby, and, as such, are intended to fall within the scope of the present inventions.

Indeed, when received within a computer system via one or more computer-readable media, such data and/or instruction-based expressions of the above described circuits may be processed by a processing entity (e.g., one or more processors) within the computer system in conjunction with execution of one or more other computer programs including, without limitation, net-list generation programs, place and route programs and the like, to generate a representation or image of a physical manifestation of such circuits. Such representation or image may thereafter be used in device fabrication, for example, by enabling generation of one or more masks that are used to form various components of the circuits in a device fabrication process.

Moreover, the various circuits and circuitry, as well as techniques, disclosed herein may be represented via simulations and simulation instruction-based expressions using computer aided design, simulation and/or testing tools. The simulation of the various sensors, processing circuitry, user interface, transmitter circuitry and/or receiver circuitry of the present inventions (regardless of combination or permutation of sensors, processing circuitry, transmitter circuitry and/or receiver circuitry), including the processes or techniques implemented thereby, may be implemented by a computer system wherein characteristics and operations of such circuitry, and techniques implemented thereby, are simulated, imitated, replicated, analyzed and/or predicted via a computer system. The present inventions are also directed to such simulations and testing of the inventive biometric monitoring device (or portions thereof including, for example, the various sensors, processing circuitry, user interface, input/output circuitry (although not illustrated—the input/output circuitry may be discrete circuitry or circuitry which is integrated into the processing circuitry), transmitter circuitry and/or receiver circuitry), and/or techniques implemented thereby, and, as such, are intended to fall within the scope of the present inventions. The computer-readable media and data corresponding to such simulations and/or testing tools are also intended to fall within the scope of the present inventions.

The term "calculate" and other forms (i.e., calculating, calculated and calculation) in the claims means, among other things, calculate, assesses, determine and/or estimate and other forms thereof. The term "activity data" in the claims means, among other things, data corresponding to activity, food consumption and/or sleep. In addition, the term "user identification data" or the like, as used herein and in the claims, is any data that identifies a particular user, a particular device and/or from which a particular user or device may be determined; the user identification data may be data separate from the physiologic, activity and/or environmental data and/or may be incorporated or integrated in the physiologic, activity and/or environmental data; moreover, the user identification data may be implied from the communication with an external device (for example, portable activity monitoring device and/or biometric device) and/or implied from other data (for example, the physiologic data from a biometric monitoring device and/or activity data or physiologic data from a portable activity monitoring device and/or biometric device).

Notably, the terms "first," "second," and the like, herein do not denote any order, quantity, or importance, but rather are used to distinguish one element from another. Moreover, in the claims, the terms "a" and "an" herein do not denote a limitation of quantity, but rather denote the presence of at least one of the referenced item.

What is claimed is:

1. A biometric monitoring system to measure a body weight of a user, the biometric monitoring system comprising:
   a housing configured to be placed on a flat horizontal surface and including a platform configured to receive at least one foot of the user and capable of supporting the body weight of the user;
   one or more physiological sensors, wherein the one or more physiological sensors includes a body weight sensor, mechanically coupled to the platform and configured to generate data representative of the body weight of the user and to output the data representative of the body weight of the user to processing circuitry; and
   the processing circuitry, wherein the processing circuitry is:
      communicatively coupled with the one or more physiological sensors,
      configured to calculate biometric data from the one or more physiological sensors,
      wherein the biometric data includes body weight data that corresponds to the body weight of the user and that is based on the data representative of the body weight of the user,
      configured to compare a user physiological goal with the biometric data and determine that the user physiological goal has been met based, at least in part, on the biometric data;
      configured to recommend a social group to the user based, at least in part, on information selected from the group consisting of: a) the user physiological goal, b) the data representative of the body weight of the user, and c) the user physiological goal and the data representative of the body weight of the user, the recommendation being presented through a display; and
      configured to rank the user against other members of the social group based on one or more parameters selected from the group consisting of: recent weight lost, cumulative weight lost, and progress towards the user physiological goal.

2. The biometric monitoring system of claim 1, wherein the one or more physiological sensors further includes, in addition to the body weight sensor, a first physiological sensor configured to collect data selected from the group consisting of: caloric consumption data, sleep data, activity data, body fat data, blood pressure data, heart rate data, heart waveform data, blood sugar data, hydration data, respiratory rate data, and arterial stiffness data.

3. The biometric monitoring system of claim 1, wherein the processing circuitry is selected from the group consisting of: processing circuitry internal to the housing, processing circuitry external to the housing, and processing circuitry both internal and external to the housing.

4. The biometric monitoring system of claim 1, wherein the one or more physiological sensors further includes a first physiological sensor in addition to the body weight sensor, wherein:
   the first physiological sensor is configured to generate data representative of a first physiological state of the user and output the data representative of the first physiological state of the user to the processing circuitry; and
   the processing circuitry is configured to calculate first physiological data using the data representative of the first physiological state of the user.

5. The biometric monitoring system of claim 4, wherein the first physiological sensor is selected from the group consisting of: a body fat sensor, a heart rate sensor, a respiratory rate sensor, a hydration sensor, a height sensor, a blood pressure sensor, an arterial stiffness sensor, and a bio-impedance sensor.

6. The biometric monitoring system of claim 4, wherein the data representative of the first physiological state of the user is selected from the group consisting of: data representative of user body fat, data representative of user heart rate, data representative of user respiratory rate, data representative of user hydration, data representative of user height, data representative of user sun exposure, data representative of user blood pressure, and data representative of user arterial stiffness.

7. The biometric monitoring system of claim 4, further comprising a user interface, wherein:
   the user interface is configured to communicate that the user physiological goal has been met,
   the processing circuitry is further configured to determine user physiological information using data selected from the group consisting of: the body weight data and the first physiological data,
   the processing circuitry is further configured to store historical user physiological information in a memory disposed in a location selected from the group consisting of: a location inside of the housing and a location external to the housing, and
   the user interface communicates that the user physiological goal has been met through providing information representing one or more of current user physiological information, historical user physiological information, and current user physiological information in view of historical user physiological information.

8. The biometric monitoring system of claim 7, wherein the user physiological information is selected from the group consisting of: exercise or diet data, exercise or diet coaching, exercise or data instructions, and user progress towards the user physiological goal.

9. The biometric monitoring system of claim 1, wherein the user physiological goal is selected from the group consisting of: a weight goal, a body fat composition goal, and a caloric consumption goal.

10. The biometric monitoring system of claim 1, wherein the processing circuitry is further configured to determine diet or coaching guidance for the user based on the user physiological goal.

11. The biometric monitoring system of claim 1, further comprising a user interface, wherein the user interface is configured to communicate that the user physiological goal has been met responsive to a determination that the user physiological goal has been met.

12. The biometric monitoring system of claim 11, wherein the user interface comprises an audio interface.

13. The biometric monitoring system of claim 11, wherein the user interface comprises a visual display and the processing circuitry is configured to cause the display to present a graphical representation that the user physiological goal has been met responsive to the determination that the user physiological goal has been met.

14. The biometric monitoring system of claim 1, further comprising a user interface, wherein the processing circuitry is further configured to select the user physiological goal responsive to user interaction with the user interface.

15. The biometric monitoring system of claim 1, wherein the processing circuitry is further configured to select the user physiological goal.

16. The biometric monitoring system of claim 1, wherein the processing circuitry is further configured to determine a duration since at least the last instance of the user interacting with the biometric monitoring system.

17. A biometric monitoring system to measure a body weight of a user, the biometric monitoring system comprising:
- a housing configured to be placed on a flat horizontal surface and including a platform configured to receive at least one foot of the user and capable of supporting the body weight of the user;
- one or more physiological sensors, wherein the one or more physiological sensors includes a body weight sensor, interconnected with the housing and configured to generate data representative of the body weight of the user and to output the data representative of the body weight of the user to processing circuitry; and
- the processing circuitry including circuitry configured to communicatively couple with the one or more physiological sensors, wherein the processing circuitry is:
  - configured to, when communicatively coupled to the one or more physiological sensors, calculate biometric data from the one or more physiological sensors, wherein the biometric data includes body weight data that corresponds to the body weight of the user and that is based on the data representative of the body weight of the user,
  - configured to, when communicatively coupled to the one or more physiological sensors, compare a user physiological goal with the biometric data and determine that the user physiological goal has been met based, at least in part, on the biometric data; and
  - configured to, when communicatively coupled to the one or more physiological sensors, rank the user against a plurality of other users in a social network based on one or more parameters selected from the group consisting of: recent weight lost, cumulative weight lost, and progress towards the user physiological goal.

18. The biometric monitoring system of claim 17, wherein the processing circuitry is further configured to, when communicatively coupled to the one or more physiological sensors, recommend a social group to the user based, at least in part, on information selected from the group consisting of: a) the user physiological goal, b) the data representative of the body weight of the user, and c) the user physiological goal and the data representative of the body weight of the user, the recommendation being provided through a user interface.

19. The biometric monitoring system of claim 17, wherein the one or more physiological sensors further includes, in addition to the body weight sensor, a first physiological sensor configured to collect data selected from the group consisting of: caloric consumption data, sleep data, activity data, body fat data, blood pressure data, heart rate data, heart waveform data, blood sugar data, hydration data, respiratory rate data, and arterial stiffness data.

20. The biometric monitoring system of claim 17, wherein the processing circuitry is selected from the group consisting of: processing circuitry internal to the housing, processing circuitry external to the housing, and processing circuitry both internal and external to the housing.

* * * * *